(12) United States Patent
Feinberg et al.

(10) Patent No.: US 9,068,168 B2
(45) Date of Patent: *Jun. 30, 2015

(54) BOUNDARY CONDITIONS FOR THE ARRANGEMENT OF CELLS AND TISSUES

(75) Inventors: Adam W. Feinberg, Cambridge, MA (US); Kevin Kit Parker, Waltham, MA (US); Po-Ling Kuo, Tainan (TW); Chin-Lin Guo, Tainan (TW)

(73) Assignee: President and Fellows of Harvard College, Cambridge, MA (US)

( * ) Notice: Subject to any disclaimer, the term of this patent is extended or adjusted under 35 U.S.C. 154(b) by 1267 days.

This patent is subject to a terminal disclaimer.

(21) Appl. No.: 12/680,277

(22) PCT Filed: Sep. 26, 2008

(86) PCT No.: PCT/US2008/011173
§ 371 (c)(1),
(2), (4) Date: Sep. 1, 2010

(87) PCT Pub. No.: WO2009/085067
PCT Pub. Date: Jul. 9, 2009

(65) Prior Publication Data
US 2010/0330644 A1     Dec. 30, 2010

Related U.S. Application Data

(60) Provisional application No. 60/995,653, filed on Sep. 26, 2007.

(51) Int. Cl.
*C12N 5/00*     (2006.01)
*C12N 5/077*    (2010.01)
(Continued)

(52) U.S. Cl.
CPC ............ *C12N 5/0658* (2013.01); *C12N 5/0657* (2013.01); *C12N 2533/52* (2013.01); *C12N 2535/10* (2013.01); *C12N 2539/10* (2013.01)

(58) Field of Classification Search
None
See application file for complete search history.

(56) References Cited

U.S. PATENT DOCUMENTS

2004/0009566 A1   1/2004  Okano et al.
2004/0078090 A1   4/2004  Binette et al.
(Continued)

FOREIGN PATENT DOCUMENTS

WO   WO 2011/102991   8/2011
WO   WO 2012/006320   1/2012
WO   WO 2012/048242   4/2012

OTHER PUBLICATIONS

Bursac N, Parker KK, Iravanian S, and Tung L "Cardiomyocyte Cultures with Controlled Macroscopic Anisotropy: a Model for Functional Electrophysiological Studies of Cardiac Muscle." Circ Res. Dec. 13, 2002 (published online Nov. 14, 2002), 91(12), pp. e45-54 (express communication and supplemental content, 13 pages).*

(Continued)

*Primary Examiner* — Jon P Weber
*Assistant Examiner* — Aaron J Kosar
(74) *Attorney, Agent, or Firm* — McCarter & English, LLP; Maria Laccotripe Zacharakis; Deborah L. Nagle

(57) ABSTRACT

The present invention relates to the arrangement of one or more cells in a medium or on a substrate through the use of boundary conditions, which are changes in local environment compared to the medium or substrate alone or cause an alteration of cell response upon interaction of a cell with the boundary condition.

10 Claims, 20 Drawing Sheets

(51) Int. Cl.
A61K 35/34 (2006.01)
C12N 5/02 (2006.01)
C12N 5/071 (2010.01)
C12N 5/07 (2010.01)

(56) References Cited

U.S. PATENT DOCUMENTS

| | | |
|---|---|---|
| 2004/0101819 A1 | 5/2004 | Montemagno et al. |
| 2005/0080402 A1 | 4/2005 | Santamore et al. |
| 2005/0085847 A1 | 4/2005 | Galdonik et al. |
| 2006/0003439 A1 | 1/2006 | Ismagilov et al. |
| 2009/0317852 A1 | 12/2009 | Parker et al. |
| 2010/0196432 A1 | 8/2010 | Feinberg et al. |
| 2011/0189719 A1 | 8/2011 | Kuo et al. |
| 2012/0142556 A1 | 6/2012 | Parker et al. |

OTHER PUBLICATIONS

Bray, Mark-Anthony; Sheehy, Sean P.; and Parker, Kevin Kit "Sarcomere Alignment is Regulated by Myocyte Shape" Cell Motility and the Cytoskeleton, Aug. 2008 (published online Jun. 16, 2008, 65(8), pp. 641-651.*
Hu, S et al "Mechanical Anisotropy of Adherent Cells Probed by a Three-dimensional Magnetic Twisting Device" Am J Physiol Cell Physiol, 2004, 287(5), pp. C1184-C1191.*
Bursac et al., "Cardiomyocyte cultures with controlled macroscopic anisotropy." *Circulation Rearch*, 2002, vol. 91, pp. e45-e54.
Lehnert et al., "Cell behavior on micropatterned substrata: limits of extracellular matrix geometry fro spreading and adhesion."*Journal of Cell Science*, 2004, vol. 117, pp. 41-52.
Parker et al., "Ectracellular matrix, mechanotransduction and struction hierarchies in heart tissue engineering." *Phil Trans R. Soc B*, Epub Jun. 22, 2007, vol. 362, pp. 1267-1279.
Yang et al., "Fabrication of well-defined PLGA scaffolds using novel microembossing and carbon dioxide bonding", Biomaterials, 2005, vol. 26, pp. 2585-2594.
Xi et al., "Development of a Self-Assembled Muscle-Powered Piezoelectric Microgenerator", NSTI-Nanotech, 2004, vol. 1, pp. 3-6.
Anversa et al., "Morphometry of exercise-induced right ventricular hypertrophy in the rat." (1983) Circ Res 52:57-64.
Anversa et al., "Myocyte Cell Loss and Myocyte Hypertrophy in the Aging Rat Heart" (1986) J Amer Coll Cardiol 7:1140-9.
Atherton et al., "Assembly and remodeling of Myofibrils and Intercalated Discs in Cultured Neonatal Rat Heart Cells" (1986) J Cell Sci 86:233-48.
Balaban et al., "Force and focal adhesion assembly: a close relationship studied using elastic micropatterned substrates" (2001) Nat Cell Biol 3:466.
Beauchamp et al., "Relative Contributions of Connexins 40 and 43 to Atrial Impulse Propagation in Synthetic Strands of Neonatal and Fetal Murine Cardiomyocytes" (2006) Circ Res 99:1216-24.
Bershadsky et al., "Adhesion-Dependent Cell Mechanosensitivity" (2003) Annu Rev Cell Dev Biol 19:677.
Brancaccio et al., "Integrin signalling: The tug-of-war in heart hypertrophy" (2006) Cardiovasc Res 70:422-33.
Brower et al., "The relationship between myocardial extracellular matrix remodeling and ventricular function" (2006) Eur J Cardiothorac Surg 30:604-10.
Bursac et al., "Multiarm spirals in a two-dimensional cardiac substrate" (2004) Proc Natl Acad Sci USA 101:15530-4.
Camelliti et al., "Microstructured Cocuhures of Cardiac Myocylesand Fibroblasts: A Two Dimensional in Vitro Model of Cardiac Tissue" (2005) Microsc Microanal 11:249-59.
Chen et al., "Geometric Control of Cell Life and Death" (1997) Science 276:1425-8.
Chen et al., "Cell shape provides global control of focal adhesion assembly" (2003) Biochem Biophys Res Commun 307:355-61.
Chen et al., "Regional ventricular wall thickening reflects changes in cardiac fiber and sheet structure during contraction: quantification with diffusion tensor MRI" (2005) Am J. Physio.-Heart Circul Physiol 289:H1898-H1907.

Chrzanowska-Wodnicka et al., "Rho-Stimulated Contractility Drives the Formation of Stress Fibers and Focal adhesions" (1996) J Cell Biol 133:1403.
Dabiri et al., "Myofibrillogenesis visualized in living embryonic cardiomyocytes" (1997) Proc Natl Aced Sci USA 94:9493.
Danowski et al., "Costameres Are Sites of Force Transmission to the Substratum in Adult Rat Cardiomyoctes" (1992) J Cell Biol 118:1411-20.
Dembo et al., "Stresses at the Cell-to-Substrate Interface during Locomotion of Fibroblasts" (1999) Biophys J 76:2307.
Ding et al., "Left Ventricular Hypertrophy in Ascending Aortic Stenosis Mice : Anoikis and the Progression to Early Failure" (2000) Circulation 101:2854-62.
Dlugosz et al. "The Relationship between Stress Riber-Like Structures and Nascent Myofibrils in Cultured Cardiac Myocytes" (1984) J Cell Biol 99:2268.
Du et al., "Myofibrillogenesis in the first cardiomyocytes formed from isolated quail precardiac mesoderm" (2003) Dev Biol 257:382.
Ehler et al., "Myofibrillogenesis in the developing chicken heart: assembly of Z-disk, M-line and the thick filaments" (1999) J Cell Sci 112 (Pt 10):1529.
Ezzell et al., "Vinculin Promotes Cell Spreading by Mechanically Coupling Integrins to the Cytoskeleton" (1997) Exp Cell Res 231:14-26.
Feinberg et al., "Muscular Thin Films for Building Actuators and Powering Devices" (2007) Science 317:1366-1370.
Furuta et al., "Pulsatile Cardiac Tissue Grafts Using a Novel Three-Dimensional Cell Sheet Manipulation Technique Functionally Integrates With the Host Heart, In Vivo" (2006) Circ Res 98:705-12.
Galbraith et al., "The relationship between force and focal complex development" (2002) J Cell Biol 159:695.
Gerdes et al. (1988) Lab Invest 59:857-61.
Gerdes et al. (1992) Circulation 86:426-30.
Gopalan et al., "Anisotropic Stretch-induced Hypertrophy in Neonatal Ventricular Myocytes Micropatterned on Deformable Elastomers" (2003) Biotechnol Bioeng 81:578-87.
Harrington, et al., "Direct measurement of transmural laminar architecture in the anterolateral wall of the ovine left ventricle: new implications for wall thickening mechanics" (2005) Am J Physiol-Heart Circul Physiol 288:H1324-H1330.
Hilenski et al. "Myofibrillar and cytoskeletal assembly in neonatal rat cardiac myocytes cultured on laminin and collagen" (1991) Cell and Tissue Research 264:577-87.
Holtzer et al., "Independent Assembly of 1.6 /an Long Bipolar MHCFilaments and I-Z-I Bodies" (1997) Cell Struct Funct 22:83.
Huang et al. , "Control of Cyclin D1, p27Kip1, and Cell Cycle Progression in Human Capillary Endothelial Cells by Cell Shape and Cytoskeletal Tension" (1998) Mol Biol Cell 9:3179-93.
Ingber, "Integrins as Mechanochemical transducers" (1991) Current Opinion in Cell Biology 3:841-8.
Jiang et al., "Directing cell migration with asymmetric micropatterns" (2005) Proc Natl Acad Sci USA 102:975-8.
Komuro et al., "Control of Cardiac Gene Expression by Mechanical Stress" (1993) Annu Rev Physiol 55:55-75.
Legrice et al. "Laminar structure of the heart: ventricular myocyte arrangement and connective tissue architecture in the dog" (1995) Am J Physiol-Heart Circul Physiol 38:H571-H582.
Lehnert et al., "Cell behaviour on micropatterned substrata: limits of extracellular matrix geometry for spreading and adhesion" (2004) J Cell Sci 117:41-52.
Lin et al., "Polygons and Adhesions Plaques and the Disassembly and Assembly of Myofibrils in Cardiac Myocytes" (1989) J Cell Biol 108:2355-67.
Lu et al., The Vinculin/Sarcomeric-α-Actinin/α-Actin Nexus in Cultured Cardiac Myocytes: (1992) J Cell Biol 117:1007-22.
Mansour et al., "Restoration of Resting Sarcomere Length After Uniaxial Static Strain Is Regulated by Protein Kinase C_ and Focal Adhesion Kinase" (2004) Circ Res 94:642-9.
Maxwell et al., "The integration of tissue structure and nuclear Function" (2001) Biochemistry and Cell Biology 79:267-74.
McKenna et al., "Formation and Alignment of Z Lines in Living Chick Myotubes Microinjected with Rhodamine-Labeled Alpha-Actinin" (1986) J Cell Biol 103:2163.

(56) References Cited

OTHER PUBLICATIONS

O'Neill et al., "Narrow linear strips of adhesive substratum are powerful inducers of both growth and total focal contact area" (1990) J Cell Sci 95:577-86.

Novak et al., "Cooperativity between Cell Contractility and Adhesion" (2004) Phys Rev Lett 93, 268109.

Onodera et al., "Maladaptive Remodeling of Cardiac Myocyte Shape Begins Long Before Failure in Hypertension" (1998) Hypertension 32:753-7.

Parker et al., "Directional control of lamellipodia extension by constraining cell shape and orienting cell tractional forces" (2002) Faseb J 16:1195.

Pelham et al., "Cell locomotion and focal adhesions are regulated by substrate flexibility" (1997) Proc Natl Aced Sci USA 94:1366.

Rhee et al., "The Premyofibril: Evidence for Its Role in Myofi brillogenesis"(1994) Cell Motil Cytoskeleton 28:1.

Rohr et al., "Patterned growth of neonatal rat heart cells in culture. Morphological and electrophysiological characterization" (1991) Circ Res 68:114-30.

Rothen-Rutishauser et al., "Different Behaviour of the Non-sarcomeric Cytoskeleton in Neonatal and Adult Rat Cardiomyocytes" (1998) J Mol Cell Cardiol 30:19-31.

Russell et al., "Form follows function: how muscle shape is regulated by work" (2000) J Appl Physiol 88, 1127.

Samarel, "Costameres, focal adhesions, and cardiomyocyte mechanotransduction" (2006) Am J Physiol Heart Circ Physiol 289:H2291-H2301.

Sands et. al., "Automated Imaging of Extended Tissue Volumes Using Confocal Microscopy"Microscopy Research and Technique 67:227-239 (2005).

Sanger et al., "Myofibrillogenesis in Living Cells Microinjected with Fluorescently Labels Alpha-Actinin" (1986) J Cell Biol 102:2053.

Siegrist et al., "Extrinsic cues orient the cell division axis in *Drosophila* embryonic neuroblasts" (2006) Development 133:529.

Simpson et al., "Mechanical regulation of cardiac myocyte protein turnover and myofibrillar structure" (1996) Am J Physiol Cell Physiol 270:C1075-C1087.

Simpson et al. "Regulation of Cardiac Myocyte Protein Turnover and Myofibrillar Structure in Vitro by Specific Directions of Stretch" (1999) Circ Res 85:e59-e69.

Singhvi et al., "Engineering Cell Shape and Function" (1994) Science 264:696-8.

Smilenov et al., "Focal Adhesion Motility Revealed in Stationary Fibroblasts" (1999) Science 286:1172.

Smith et al., "Regional Myocyte Size in Compensated Right Ventricular Hypertrophy in the Ferret" (1985) 17:1005-11.

Tan et al., "Simple Approach to Micropattern Cells on Common Culture Substrates by Tuning Substrate Wettability" (2004) Tissue Eng 10:865.

Thery et al., "Cell Distribution of Stress Fibres in Response to the Geometry of the Adhesive Environment" (2006) Cell Motil Cytoskeleton 63:341.

Tokuyasu et al., "Intermediate Filaments in Skeletal and Cardiac Muscle Tissue in Embryonic and Adult Chicken ""(1985) Ann NY Acad Sci 455:200-12.

Tokuyasu, "Immunocytochemical Studies of Cardiac Myofibrillogenesis in Early Chick Embryos. III. Generation of Fasciae Adherentes and Costamers"(1989) J Cell Biol 108:43-53.

Torsoni et al., "Focal Adhesion Kinase Is Activated and Mediates the Early Hypertrophic Response to Stretch in Cardiac Myocytes" (2003) Circ Res 93:140.

Young et. al., "Extended confocal microscopy of myocardial laminae and collagen network" Journal of Microscopy, vol. 192, Pt 2, Nov. 1998, pp. 139-150.

Y. L. Wang (1984) J Cell Biol 99:1478.

Wang et al., "Micropatterning Tractional Forces in Living Cells" (2002) Cell Motil Cytoskeleton 52:97.

Weiss et al., "Shape and Movement of Mesenchyme Cells as Functions of the Physical Structure of the Medium Contributions to a Quantitative Morphology" (1952) Proc Natl Acad Sci USA 38:264-80.

Zamir et al., "Dynamics and segregation of cell—matrix adhesions in cultured fibroblasts" (2000) Nat Cell Biol 2:191.

\* cited by examiner $\ell$ = longitudinal length of boundary condition
$w_A$ = lateral width of surface property A
$w_B$ = lateral width of surface property B
$d$ = depth of surface property A or B

BOUNDARY CONDITIONS FOR THE ARRANGEMENT OF CELLS AND TISSUES

GOVERNMENT SUPPORT

This invention was supported, in whole or in part, by Grant No. FA9550-05-1-0015 from the Defense Advanced Research Projects Agency (DARPA); Grant No. PHY-0117795 from the National Science Foundation; and Grant No. 1 RO1 HL079126-01A2 from the National Institutes of Health. The U.S. Government has certain rights in this invention.

CROSS-REFERENCE TO RELATED APPLICATIONS

This application claims priority to U.S. Provisional Patent Application No. 60/995,653, filed Sep. 26, 2007, which is incorporated by reference into this disclosure in its entirety.

BACKGROUND

In nature, living cells divide and interconnect in the formation of complex biological systems creating structure-function hierarchies that span from nanometer to meter scales. This bottom-up approach leverages genetic programming and environmental stimuli to direct cellular self-assembly and organogenesis into specialized tissues and organs. Capabilities, including the parallel processing of neural networks, the combination of force, strain and efficiency of striated muscle, and the immune response to pathogens, far exceed what can be achieved in manmade systems. Learning to use living cells as an integral building block in manmade, synthetic systems thus portends the ability to create classes of hybrid devices that combine the advantages of biological and engineering grade materials.

Efforts to build biosynthetic materials or engineered tissues that recapitulate these structure-function relationships often fail because of the inability to replicate the in vivo conditions that coax this behavior from ensembles of cells. For example, engineering a functional muscle tissue requires that the sarcomere and myofibrillogenesis be controlled at the micron length scale, while cellular alignment and formation of the continuous tissue require organizational cues over the millimeter to centimeter length scale. Thus, to build a functional biosynthetic material, the biotic-abiotic interface must contain the chemical and/or mechanical and/or physical properties that support multiscale coupling.

Multiscale coupling of properties over several length scales within a functional biosynthetic material often requires the anisotropic arrangement of hierarchical structures within that material. In the muscle tissue example, anisotropic arrangement of sarcomeres and muscle cells in striated muscle tissue concentrate contraction force along defined axes to effectuate coordinated movements of the skeleton. Methods to produce anisotropic arrangement of hierarchical structures are therefore desirable to focus particular properties of the material. Such methods could be used to control development of biotic tissue in association with an abiotic medium or substrate to produce an anisotropic environment, analogous to muscle attachment to bone.

SUMMARY OF THE INVENTION

Anisotropic arrangement within a biosynthetic material or engineered cell/tissue is achieved through the use of boundary conditions. Boundary conditions control the alignment of intracellular organelles. Described herein is a methodology that has been developed that uses boundary conditions to produce biosynthetic materials and engineered tissues with multiscaled coupling of properties achieved through anisotropic arrangement of one or more cells within the material.

Accordingly, an engineered tissue structure, comprises a medium or substrate; a plurality of isolated cells, an intracellular organelle of each of said cells being arranged in response to a boundary condition associated with the medium or substrate. An alteration of cell response occurs upon cell interaction with the boundary condition as compared to cell interaction with the medium or substrate alone, such that the alignment or arrangement of the intracellular organelle of the cells is spatially anisotropic in at least one direction. For example, the boundary condition is a change in local environment as compared to the environment of the medium or substrate alone, and the cells respond by arrangement of their intracellular organelles in a manner that is spatially anisotropic in at least one direction.

An organelle is a differentiated structure within a cell that performs a specific function. Organelles include cytoskeletal structures such as contractile units or organelles in muscle cells. In preferred embodiments, the muscle cell is a striated muscle cell (skeletal or cardiac) and the intracellular organelle is a contractile unit such as a sarcomere. Contractile organelles or other types of muscle cells, e.g., smooth, are also aligned using the methods described herein. For example, the muscle cell is a smooth muscle cell such as a vascular smooth muscle cell or gastrointestinal smooth muscle cell, the contractile unit/organelle of which is a dense body. The methods are also used to arrange cells by alignment of other subcellular organelles such as mitochondria.

The boundary condition is constructed into or onto a substrate or is naturally provided. For example, the substrate is comprised of a polymeric material. The boundary condition is physical, mechanical, chemical, or electromagnetic, e.g., a change in the local environment as compared to the environment of the medium or substrate alone. For example, an effective boundary condition is characterized by at least a 5-fold change in the local concentration of a composition on the substrate. Preferably, the change in local concentration is 10-fold, 25-fold, 50-fold, 100-fold or more compared to an adjacent area on the substrate. The substrate comprises a surface and the boundary condition comprises a surface feature. For example, the substrate comprises a surface and the boundary condition comprises a purified extracellular matrix protein (ECM) such as a purified fibronectin, laminin, fibrinogen, or a mixture of purified ECM or other compositions. For example, boundary conditions are made by deposition/patterning of mixtures of two (e.g., fibronectin and laminin), three, or more compositions (e.g., a mixture of proteins in naturally-occurring serum such as human or bovine serum or artificially produced serum compositions). Other compositions to be used in construction of a boundary condition include a nutritional composition, e.g., an omega-3 fatty acid, or a pharmaceutical agent.

A boundary condition may be physical, mechanical, chemical, or electromagnetic, and may be a surface feature. For example, a boundary condition is characterized by a difference in the amount or concentration of an extracellular matrix (ECM) protein in one location compared to another, e.g., adjacent location. The boundary is the point, line, or region of the difference. The change is at least 20%, 50%, 75%, 100%, 3-fold, 5-fold, 10-fold more or less than another e.g., adjacent location.

The compositions, e.g., an extracellular matrix (ECM) protein, described herein are purified, e.g., synthetically produced, recombinantly produced, and/or biochemically purified. A purified composition such as a protein or polypeptide is at least 60%, by weight, free from proteins and naturally occurring organic molecules with which it is naturally associated. Preferably, the preparation is at least 75%, more preferably 90%, and most preferably at least 99%, by weight, the desired composition. A purified antibody may be obtained, for example, by affinity chromatography. By "substantially pure" is meant a nucleic acid, polypeptide, or other molecule that has been separated from the components that naturally accompany it. Typically, the polypeptide is substantially pure when it is at least 60%, 70%, 80%, 90%, 95%, or 99%, by weight, free from the proteins and naturally-occurring organic molecules with which it is naturally associated. For example, a substantially pure polypeptide may be obtained by extraction from a natural source, by expression of a recombinant nucleic acid in a cell that does not normally express that protein, or by chemical synthesis. Boundary conditions are created by deposition of purified compositions such as an ECM protein, a nutritional composition, or a pharmaceutical composition, or a mixture of purified compositions on a substrate upon which the cells arrange by alignment of their intracellular organelles.

The boundary condition induces an alteration of cell response upon cell interaction with the boundary condition as compared to cell interaction with the medium or substrate alone. Cell interaction with the boundary condition leads to alignment of an intracellular organelle and thereby alignment/arrangement of the cells anisotropically in at least one direction. Further, the boundary condition may in addition guide coupling of multiple cells together into a tissue, maintaining the alignment of intracellular organelles within each cell.

A method of arranging or aligning cells such as muscle cells is carried out by providing a medium or substrate; providing a boundary condition associated with the medium or substrate; providing a cell associated with the medium or substrate; and allowing the cell to arrange by virtue of alignment of a subcellular organelle such as a sarcomere upon contact with the boundary condition. The cell is artificially provided, e.g., the substrate containing a pattern of boundary conditions is contacted with a suspension of dissociated cells. For example, the cells are dissociated from a tissue sample from a mammalian donor, e.g., a human subject, or are cells of a cell line that has been propagated in culture. An alteration of cell response occurs upon cell interaction with the boundary condition as compared to cell interaction with the medium or substrate alone, whereby the arrangement of intracellular organelles, e.g., sarcomeres, of the cells spatially align in an anisotropic manner in at least one direction.

Also within the invention is a system for aligning cells. The system includes a substrate and a boundary condition associated with the substrate. The substrate is characterized by a surface, which has a surface property that varies periodically along a length of the surface to form alternating regions on the surface. The boundary condition is characterized by an interface between the alternating regions on the surface. At least one of the alternating regions is configured to receive one or more cells, and the boundary condition functions to induce alignment of subcellular organelles, e.g., sarcomeres, of the cells on at least one of the alternating regions. An exemplary periodic variation of the surface property is selected from the group consisting of a square wave, a trapezoidal wave, a sinusoidal wave and a saw-tooth wave, and the boundary condition comprises a discrete interface between the alternating regions.

An exemplary surface property is selected from the group consisting of elasticity, surface roughness and surface topography. In some cases, the boundary condition is characterized by a difference in the concentration of a composition or substance, e.g., the surface property comprises an ECM protein such as fibronectin or any of those listed above. The periodicity of fibronectin, laminin, collagen, fibrinogen, or any of the boundary compositions described herein, along the length of the surface is between 0.1 µm and 10 µm. The cells are aligned on the surface in the direction perpendicular to the direction of the periodicity.

The methods are used to make a 2-dimensional or a 3-dimensional arranged tissue structure comprised of cells arranged through alignment of a subcellular organelle inside the cell. Tissues such as artificial muscle tissue are produced using the arranged tissue structures. For example, an artificial muscle tissue comprises 10,000, 100,000, or millions of aligned sarcomeric units by which the muscle cells are aligned. Artificial muscle tissue comprised of a plurality of aligned tissue structures (e.g., monolayers) is 0.01, 0.1, 1, 5, 10, 25, 50, or more centimeters in thickness. For example, the muscle tissue is produced by extruding a plurality of structures described above in which cells are further aligned by application of physical, mechanical, e.g., shear, or electromagnetic forces. The characteristics of the muscle, e.g., meat, are determined by the composition(s) which form the basis of the boundary condition. For example, the nutritional quality of the meat is improved by use of a nutritional composition such as omega-3 fatty acids as a boundary condition. Similarly, the meat is altered in quality by use of a pharmaceutical agent. Moreover, the taste, grain, and texture of the meat is altered by the concentration and variation of compositions in the boundary condition.

Artificial muscle tissue is also useful in robotics applications, in the manufacture of prosthetic devices, or any application in which aligned actuators, e.g., sarcomeres, are desired.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Numerous references, including patents, patent applications, and various publications are cited and discussed in the description of this invention. The citation and/or discussion of such references is provided merely to clarify the description of the present invention and is not an admission that any such reference is "prior art" to the present invention. All references cited and discussed in this specification are incorporated herein by reference in their entirety and to the same extent as if each reference was individually incorporated by reference.

International Patent Application WO 2008/051265 is specifically incorporated by reference into this application in its entirety.

Unless defined otherwise, all technical and scientific terms used herein have the same meaning as commonly understood by one of ordinary skill in the art to which this invention belongs. In the case of conflict, the present Specification will control.

DETAILED DESCRIPTION OF THE INVENTION

Figure 1:
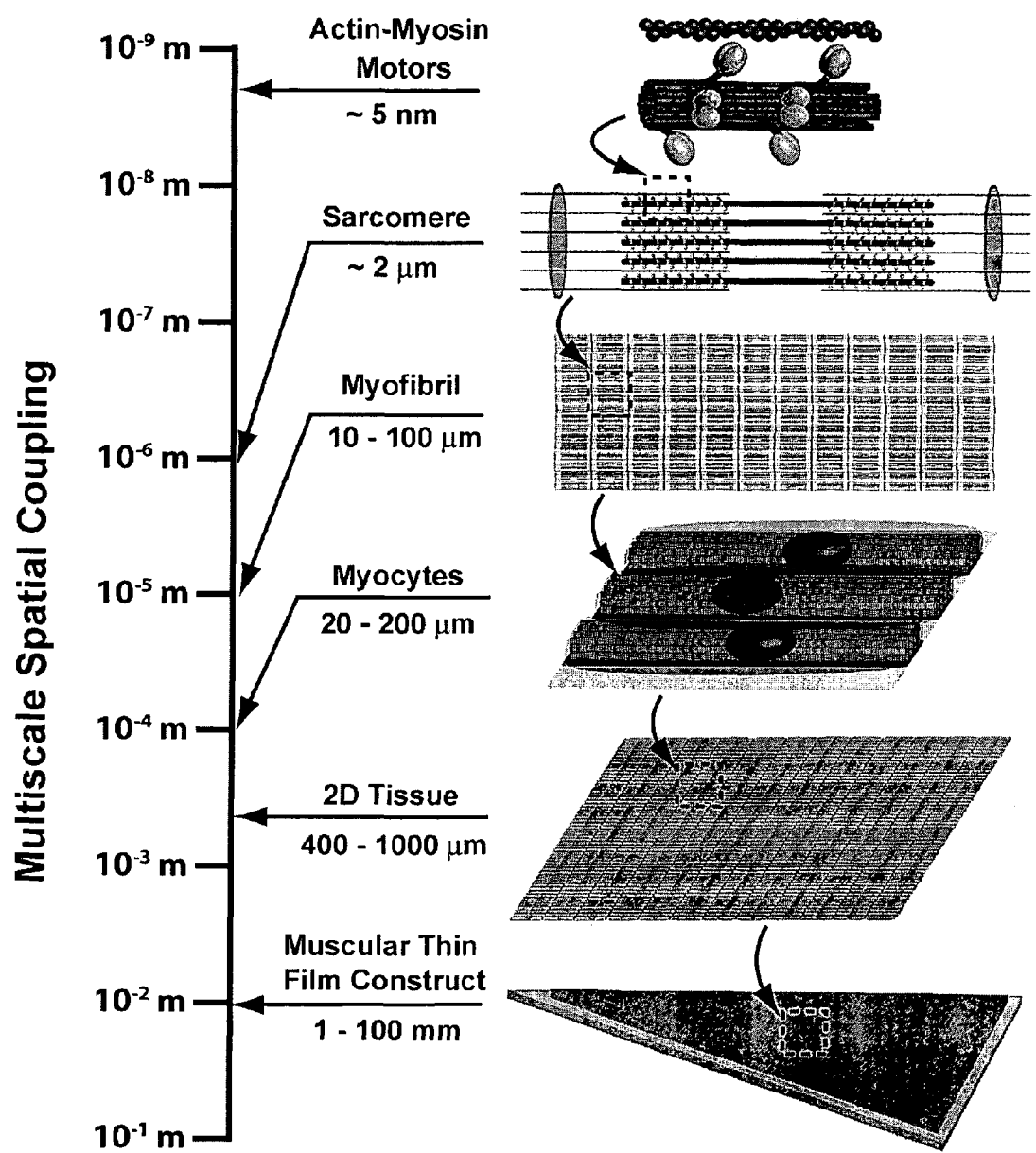
FIG. 1 is a schematic illustration demonstrating a hierarchical, multi-scale coupling of muscle cells into tissues, wherein the use of boundary conditions aligns both individual cells and larger cell ensembles and tissues. Patterning at the 10's of micrometer scale directs downstream sarcomere alignment and upstream tissue assembly. Alignment of myosin motors on actin filaments directs multiscale coupling. Spatial dimensions span 9 orders-of-magnitude from $10^{-9}$ to $10^0$ meters. Forces generated by contraction span 15 order-of-magnitude from $10^{-12}$ to $10^3$ Newtons.
Figure 2:
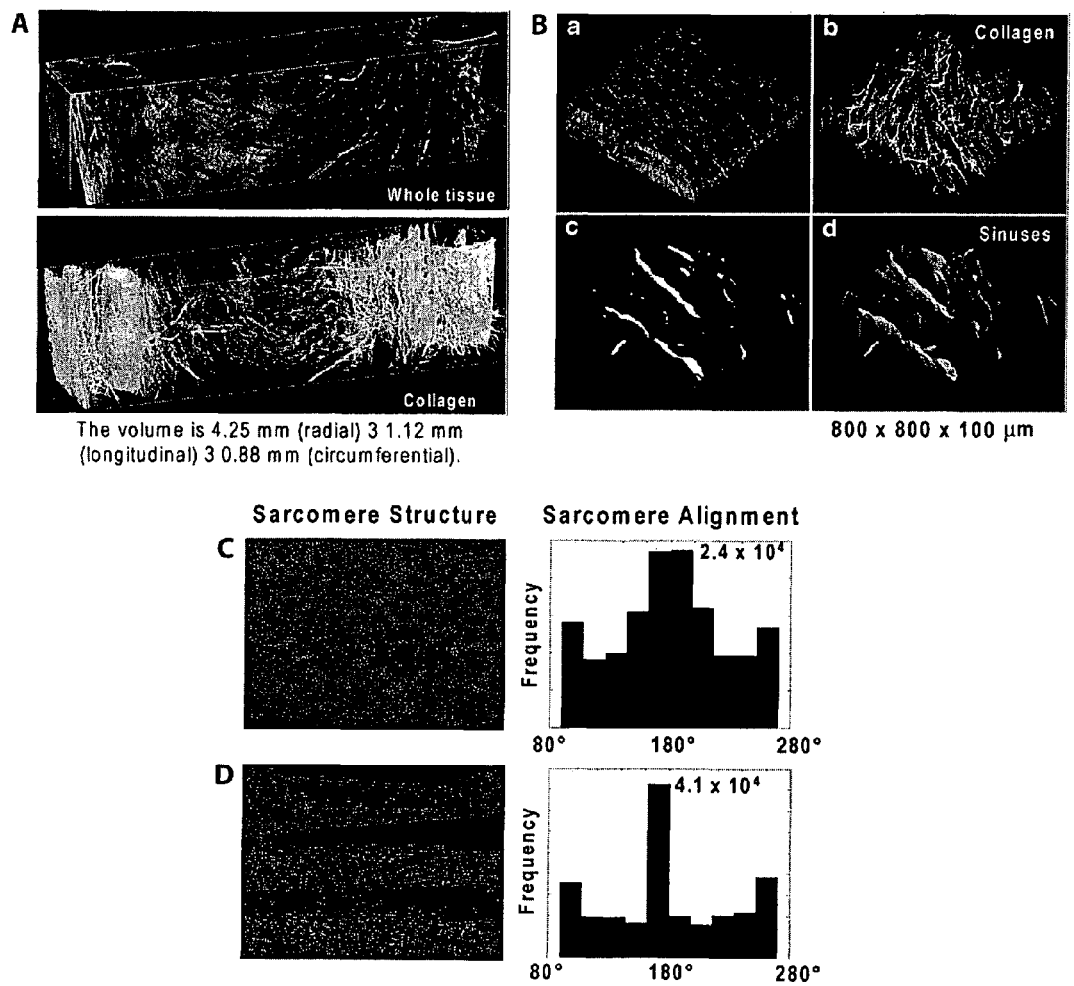
FIG. 2 compares images of native heart muscle that highlight the collagen network and sinuses that act as boundary conditions in the natural heart (Panels A and B), which are complementary to the engineered boundaries in anisotropic two-dimensional tissues (shown in the images in the left box of Panels C and D), where the sarcomere alignment is quantified with image processing software. The histograms in Panels C and D show that the alignment of tissue with discrete boundary conditions is ~75% greater with a narrower distribution. Panel A is from Sands et. al., Microscopy Research And Technique 67:227-239 (2005). Panel B is from Young et. al., Journal of Microscopy, Vol. 192, Pt 2, November 1998, pp. 139-150.
Figure 3:
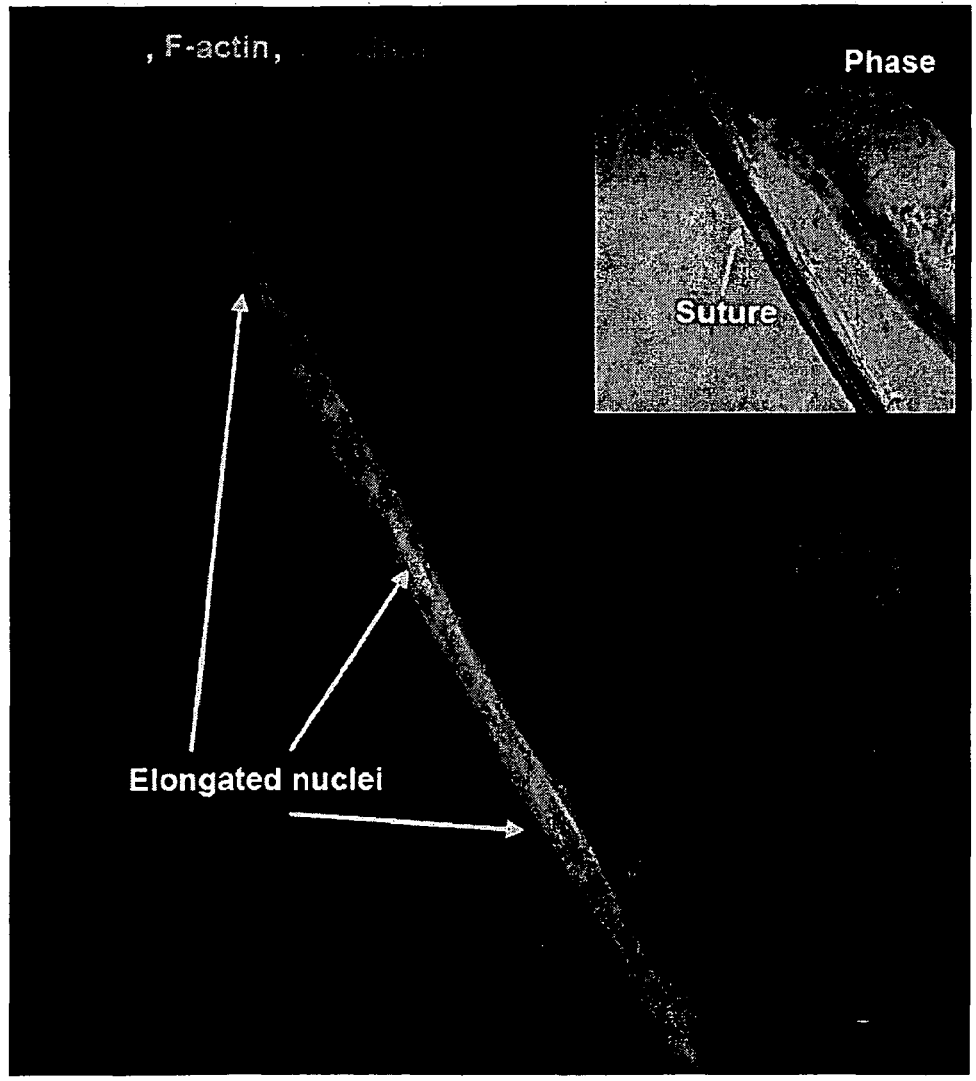
FIG. 3 shows the replication by sutures to impart (in three dimensions) the boundary conditions created by blood vessels in the myocardium to orient myocytes, as is evident by both the elongated nuclei along the suture axis and the corresponding alignment of the sarcomeres. Myocytes adhere to and elongate axially along fibronectin-coated silk sutures; the nuclear shape of the myocytes frequently adopt a high aspect ratio, which differs substantially from that seen in myocytes adhered to flat surfaces.
Figure 4:
FIG. 4 shows an additional example of sutures used as a boundary condition for myocyte alignment. On this larger-diameter suture, the nuclei are not aligned, but the cell body and sarcomeres are still well aligned.
Figure 5:
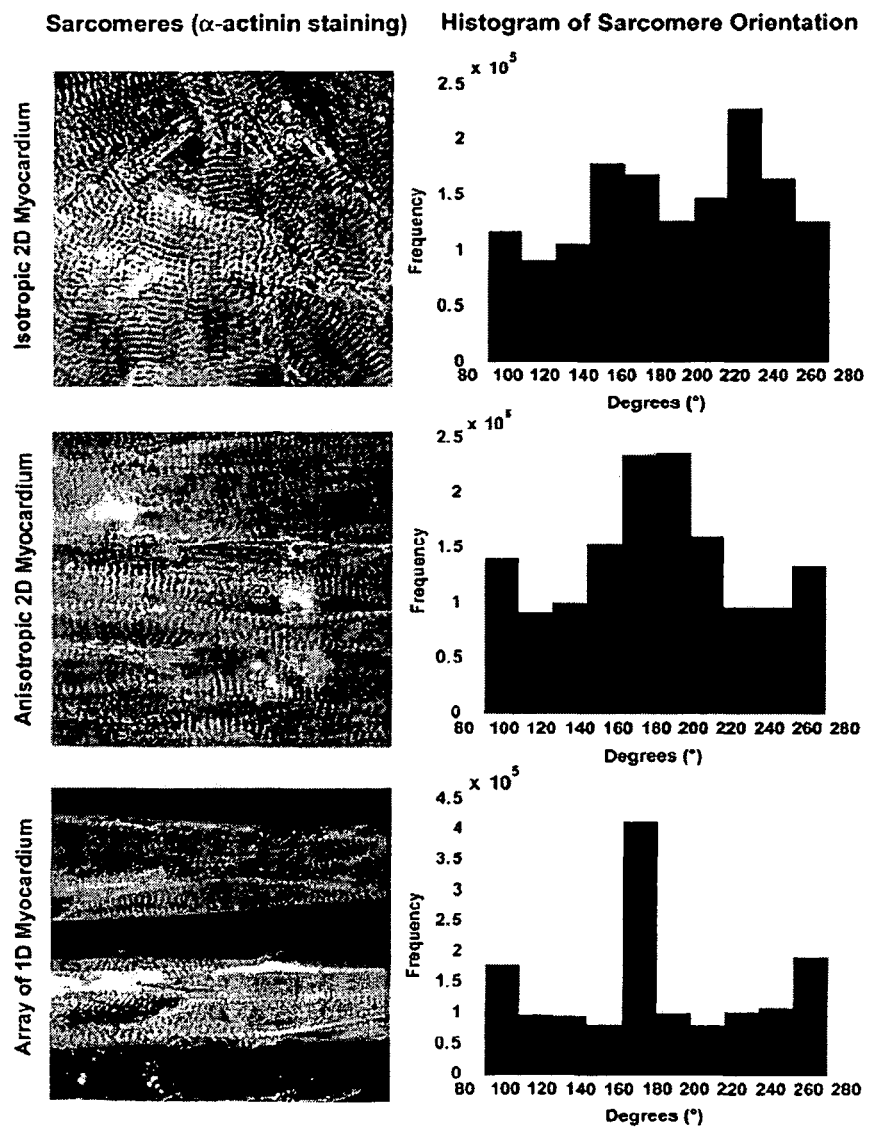
FIG. 5 shows additional examples of two-dimensional cardiomyocytes with engineered tissue microstructure. Cardiomyocytes are fluorescently labeled to visualize the sarcomeres for randomly oriented (top), oriented (middle) and highly-oriented (bottom) tissues. Quantification of sarcomere orientation in the corresponding histograms shows that the introduction of cell-free boundary conditions (bottom) enhances alignment by increasing the total number of aligned sarcomeres and narrowing the spread of orientation angles about the mean.

To "arrange" is to provide some degree of order to a system in which there is some resulting anisotropic property or environment. Such order may be shown through a cell arrangement with a spatial anisotropy in at least one direction.

A "medium" is an environment within which a cell may exist. A "substrate" is a surface environment upon which a cell may exist.

A "boundary condition" is associated with a medium or substrate such that it results in an alteration of a response of a cell when a cell interacts with the boundary condition as compared to when the cell interacts with the medium or substrate alone. A "boundary condition" is also a change in local environment as compared to the environment of the medium or substrate alone. "Artificially provided" is to be added to a system by non-natural methods.

A "surface feature" is any characteristic on a substrate that is distinguishable from its surroundings. Non-limiting examples include grooves, ridges, roughness, or other forms of topography. Surface features may serve as boundary conditions.

The present invention provides one or more arranged cells and methods to arrange cells based on the use of boundary conditions. Boundary conditions may include anisotropic spatial structures. For example, in the native heart, anisotropic spatial structures include cartilage, blood vessels, lymphatic vessels, sinuses, extracellular matrix protein fibrils (collagens, fibronectin, laminin, etc.), and non-muscle cells (fibroblasts, myofibroblasts, etc.). In in vitro systems, these anisotropic spatial structures include culture surfaces, patterned regions of non-adhesive surface chemistry (for example, polyethylene glycol or bovine serum albumin), discrete changes in surface chemistry (for example, protein type, density, activity, etc.), surface topography, sutures and synthetic or natural fibers or fibrils. To enhance muscle generation, these cues can be combined with additional methodologies, including electric fields, mechanical stimulation and pharmaceuticals.

The methodologies described herein represent a shift in the design strategy for engineered tissues. For example, a capillary bed and vascular system provide mass transport of nutrients and waste (metabolites) in tissues thicker than about 100 µm (the diffusion limit of $O_2$). The capillary bed is rarely considered important beyond this context. However, in striated muscle, the capillary bed (i.e., small blood filled vessels having a diameter of about 10 µm) is predominantly aligned along the direction of muscle contraction. Thus, the blood vessels directly abut the muscle cells and serve to guide alignment of muscle contraction. Instead of orienting muscle cells directly, the capillary bed and the corresponding nutrient gradient is engineered into an anisotropic structure that induces muscle alignment. There are many other examples of non-muscle structures that can also direct alignment, including the collagen fibrillar network, fluid-filled sinuses and non-muscle cells (such as fibroblasts, smooth muscle cells and myofibroblasts). Accordingly, the enhanced alignment of a capillary bed is mimicked using engineered boundary conditions, and the generation of structures on size scales similar to those of capillaries, collagen fibrils and other cells has been shown to increase myofibrillar alignment.

The methodology of the present invention is also applicable to other tissue and organ systems. In many specialized tissues, such as muscle, the critical role of minority cell types and extracellular structures has been ignored or minimized. The example provided for cardiac muscle is also applicable to skeletal muscle, where many of the same principles hold. In addition, in skeletal muscle, the interface with tendons and other connective tissues indicates a greater role for the extracellular matrix and cells, such as fibroblasts and chondrocytes.

Spinal-cord repair represents an example where the engineered-boundary-condition methodology enhances nerve regeneration. In spinal cord injury, nerve regeneration across the lesion is inhibited by the growth of a scar predominantly populated by glial cells. The spinal cord is not vascularized and thus a capillary bed is not present. Rather, there must be other structures that guide and direct the long-distance connections of nerve cells. Nerve re-growth is enhanced by glial cell alignment, extracellular matrix structure and/or growth factor gradients. Bone regeneration is another example where engineered boundary conditions are applicable.

Boundary Conditions

Boundary conditions may be linear or non-linear and may be in two or three dimensions. Boundary conditions on a surface is an example of a two dimensional system whereas boundary conditions spread throughout a cell culture medium is an example of a three dimensional system.

Changes in Local Environment

Non-limiting examples of changes in a local environment that can serve as boundary conditions, and ways to define them, are outlined below.

The "sharpness" of the boundary can be defined as the gradient, i.e., the rate of change of a given property's magnitude as a function of distance. For tissue engineering and cell culture, this gradient can be a physical, chemical or mechanical property, chemical species, or electrical or magnetic field. For example, the concentration of an ECM protein or other compositions is at least 5-10 times different in a given area compared to an immediately adjacent area to function as an effective boundary cue.

Boundary conditions may be physical. Non-limiting examples of physical boundaries include culture substrates. These substrates can be any rigid or semi-rigid material such as metals, ceramics or polymers. Other physical substrates include fibers. These can be made of polymers that may be biological or synthetic in composition and may be permanent or resorbable and may also include ceramics such as bioglasses or metals such as stainless steel or titanium. Specific non-limiting examples include sutures, hairs, threads, or fibrils. Fibers can exist individually or be woven, knit, or associated into more complex structures. Synthetic fiber materials include, but are not limited to, polyethylene, polyethylene terephthalate, expanded polytetrafluoroethylene, poly lactic acid (PLA), poly glycolic acid (PGA), PGA/PLA copolymers, polyvinyl alcohol and other thermosets, thermoplastic elastomers, ionically or covalently crosslinked elastomers, hydrogels, thermoplastics, etc. Biological fiber materials include, but are not limited to, extracellular matrix proteins, including but not limited to collagens, fibronectin, laminin, vitronectin, fibrinogen, fibrin, etc. Fabrication methods for the fibers include, but are not limited to, electrospinning, extrusion, spraying or microfabrication. Further non-limiting examples of boundary conditions include interfaces, such as solid/liquid (non-limiting examples include blood vessels and sinuses, microfluidic channels or tubes) or liquid/gas (non-limiting examples include alveoli, sinuses, or gas bubbles). Other physical boundary conditions include micro and nano scale topography, such as micro/nano fabricated ridges, pillars, grooves and other structures or etched surfaces with micro/nano scale roughness.

Differing properties of a local environment may serve as boundary conditions as outlined below.

Surface Energy/Interfacial Energy

Relative changes in hydrophilicity/hydrophobicity (surface energy) can be used to form boundary conditions. Surface energy is related to a surface's susceptibility to wetting and can be measured in ergs/cm$^2$. Interfacial energy is the energy between two surfaces such as a cell and a surface. Two materials with low interfacial energy are inclined to wet.

Patterned surface chemistry controls how and where proteins adsorb to a surface. Once exposed to a physiologic fluid, nearly all surfaces will become fouled with a protein layer. Protein adsorption makes surfaces relatively hydrophilic and readily wetted. Surfaces that are very hydrophilic to begin with, such as polyethylene glycol (for example, the PEG based polymer Pluronics), are so hydrated with water that proteins are unable to displace the water and adhere. Very hydrophilic surfaces repel proteins but are readily wetted. As the hydrophobicity of a surface increases, its wettability decreases but its ability to adsorb proteins increases. Once protein is adsorbed, the wettability of the surface is then increased.

Different proteins will have different adhesion kinetics and specificities depending on the amino acid sequence, 3D conformation, and ability to partially denature during adsorption to a surface. Typically, the first protein adsorbed to the surface will block the binding of subsequent proteins and chemicals, which can be used in combination with soft lithography to create highly effective boundary conditions.

Stiffness/Elastic Modulus

The elastic modulus or stiffness of a substrate can act as a boundary condition. Stiffness can be measured in N/m, and the elastic modulus can be measured in Pascals (Pa). Stiffness is the resistance to deflection or deformation by an external force and is proportional to the modulus of elasticity. The elastic modulus, E, of a cell varies from ~1 to 100 kPa depending on the cell type and location on the cell. Because cells exist in tissues and organs, they are responsive to a range of similar elastic moduli but also respond to stiffer materials such as bone. Thus, cells in general seem to be able to differentiate materials with elastic moduli between ~1 kPa and 1 GPa. Below this range materials are typically more like liquid while above this range materials are so stiff that cells can not differentiate them.

For engineered boundary conditions, a range of elastic modulus from 1 kPa to 1 GPa can be used to tailor cell response (elastic modulus may be greater than 1 GPa, but cell response is not further altered). Boundaries can either be discrete or gradual, producing different effects. For example, a surface such as tissue culture grade polystyrene (E~3 GPa) can have the surface modified to be an array of microridges (e.g., 10 µm wide, 10 µm spaced, 10 µm high). The spaces in-between the microridges can be backfilled with polydimethylsiloxane (E~1 MPa) creating an alternating high/low elastic modulus surface. These sharp interfaces (like a square wave of elasticity) will direct cells to grow along the microridges. Whether cells prefer to grow on the polydimethylsiloxane, polystyrene, or the interface between the two will depend strongly on the cell type, different surface chemistries (if they exist) and other conditions such as cell activation/gene expression.

Another option is more gradual changes between surface elastic modulus. For example, polyacrylamide hydrogels can have elastic moduli that range from ~1 kPa to 100 kPa depending on the cross-link density. If the cross-linker is photoactive, then a special grayscale photomask can be used where the transparency gradually changes from 100% to 0% in a sinusoidal or similar pattern, where peak-to-peak change of opacity are in the range of 1 to 100 µm. Exposure of the polyacrylamide gel with photo cross-linker to UV light through this mask will create a surface with varying elastic modulus, the variation will depend on the cross-linker density, the intensity of UV light and the exposure length. Once again, cells will align parallel to the microridges with cell preference for a specific elastic modulus depending on a variety of factors including cell type, as noted above.

Elastic modulus ranges useful for arrangement of cells is from 1 kPa to 1 GPa (or greater, but cells will not be able to tell the difference). Spacing of elastic modulus domains from 1 to 100 µm can be used to control tissue alignment at the microscale. Larger scale tissue control will require large spatial domains. Transition between elastic modulus domains is either discrete (as in an interface between a stiff and hard material) or gradual (as in a variation of cross-link density over a given distance).

Viscoelasticity

Most of biology is viscoelastic, so whether a material behaves elastically and springs back or responds viscously and flows depends on the force loading rate. Viscoelasticity can be engineered to create boundary conditions. This property becomes relevant when the rate at which cell/tissue moves (such as muscle contraction) causes one component to behave elastically while another behaves plastically. Delineation of viscoelasticity parameters may be complicated by the remodeling that biological systems undergo due to applied forces, making it difficult to differentiate what is plastic deformation in a traditional 'materials' definition and what is due to active/activated changes in the cells and/or extracellular matrix.

Biological materials are capable of plastic deformation from ~0% upwards of 100% depending on the tissue/cell type. However, because these are viscoelastic materials the strain depends on the loading rate, which for biological systems can vary from $10^{-12}$ to >1 Newtons over time scales from $10^{-7}$ to $10^3$ seconds.

Surface Roughness

Surface roughness can be used to generate boundary conditions. Much like the elastic modulus, the transition between domains may be discrete or gradual. Gradient steepness can also affect alignment, with steeper gradients typically producing great alignment.

The scale of the roughness relative to the cell dimensions is important. Microdomains of surface roughness can be generated by selectively dry or wet etching different regions of a polymer, metal or ceramic surface. There are many other ways known in the art to create different microdomains of surface roughness including physical scratching such as with sand paper, curing polymers against rough surfaces, ablation with a beam (laser, ion, electron, etc.), phase separation of copolymers/multi-component polymers, etc. Some magnitudes of roughness will enhance cell adhesion and others will decrease cell adhesion, with the type and degree of response depending on the specific cell type.

Roughness is quantifiable, one common metric is the root mean square (RMS) roughness. The RMS roughness can be random (isotropic) with no long range order or can result from a highly structured surface such as microtopographies (such as microridges) or nanotopographies (such as phase separated polymer surfaces, as with styrene-butadiene-styrene tri-block co-polymers). The roughness can span from RMS roughness values of 1 nm to 1000 µm. Above this range, roughness will not direct cell growth and alignment, but may affect macroscale tissue properties. Different roughness scales will be effective for different cell types, for example endothelial cells respond to microridges 5 µm wide, 5 µm high and 5 µm spaced by aligning strongly to the ridges.

Electrical Resistivity and Thermal Conductivity

Anisotropy of these properties in the scaffold structure is also important. Thus, an interface between two materials with dissimilar thermal conductivities will act as a boundary condition. Depending on the temperature of the materials relative to the cell, the material with higher thermal conductivity will heat or cool the cell more rapidly than the material with lower thermal conductivity. An order of magnitude difference would likely be perceived by the cell; specifically the cell should be most sensitive to a range of thermal conductivity near its normal environment, the thermal conductivity of physiologic salt solution. Cells should be most sensitive to materials that deviate from its normal environment, the resistivity/conductivity of physiologic salt solution. Electrical resistivity can be measured in ohms and thermal conductivity can be measured in W/(m·K). Cells will align to electrical gradients and/or migrate along thermal gradients.

Electrical and/or Magnetic Fields

Boundary conditions can also be generated using electrical and/or magnetic fields. Cells will align to electrical fields as has been shown for cardiomyocytes. In addition to simple field gradients, these fields can also be 'patterned' by engineering the size, spacing, spatial configuration and bias across electrodes or electrode arrays. Cells that respond to the electrical field include cardiomyocytes and neurons. Also, the use of electrical fields to accelerate healing in sports injury suggests that many other cells types will also respond.

Chemical or Biochemical

Boundary conditions may be chemical or biochemical, for example as applied to physical surfaces in specific patterns for additional functionality. These boundary conditions may include extracellular matrix proteins including, but not limited to, collagens, fibronectin, laminin, vitronectin, fibrinogen, or fibrin; surface oxidation; selective deposition of protein resistant polymers such as polyethylene glycol and its derivatives; growth factors including, but not limited to, transforming growth factor beta (TGF-B), granulocyte-colony stimulating factor (G-CSF), granulocyte-macrophage colony stimulating factor (GM-CSF), nerve growth factor (NGF), neurotrophins, platelet-derived growth factor (PDGF), erythropoietin (EPO), thrombopoietin (TPO), myostatin (GDF-8), growth differentiation factor-9 (GDF9), basic fibroblast growth factor (bFGF or FGF2), epidermal growth factor (EGF), hepatocyte growth factor (HGF); cytokines including, but not limited to, chemokines (C, CC, CXC and $CX_3C$ subtypes), adipokines (leptin, adiponectin, resistin, plasminogen activator inhibitor-1 (PAI-1), tumor necrosis factor-alpha (TNF-α), interleukins, or interferon.

Boundary conditions may include biological structures. Non-limiting examples of biological structures include blood vessels (from capillaries up to large caliber veins and arteries), extracellular matrix protein fibrillar networks (composed of collagen, fibronectin and/or lamin), basement membranes (for epithelial and endothelial tissues), internal elastic lamina (vascular), fascia (superficial, deep and visceral types), lymphatic vessels, bone, or cartilage.

Cell and Cell Responses

Boundary conditions affect the behavior of a cell interacting with the boundary condition as compared to interacting with the medium or substrate alone. Different cell types will respond differently to the same boundary condition. Also, different cell types will respond differently to a change in a given boundary condition. In the literature there are many examples of biochemical gradients controlling cell migration, substrate stiffness gradient controlling cell migration, etc. However, there is no discussion of how these boundary conditions are critical to tissue assembly and function.

Any cell type that exhibits an alteration in behavior in response to a boundary condition associated with a medium or substrate as compared to its behavior with the medium or substrate alone may be used in accord with the present invention. Non-limiting examples of cell types include striated muscle cells, fibroblasts, myofibroblasts, chondrocytes, smooth muscle cells, or glial cells.

The "sharpness" of a boundary may be defined through the reaction of a cell with the boundary condition. For example, a sharp boundary condition may induce a cell to cease growth or advancement. A boundary that is not sharp may induce a cell to slow growth, such as when there is a broad chemical gradient. Both conditions may induce a cell to change its direction of growth or movement, where a sharp boundary will likely cause a faster response.

Non-limiting examples of alteration in cell behavior that can serve to define a boundary condition include an up- or down-regulation of a cell motility pathway, a re-arrangement of cytoskeleton at the locus of cell growth, a change in the direction of growth or movement of a cell, a change in the rate of cell growth or movement, a cessation of growth or movement, or apoptosis or necrosis of a cell upon encountering a boundary condition.

Applications

The potential applications of this fabrication protocol are widespread. For example, understanding and proper implementation of muscle-tissue engineering scaffolds with the appropriate hierarchical, multiscale design can result in vastly superior muscle function. Specifically, this approach can ensure uniaxial contraction of muscle, spanning from the single cell to the muscle bundle to the whole muscle. Further non-limiting examples of applications include alignment of striated muscle cells in cardiac and skeletal muscle; guidance of nerves in spinal cord repair across the lesion; guidance of nerves in peripheral nerve repair; endothelialization of artificial vascular grafts, tissue engineered vascular grafts, stents, arteriovenous fistulas, artificial heart valves and xenograft heart valves; and alignment of chondrocytes for cartilage repair in rhinoplasty and other cosmetic/reconstructive procedures. Additional non-limiting examples of applications include alignment of tendon derived cells for repair of sports related injuries, tendonitis, etc.; alignment of ligament derived cells for repair of ligaments throughout the body such the anterior cruciate ligament (ACL), lateral collateral ligament (LCL) and posterior cruciate ligament (PCL) that often tear in sports related injuries; alignment of osteoblasts and osteoclasts for bone regeneration and function, critical to enabling bones' roles providing protection, shape, blood production, mineral storage, movement, acid-base balance, detoxification and sound transduction.

Figure 19:
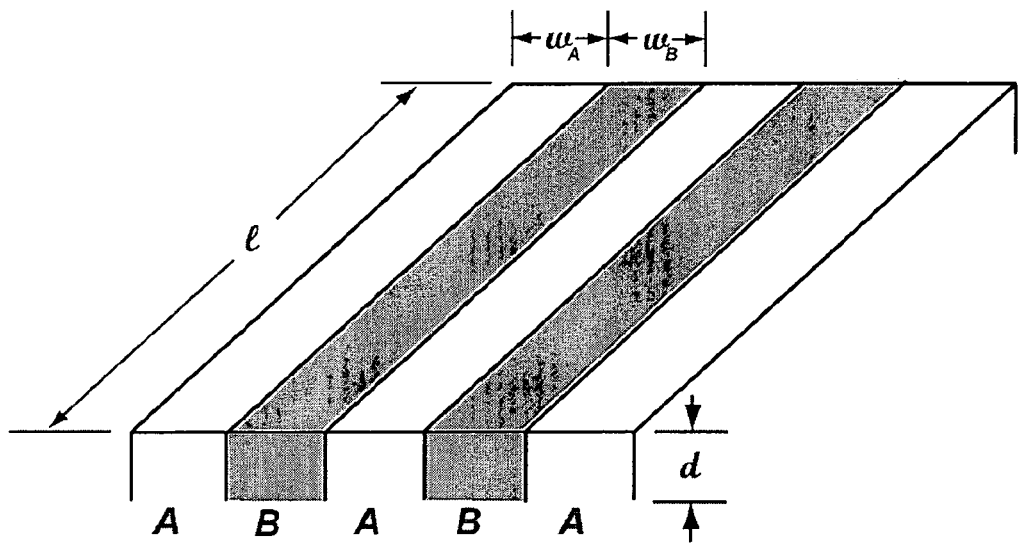
FIG. 19 is a schematic of the boundary conditions used to align cells, e.g., muscle cells, into functional tissues, e.g., striated or smooth muscle, according to some embodiments of the present invention. A substrate with alternating regions A and B is depicted. These regions represent 'high' and 'low' levels of a surface property, and the boundary condition is the interface between these alternating regions. The lateral width of the A and B regions, $w_A$ and $w_B$, define the spacing of the boundary conditions at the interface between the different regions. The length and depth of the regions are l and d, respectively.

FIG. 19 is a schematic of boundary conditions used to align cells, e.g., muscle cells, into functional tissues, e.g., striated or smooth muscle, according to some embodiments of the present invention. A substrate with alternating regions A and B is depicted. These regions represent 'high' and 'low' levels of a surface property, and the boundary condition is the interface between these alternating regions. The lateral width of the A and B regions, $w_A$ and $w_B$, define the spacing of the boundary conditions at the interface between the different regions. The length and depth of the regions are l and d, respectively.

While a binary system is exemplified, three or more regions are also envisioned, e.g., there may also be C, D, E . . . regions. Furthermore, while a surface is depicted, a similar environment can be created in 3-dimensions, e.g., a 3-dimensional gel with embedded cells where the stiffness changes between regions.

Through cell-cell coupling created by the boundary conditions, macroscale assembly of cells into a tissue will generally occur along the longitudinal length l. Therefore, l will generally have dimensions of many cell lengths or longer. As a result, l will typically span from 100 µm to meter lengths. For example, for muscle cells, the length of the regions l will usually be >250 µm.

By contrast, intra-cell alignment of cell bodies guided by the boundary conditions will generally occur along the lateral width of the regions. Therefore, the width of the regions will have dimensions on the order of the width of the cells or organelles, e.g., sarcomeres, being aligned. As a result, when cells are being aligned the widths will typically span from 5 µm to 100 µm lengths. However, when one of the surfaces, e.g., B, does not permit cells on its surface then the corresponding width, e.g., $w_B$, can span a larger range, such as 0.1 µm to 1000 µm. Similarly, when organelles are being aligned, e.g., when boundary conditions guide the intra-cell alignment of contractile organelles (i.e., sarcomeres) by aligning the focal adhesions to the extracellular matrix, the widths will typically be smaller than the width of the cell. In this case, the width of the regions will be approximately the width of a focal adhesion, i.e., between 0.05 µm and 5 µm. In this example, $w_B$ will be still be between 0.05 µm and 5 µm, even if B does not permit cells on its surface.

The depth, d, of the regions will depend on the cell type and surface property type being used to direct alignment. For example, when the surface property is elasticity, elasticity variation must be at least as thick as the cell interfaced with the material and d will be at least 1 μm. By contrast, when the surface is patterned with ECM proteins, d will be typically be 1 to 20 nanometers thick. Furthermore, when surface roughness is used to generate boundary conditions, d will depend on the magnitude of surface roughness. Typically, d will be the same order of magnitude as the surface roughness and will range in value from 1 nm to 10 μm. For physical boundary conditions such as surface topography, d will typically range from 0.1 to 100 μm.

Figure 20:
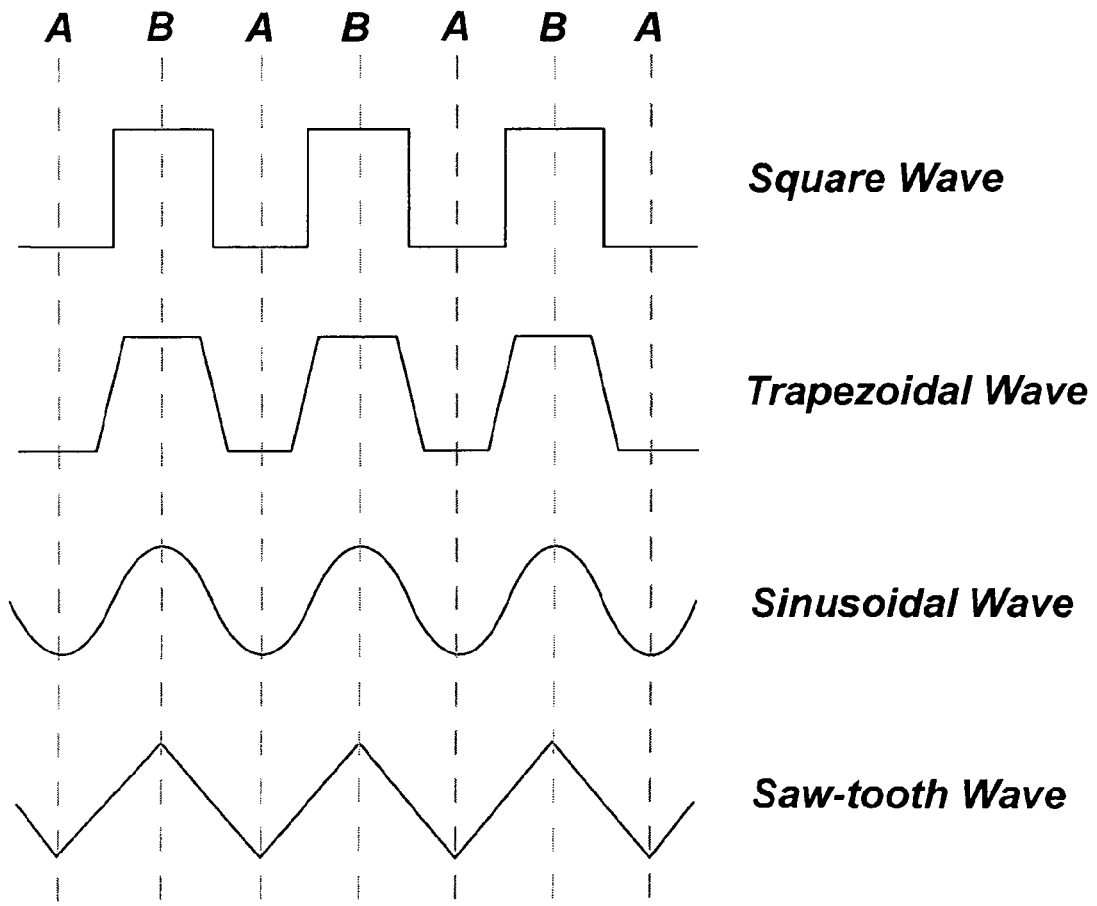
FIG. 20. illustrates examples of transitions between the A and B regions of the embodiments of FIG. 19.

FIG. 20. illustrates examples of transitions between the A and B regions for some of the embodiments of FIG. 19. The 'high' and 'low' conditions are generated using a variety of methods that may lead to discrete (as in an interface) or continuous (as in a gradual variation over a given distance) boundaries between regions. The rate of change at the interface can dictate the effectiveness of the boundary condition and will vary with the type of surface property involved, the cell type and the tissue being generated. For example, square waves are effective when the surface property involved is patterning with extracellular matrix proteins, elastic modulus, surface roughness or surface topography.

In particularly preferred embodiments of FIGS. 19 and 20, the alternating surface property is patterning with extracellular matrix (ECM) proteins. ECM proteins, including fibronectin, laminin, fibrinogen, fibrin, collagen type I and fetal bovine serum, have been shown to be effective. The periodicity of the ECM protein along the length of the surface that is typically suitable is between 0.1 μm and 10 μm. A 'high' concentration of fibronectin, laminin, fibrinogen, fibrin that is suitable ranges typically from 10 to 100 μg/mL in solution prior to surface deposition, while a suitable 'high' concentration of collagen type I is an order of magnitude higher. A suitable 'low' concentration of fibronectin, laminin, fibrinogen, fibrin that is suitable ranges typically from 0.01 to 10 μg/mL in solution prior to surface deposition, while a suitable 'low' concentration of collagen type I is an order of magnitude higher. Fetal bovine serum is effective at concentrations from 10% to 100% in solution prior to surface deposition.

EXAMPLES

The present invention is next described by means of the following examples. However, the use of these and other examples anywhere in the specification is illustrative only, and in no way limits the scope and meaning of the invention or of any exemplified form. Likewise, the invention is not limited to any particular preferred embodiments described herein. Indeed, many modifications and variations of the invention may be apparent to those skilled in the art upon reading this specification, and can be made without departing from its spirit and scope. The invention is therefore to be limited only by the terms of the appended claims, along with the full scope of equivalents to which the claims are entitled.

Example 1

Sarcomere Alignment is Regulated by Myocyte Shape

Cardiac organogenesis and pathogenesis are both characterized by changes in myocyte shape, cytoskeletal architecture, and the extracellular matrix (ECM). However, the mechanisms by which the cellular boundary conditions imposed by the ECM influence myocyte shape and myofibrillar patterning are unknown. Geometric cues in the ECM align sarcomeres by directing the actin network orientation.

The shape of cultured neonatal rat ventricular myocytes was altered by varying the cellular boundary conditions via soft lithography. Circular and 2500 μm$^2$ rectangular ECM islands were microcontact printed on rigid substrates; adherent myocytes conformed to the ECM island shape after 48 hours in culture. Myocytes were immunostained against F-actin and sarcomeric α-actinin to visualize their cytoskeleton with fluorescent microscopy. Each immunofluorescence image was spatially registered, normalized and summed over all myocytes to obtain an averaged image.

Myocytes cultured on the ECM islands reorganize their cytoskeleton and myofibrillar arrays with respect to the boundary conditions imposed by the ECM. Circular myocytes do not possess predictable sarcomeric alignment. In contrast, myocytes cultured on 2500 μm$^2$ rectangular ECM patterns with aspect ratios ranging from 1:1 to 7:1 align their sarcomeres in predictable and repeatable patterns based upon highly localized focal adhesion contacts. Averaged α-actinin images revealed invariant sarcomeric registration irrespective of myocyte aspect ratio. Since the sarcomere sub-units possess a fixed length, this indicates that cytoskeleton configuration is length-limited by the extracellular boundary conditions.

These results indicate that modification of the extracellular microenvironment induces dynamic reconfiguring of myocyte shape and intracellular architecture. Furthermore, geometric boundaries such as corners induce localized myofibrillar anisotropy that becomes global as the myocyte aspect ratio increases. These results elucidate the mechanism by which ventricular myocytes have a longitudinal axis that is generally several times longer than its transverse axis.

Myocyte Morphology

Altered myocyte shape is a hallmark of the normal maturation of the heart, as well as its response to pathological conditions. Of particular importance are the morphological changes induced in the ventricles by mechanical and hemodynamic stimuli that result in physiological or maladaptive hypertrophic responses at the cellular level. For a cylindrically-shaped myocyte, these changes are predominantly reflected in the ratio of the cell length to its width. The hypertrophic response associated with athletic training (i.e., physiological hypertrophy) is characterized by a proportional increase of both myocyte length and width. The response to dilated (eccentric) cardiomyopathy, however, leads to sarcomere assembly in series, producing a greater increase in myocyte length as compared to width (A. M. Gerdes et al. (1988) *Lab Invest* 59:857-61; P. Anversa et al. (1983) *Circ Res* 52:57-64). In contrast, during pressure overload (concentric) cardiomyopathy, sarcomeres are assembled in parallel, resulting in an increase in myocyte width (S. H. Smith & S. P. Bishop (1985) 17:1005-11; P. Anversa et al. (1986) *J Amer Coll Cardiol* 7:1140-9). Regardless of the hypertrophic etiology, adaptive and dynamic reorganization of the contractile machinery is concomitant with either normal or pathological myocyte remodeling.

The extracellular matrix (ECM) microenvironment plays a crucial role in governing the morphological response of a myocyte to external perturbation. The physical coupling of the myocyte to the ECM is mediated by transmembrane receptors such as integrins, which further serve to transmit external mechanical forces into the intracellular space (D. Ingber (1991) *Current Opinion in Cell Biology* 3:841-8; M. Brancaccio et al. (2006) *Cardiovasc Res* 70:422-33). Sarcomeres, among other cytoskeletal structures, are capable of utilizing these mechanical signals to direct their assembly and growth (D. G. Simpson et al. (1999) *Circ Res* 85:e59-e69; S. M. Gopalan et al. (2003) *Biotechnol Bioeng* 81:578-87). Actin stress fiber formation subsequently follows the direction of external tension imposed on myocytes in vitro; myocytes recruit focal adhesion complexes (FACs) to regions of high stress and these FACs are in turn connected to newly polymerized actin microfilaments (A. S. Torsoni et al. (2003) *Circ Res* 93:140). These mechanical forces can be transduced into biochemical signals capable of altering protein synthesis and gene transcription (C. A. Maxwell & M. J. Hendzel (2001) *Biochemistry and Cell Biology* 79:267-74), and indeed pathological cardiac hypertrophy provokes reexpression of fetal-type genes ordinarily inactive in the adult heart (I. Komuro & Y. Yazaki (1993) *Annu Rev Physiol* 55:55-75) in addition to sarcomeric reassembly. Conversely, contractile forces intrinsically generated by myocytes are transmitted to the surrounding ECM via costameres, structures physically coupling the sarcolemmal membrane to the peripheral Z-discs (A. M. Samarel (2006) *Am J Physiol Heart Circ Physiol* 289:H2291-H2301).

While the impact of the ECM on cell morphology has been long recognized (P. Weiss & B. Garber (1952) *Proc Natl Acad Sci USA* 38:264-80), recently developed techniques to control ECM deposition create new avenues of research previously unavailable. Custom-designed microcontact printing (µCP) of ECM substrata offers precise control of adherent cell shape and size independent of cell-cell interaction and culture density (R. Singhvi et al. (1994) *Science* 264:696-8). Applying this technique to single fibroblasts and epithelial cells has revealed details of the relationship between cellular function and morphology, e.g., cell spreading and adhesion formation (D. Lehnert et al. (2004) *J Cell Sci* 117:41-52), cell cycle progression (S. Huang et al. (1998) *Mol Biol Cell* 9:3179-93), growth and apoptosis (C. S. Chen et al. (1997) *Science* 276: 1425-8), and lamellipodia extension and cell migration (K. K. Parker et al., (2002) *Faseb J* 16:1195). However, similar studies of single cardiac myocytes has been more limited, especially in light of their higher contractility and distinct architecture as compared to non-muscle cells (M. H. Lu et al. (1992) *J Cell Biol* 117:1007-22; Z. X. Lin et al. (1989) *J Cell Biol* 108:2355-67). Systematic alteration of the ECM microenvironment has been primarily concerned with tissue-level electrophysiology (N. Bursac et al. (2004) *Proc Natl Acad Sci USA* 101:15530-4; S. Rohr et al. (1991) *Circ Res* 68:114-30) and the response to mechanical stretch (D. G. Simpson et al. (1999) *Circ Res* 85:e59-e69; S. M. Gopalan et al. (2003) *Biotechnol Bioeng* 81:578-87; P. Beauchamp et al. (2006) Circ Res 99:1216-24). Spatial cues in the ECM were found to promote sarcomere alignment by changing myocyte shape and hence directing the orientation of the myofibrillar network. µCP was used to create ECM islands to alter the geometric boundary conditions imposed on cultured cardiac myocytes, and by characterizing the organization of both the sarcomeric proteins and focal adhesion proteins the morphological response as a function of myocyte shape was systemically examined.

Microcontact Printing

Polymer stamps designed for microcontact printing were made using standard photolithographic techniques (Y. Xia & G. M. Whitesides (1998) *Annual Review of Materials Science* 28:153-84). Silicon wafers spin coated with a 2 µm layer of SU-8 photoresist (MichroChem Corp, Newton, Mass.) were exposed to UV light through a photolithographic mask, photodegrading SU-8 and leaving a complementary master pattern. µCP designs consisting of circles 26 µm in radius (2123.7 µm$^2$ area) and rectangular shapes with a constant surface area of 2500 µm$^2$ were used to create the ECM islands. A variety of aspect ratios were created for the rectangular shapes: 1:1 (50×50 µm), 2:1 (70.7×35.4 µm), 3:1 (86.6×28.9 µm), 5:1 (111.8×22.3 µm) and 7:1 (132.3×18.9 µm).

Stamps were formed by pouring un-polymerized poly (dimethylsiloxane) (PDMS, Sylgard 184, Dow Corning, Midland, Mich.) over the master. The cured polymer was peeled off forming a complimentary 'stamp' of the surface. Glass coverslips spin-coated with a layer of PDMS were treated in a UVO cleaner (Jelight Company, Inc., Irvine, Calif.) prior to microcontact printing to oxidize the PDMS layer and facilitate the adsorption of fibronectin (FN) onto the stamp. The PDMS stamps were coated with 300 µl, of a 50 µg/mL solution of FN for 1 hour at room temperature, after which the patterned FN was manually stamped onto the coverslips. The coverslip portions not coated with FN were then blocked by immersing them in 1% F127 Pluronic Acid (BASF, Mount Olive, N.J.) for 5 minutes. All stamped coverslips were washed in PBS and then immediately seeded with myocytes.

Myocyte Culture

Cell cultures of neonatal rat ventricular myocytes were prepared from two-day old Sprague-Dawley rats. The isolated tissue was homogenized and washed in HBSS and then digested with trypsin and collagenase for 14 hours at 4° C. with agitation. Isolated myocytes were re-suspended in M199 culture medium supplemented with 10% heat-inactivated Fetal Bovine Serum, 10 mM HEPES, 20 mM glucose, 2 mM L-glutamine, 1.5 µM vitamin B-12, and 50 U/mL penicillin at 37° C. and agitated. Immediately after purification, myocytes were plated on 25 mm diameter PDMS-coated glass coverslips prepared as detailed above and kept in culture at 37° C. with a 5% $CO_2$ atmosphere. Media was changed 24 hours after plating to remove unattached and dead myocytes and every 48 hours afterwards. 100 mM 5-bromo-2-deoxyuridine (BrdU) was added to the culture medium to prevent multiple nucleation.

Immunohistochemistry

Myocytes cultured for 4 days were fixed in a solution of 4% paraformaldehyde and 0.01% Triton X-100 in PBS buffer at 37° C. for 15 minutes and equilibrated to room temperature during incubation. All myocytes were stained with DAPI for chromatin and FITC-phalloidin for F-actin (Alexa 488 Phalloidin, Molecular Probes, Eugene, Oreg.). The myocytes were also incubated with either mouse-derived IgG1 monoclonal primary sarcomeric anti-α-actinin (clone EA-53; Sigma-Aldrich, St. Louis, Mo.) or vinculin (clone hVIN-1; Sigma-Aldrich) antibodies at a dilution of 1:200 and incubated for 1 hour in PBS. Myocytes were then incubated for 1 hour with secondary antibody tetramethylrhodamine-conjugated goat anti-mouse IgG (Alexa Fluor 594, Molecular Probes) at a dilution of 1:200.

Image Acquisition

The patterned myocytes were visualized with a CCD camera (CoolSnap Photometrics, Roper Scientific Inc., Trenton, N.J.) mounted on an inverted microscope (DMI 6000B, Leica Microsystems, Germany). A 63× objective (HCX Plan APO, NA 1.4, Leica) was used for optical recording. The fluorescence recording was performed with a filter set with a bandpass excitation filter (450-490 nm), dichroic mirror (500 nm) and a bandpass emission filter (500-550 nm). Fluorescence was recorded in a format of 1392×1040 pixels (corresponding to 142.68×106.60 µm$^2$).

Myocyte Geometric Registration and Averaging

Image data was taken from those µCP ECM islands containing only a single, mono-nucleated myocyte. Because of inter-myocyte variation of parameters for a given shape, data was transformed to a uniform coordinate system for image processing and analysis. Despite the pre-defined boundary conditions, the symmetry of the chosen geometries (radial symmetry for circles, four-fold symmetry for rectangles) required each myocyte image to be registered according to its shape. The location of the nuclear centroid served as the fiducial marker to register each image, found by segmenting the nucleus from the DAPI fluorescence image via thresholding. Registration was performed for each shape as follows:

(1) Circles: The manually drawn outline of the myocyte was fit to the equation of a circle. The resultant radial coordinate system was (a) translated such that center was located at the origin, (b) scaled such that the radius was 1, and (c) finally rotated around the origin such that centroid of the nucleus lies on the +x-axis.

(2) Rectangles: A rectangle was fit to the manually-selected four corners of the myocyte. The coordinate system was then (a) translated such that center was located at the origin, (b) rotated such that the long edges were parallel to the y-axis, and (c) scaled according to the pre-defined aspect ratio. Since the rectangle can be divided into four identical quadrants, the centroid for any given nucleus may be mapped into one quadrant through a series of reflections around the x- and y-axes. All data is presented in the form of two-dimensional maps as a function of the normalized distances x and y, in the range of $[-\frac{1}{2}, \frac{1}{2}]$ and $[-AR/2, AR/2]$, respectively, where AR is the pre-defined myocyte aspect ratio.

Once each image was registered and normalized, an averaged F-actin and sarcomeric α-actinin image was obtained for each geometric shape using top-hat filtering to remove non-uniform background fluorescence and then calculating the average pixel intensity over all myocyte images for a given shape.

Determination of Actin Orientation and Sarcomere Statistics

The anisotropy of the myofibril network was determined from normalized and registered immunofluorescence actin images. Each image was pre-processed by an edge detection algorithm and then each edge pixel was assigned a value computed as the local tangent angle to the edge segment measured with respect to the y-axis. The angular statistics of these values was taken as a measure of the global anisotropy of the actin fibers; if the myofibrils are parallel to the y-axis, the mean orientation angle will be close to zero with a low angular spread, whereas an isotropic set of myofibrils will have a larger orientation angle and a higher angular spread.

The sarcomere structure was characterized in sarcomeric α-actinin images as a regularly striated pattern of intensity, lending itself well to use of a fast Fourier transform (FFT) to quantitatively calculate the local spatial frequencies. An intensity profile was chosen along a line towards the periphery of the myocyte parallel to the rectangular long axis. To determine the spatial frequency, the profile was detrended and weighted with a Hamming window prior to transformation into the spatial frequency domain by FFT. The spatial frequency at peak power of the first-order harmonic in the spatial frequency domain was obtained, and this value was converted into the spatial domain to yield the sarcomere length.

Statistical Analysis

All measurements are given as mean±SEM. Angular statistical measurements, such as orientation, were evaluated according to a circular distribution as follows:

(1) The circular mean $\bar{\theta}$ (in degrees) of a set of angles $\theta_1 \ldots \theta_n$, is evaluated by calculating $$X = \frac{1}{n}\sum_{i=1}^{n} \cos\theta_i, \quad Y = \frac{1}{n}\sum_{i=1}^{n} \sin\theta_i, \quad R = \sqrt{X^2 + Y^2} \quad (1)$$

to which $\bar{\theta}$ is the solution to the equations $$X = R\cos\bar{\theta}, Y = R\sin\bar{\theta} \quad (2)$$

(2) The circular SEM (in degrees) is calculated as:

$$\sigma = \frac{180°}{\pi}\sqrt{\frac{-2\ln R}{n}} \quad (3)$$

using R as given in (1).

Statistical significance was determined using multiway ANOVA, followed by Tukey's multiple comparison test to determine differences.

Regulation of Myofibrillar Organization

In all patterned and unpatterned myocyte cultures, spontaneously beating myocytes developed well defined and differentiated myofibrils radiating throughout the cytoplasm after 96 hours. Myofibrillar maturity was verified in the myocytes by the presence of striations along the myofibril: the periodically repeating I-bands highlighted by the phalloidin immunofluorescence, with the Z-discs revealed by the sarcomeric α-actinin stains. Whenever myocytes attached to the ECM substrate, whether the substrate was in the form of an island or an expanse of homogeneous ECM with no local boundary, they assembled vinculin focal adhesion complexes (FACs) and subsequently formed myofibrils with the terminal ends located on a FAC plaque. Myofibrils crossing the medial region of the myocyte to terminate on a FAC had no sarcomeres in the vicinity of the adhesion plaque, as revealed by the α-actinin stains.

Myofibrillogenesis in Unbounded Myocytes

Figure 6:
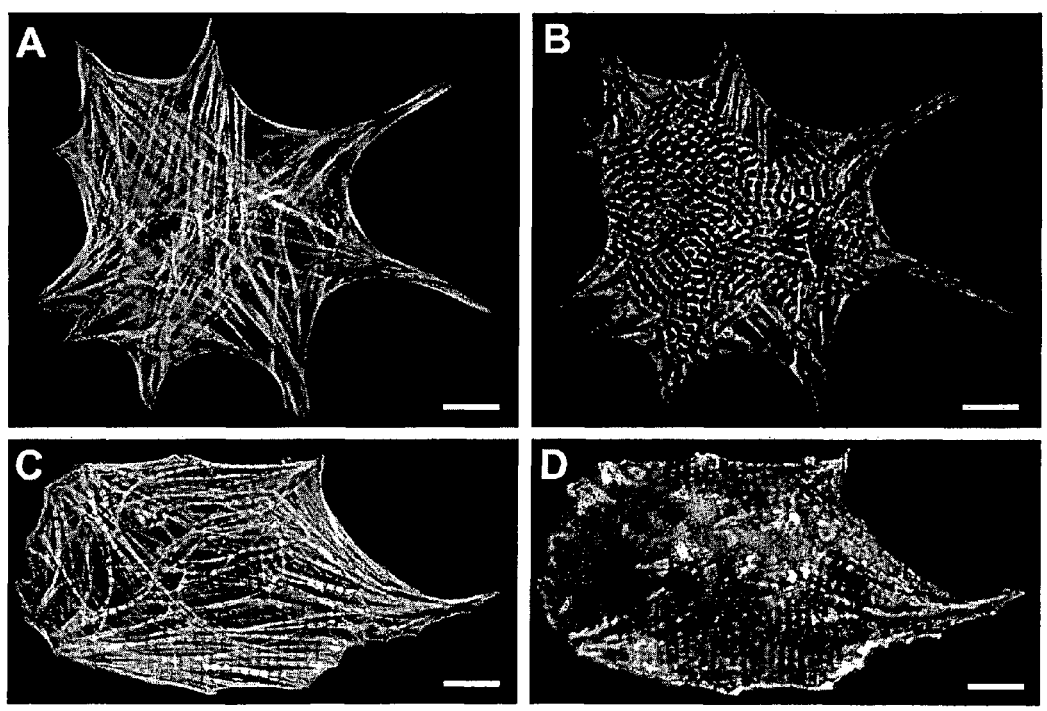
FIG. 6 shows the distribution of actin (A,C) α-actinin (B) and vinculin (D) in pleomorphic cultured myocytes. One myocyte is shown in (A) and (B), and a different myocyte is shown in (C) and (D). Note the lack of myofibrillar and sarcomeric organization and multiple myofibril axes for both myocytes shown. Scale bar: 10 μm.

Myocytes cultured on substrates with uniform ECM protein distribution were characterized by heterogeneous myofibrillar organization (FIG. 6). Such morphology is consistent with the absence of spatial constraints in the local ECM topology, resulting in myocytes of varying shape and size. These pleomorphic myocytes exhibited no consistency in the membrane boundary morphology, as seen by the differences in shape between the myocytes in FIGS. 6A and C. Despite the absence of specific µCP geometric cues, the pleomorphic myocytes were often characterized by extensions of varied number, shape and length.

The sarcomeric organization of the pleomorphic myocytes reflected the myofibrillar orientation: Z-discs were spatially registered in parallel in local sub-cellular domains, especially in the vicinity of acute angles in the membrane boundary. Myofibrils in neighboring domains, however, were often aligned along different axes, producing a lack of global anisotropy (FIG. 6B). The FACs revealed by vinculin were often restricted to the periphery of the myocyte. In many myocytes, vinculin manifested as a punctate pattern co-localized to the myofibril Z-discs, indicating the formation of costameres (B. A. Danowski et al. (1992) *J Cell Biol* 118: 1411-20). For those myocytes with elongated extensions, the FACs were significantly larger in size and possessed a radiating pattern directed inwards from the terminus of the pointed extension towards the myocyte center (FIG. 6D).

Myofibrillogenesis in Circular Myocytes

Figure 7:
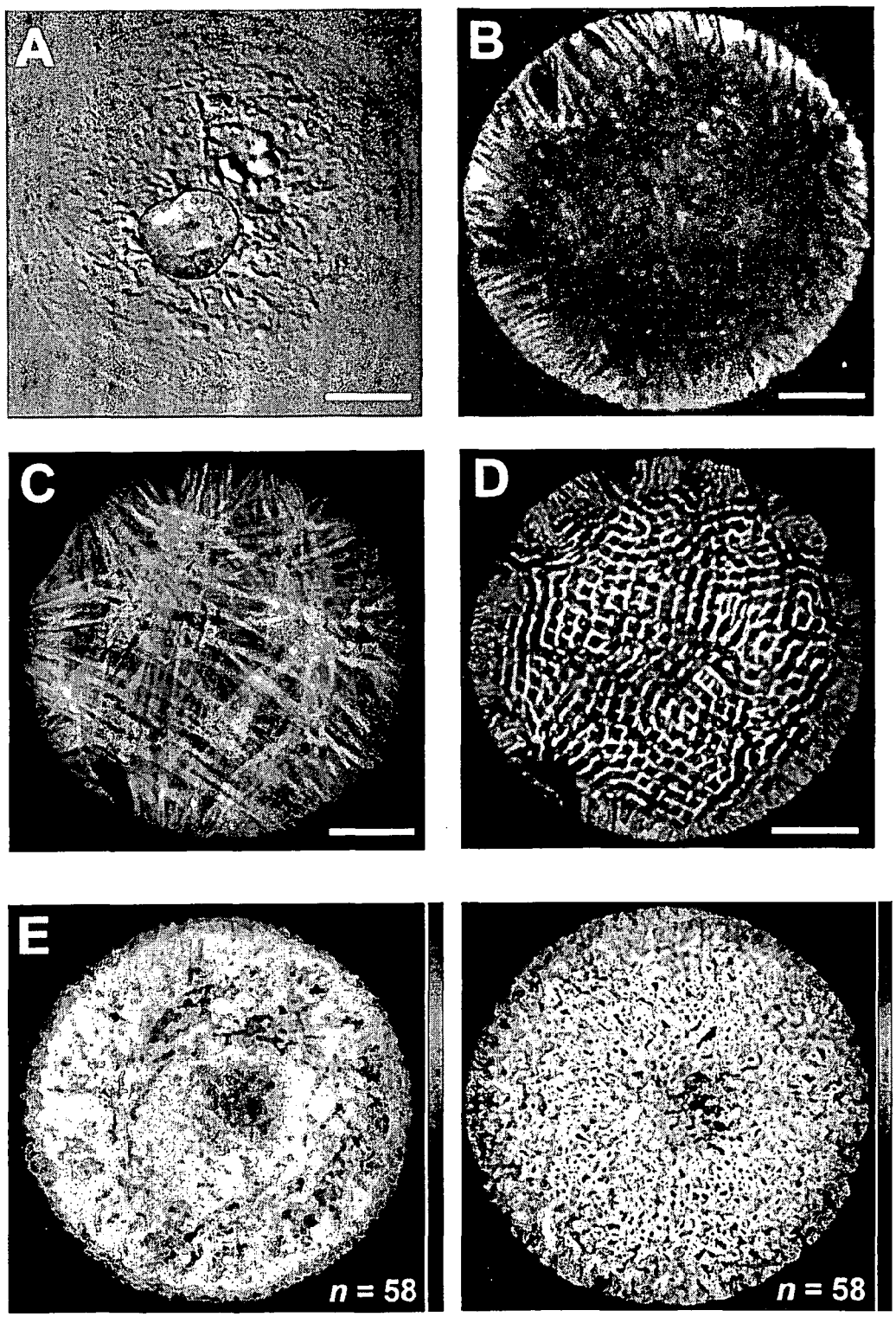
FIG. 7: (A) A DIC (differential interference contrast) image of a cultured myocyte on a microcontact printed circular ECM (extracellular matrix) island (radius: 26 μm) with the nucleus highlighted. (B) Focal adhesion complexes linking the myocyte to the ECM are highlighted by stained vinculin. The associated F-actin (C) and sarcomeric α-actinin in the representative circular myocyte shows the absence of a preferential axis of organization. The resultant sarcomere organization for an ensemble of circular myocytes is illustrated via averaged images of F-actin (C) and sarcomeric α-actinin (D) distributions from fixed and stained myocytes. Scale bars: 10 μm.

The myofibrillar organization associated with myocytes cultured on µCP ECM circles possessed no readily discernable pattern. The FACs reflected this myofibril arrangement by the accumulation of vinculin on the myocyte circumference and distributed as punctuated foci radiating a short distance into the myocyte interior (FIG. 7B). Not all myofibrils spanned the full diameter of the myocyte; many of the myofibrils traversed a shorter chord connecting two points on the myocyte circumference. Furthermore, myofibrils often did not form a straight filament spanning distal points on the myocyte but instead arced laterally across the diameter, sometimes bending around the perinuclear region. This heterogeneous myofibrillar distribution was apparent in the averaged actin images, in which no pattern is readily discernable (FIG. 7C). The average actin density is significantly lower towards the center of the myocyte; this void coincides with the distribution of the nuclei in the circular myocytes, thereby reflecting the displacement of the myofibrils around the nucleus. In accordance with the irregular myofibril arrangement, the Z-disc distribution in circular myocytes is similarly disorganized with no predictable alignment (FIG. 7D).

Myofibrillogenesis in Rectangular Myocytes as a Function of Aspect Ratio

Figure 8:
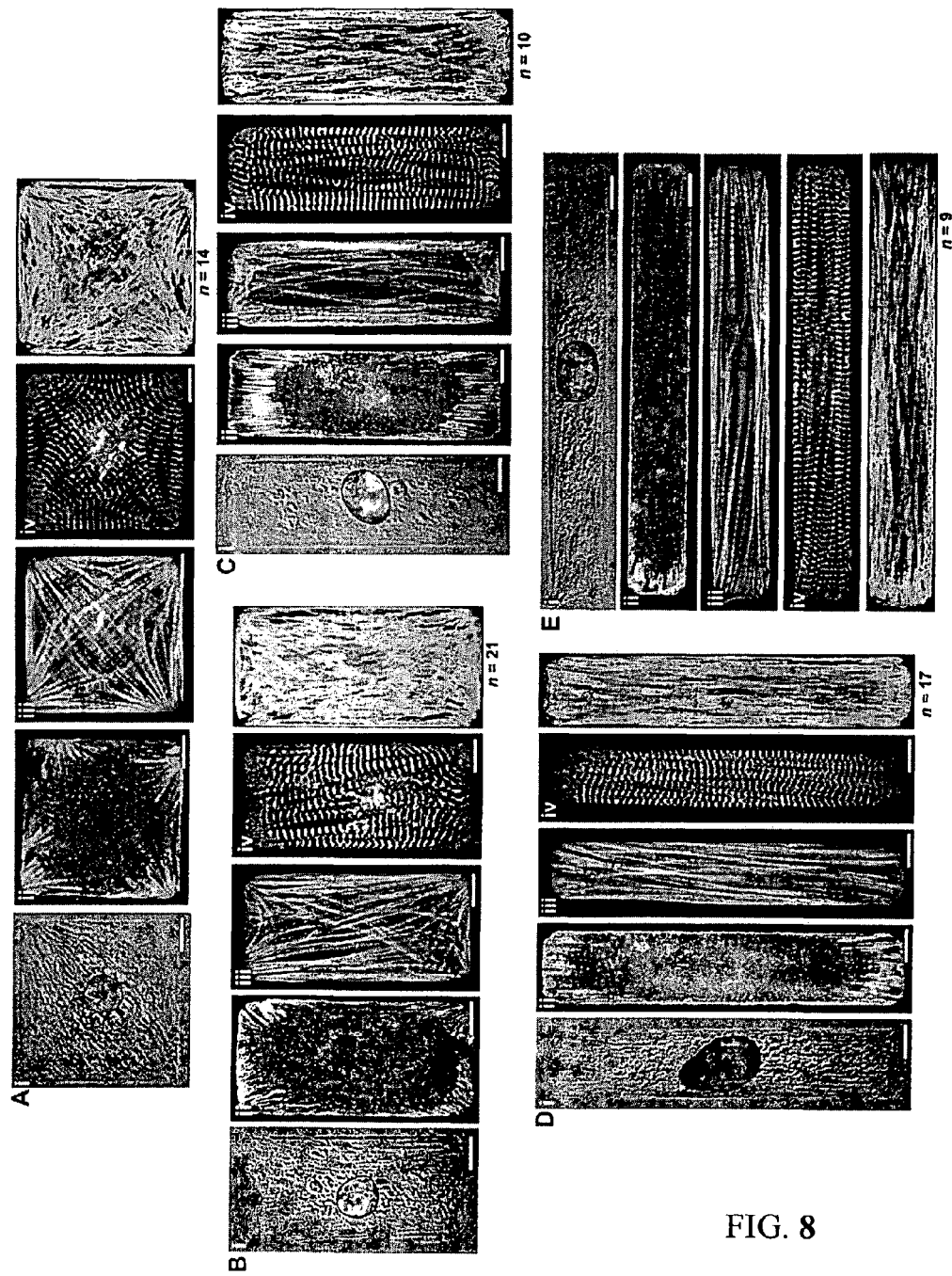
FIG. 8 shows cardiac myocytes on rectangular microcontact printed (μCP) ECM islands, focal adhesion complexes highlighting the myocyte-ECM contacts, and cytoskeletal architecture and averaged myofibrillar organization. Five cellular aspect ratios are shown: (A) 1:1, (B) 2:1, (C) 3:1, (D) 5:1, (E) 7:1. A DIC image and immunofluorescent stains for vinculin, F-actin and sarcomeric α-actinin of a representative cardiac myocyte on a μCP ECM island are shown in panels (i)-(iv), respectively. The averaged distribution of F-actin for each cellular aspect ratio is shown in panel (v).

In contrast to the circular myocytes, the rectangular myocytes displayed a myofibrillar arrangement that was consistent for individual myocytes within each aspect ratio (AR) examined. However, each AR possessed a unique cytoskeletal architecture. Myofibrils in 1:1 myocytes were found to radiate towards the corners of the myocyte, either terminating at a corner along a shared edge, or traversing the myocyte diagonally to terminate at the opposite corner. This myofibril organization was reflected in the vinculin distribution for the 1:1 myocytes, accumulating adhesion plaques in the corner regions of the myocyte where the myofibrils terminated and formed a fan-shaped pattern extending into the myocyte (FIG. 8A ii). Accordingly, the averaged actin distribution showed a similar pattern, with the corners of the myocyte possessing the highest myofibril density; as myofibrils from the medial region of the myocyte terminate on the FACs in the corners, they converged due to their tight packing into a progressively narrower space. Conversely, the averaged actin map revealed that as the myofibrils extend inward from the corners to terminate distally, they preferentially aligned parallel to the myocyte edges rather than the diagonal (FIG. 8A iii).

Figure 9:
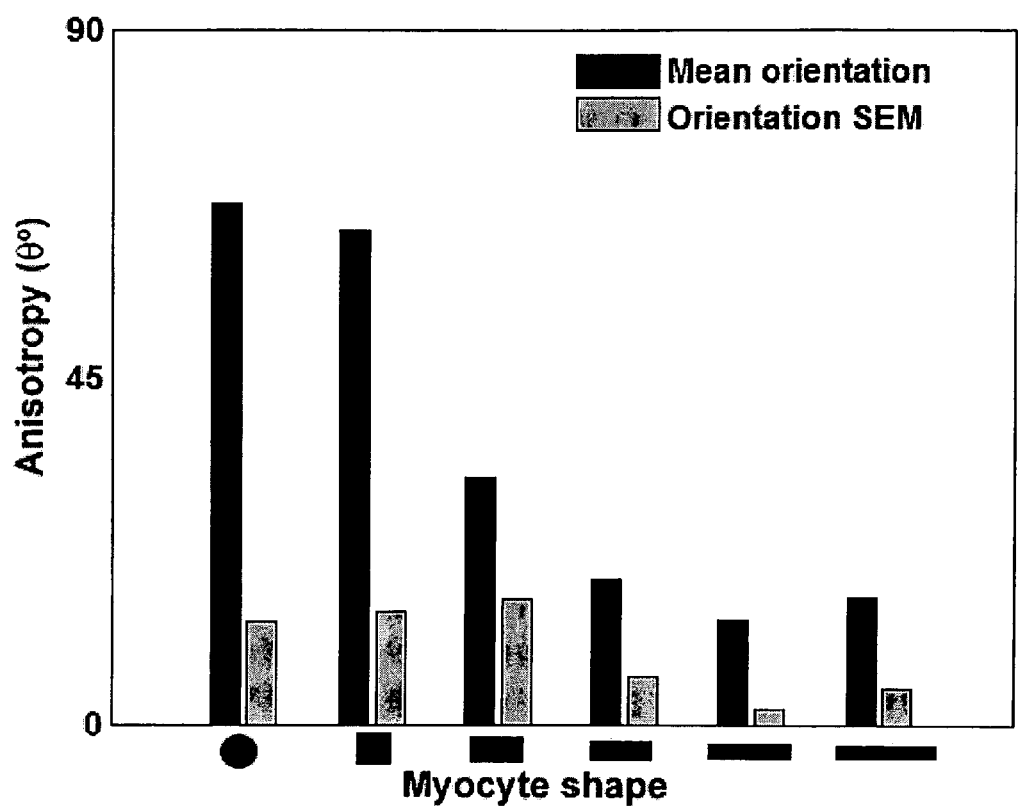
FIG. 9 shows the anisotropy of the myofibrillar network as a function of the myocyte shape, shown as the mean angle (black bar) and angular SEM (scanning electron micrograph) (gray bar) of the actin cytoskeleton with the y-axis.

As myocytes adhered to progressively larger AR µCP ECM islands, myofibril and FAC configurations changed accordingly, as shown in FIG. 8B through E. The FACs for the 2:1 myocytes were primarily restricted to the corners and maintained their fan-shaped morphology as in the 1:1 myocytes but the radiating pattern of the plaques were preferentially oriented parallel to the long axis of the myocytes (FIG. 8B ii). Similarly, the averaged actin distribution for the 2:1 myocytes revealed that while the myofibrils continued to locate their termini in the corners of the myocyte, the myofibrils preferentially spanned the space between FACs in corners on the long axis of the myocyte, and less between the shorter distance between adjacent corners on the short edge or the diagonal on the long axis (FIG. 8Biii). This trend continues for the 3:1, 5:1 and 7:1 rectangular myocytes, with the branches of the FACs of the 7:1 rectangular myocytes aligned strictly parallel to the long cellular axis (FIG. 8Eii). Likewise, the myofibrils were also restricted to the long axis with very few crossing the diagonal to the opposing corner and virtually none branching the short distance to the adjacent corner on the short axis of the myocyte (FIG. 8Eiii). In addition, the averaged actin map indicates that myofibrils oriented along the long axis of the myocyte are primarily located towards the edges, with the myocyte interior possessing a reduced density distribution of myofibrils. These trends were quantified by computing an anisotropy value for each myocyte shape. As shown in FIG. 9, the 1:1 AR and circular myocytes possess comparable myofibrillar anisotropy. However, as the AR for the rectangular myocytes increases, the orientation angle and angular spread concomitantly decrease as the myofibrils become more parallel.

Sarcomere Alignment in Rectangular Myocytes

The averaged α-actinin distribution maps were used to quantify the sarcomere level of the myocyte response to the imposed ECM boundary conditions. For the 1:1 rectangular myocytes, the radial organization of the myofibrils inward from the myocyte corners produced a characteristic moiré pattern in the averaged α-actinin distribution map (FIG. 10A). As the cellular AR was increased, the change in the underlying myofibrillar arrangement from radial to longitudinal was reflected in the averaged α-actinin distribution in which the Z-discs were increasingly oriented perpendicular to the long axis of the myocyte (FIG. 10A). As the myofibrils approached the terminal FACs, the striations often terminated abruptly into non-striated areas with punctuate α-actinin coincident with the adhesion plaques. The co-localization of α-actinin with FACs is consistent with previous observations (L. L. Hilenski et al. (1991) *Cell and Tissue Research* 264: 577-87).

Given the repeatability of myofibril distribution in the shaped myocytes, the question of whether the consistency in myofibril distribution due to µCP ECM shape also leads to predictable sarcomere positioning was addressed. In the averaged images of the sarcomeric α-actinin fluorescence for each shape, shown in FIG. 10A, striations are visible. Since the distribution map for each AR is a cumulative average of an ensemble of myocytes, it was anticipated that the cell-to-cell variation in Z-disc placement would result in a more uniform intensity distribution. Therefore, the observation of distinct striations even upon averaging of α-actinin fluorescence was an unexpected result. On this basis, we posit that the sarcomeres were spatially registered along the myofibril for myocytes of a given length. Therefore, the striations are consistent in the averaged α-actinin distribution despite heterogeneities between myocytes of a given AR. To test whether the periodicity was an artifact of the average distribution map or reflected the underlying sarcomere structure, the spatial frequency was determined from the profiles using the FFT procedure described above. Graphs of intensity profiles chosen close to the myocyte edge and along the myocyte length are shown in FIG. 10B for each AR, each of which exhibits a periodic structure. The dominant frequency for each AR is given in Table 1. These measurements all fall near the reported range for sarcomere length in cultured myocytes (1.94 to 2.1 mm)(H. Mansour et al. (2004) *Circ Res* 94:642-9).

TABLE 1

Figure 10:
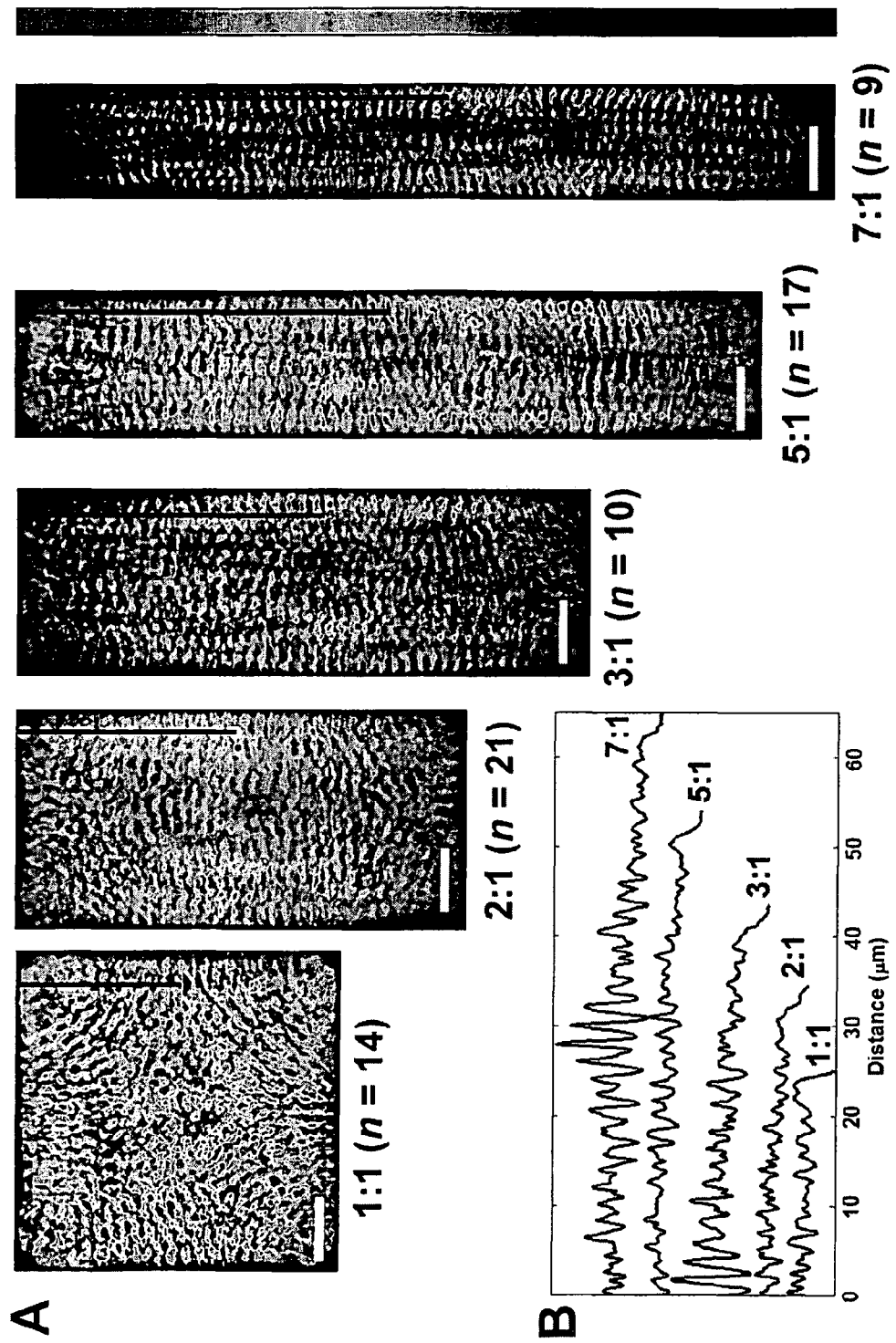
FIG. 10: (A) Average distribution of sarcomeric α-actinin from fixed and stained rectangular myocytes. Each myocyte was registered to a uniform coordinate system, normalized and the pixel intensity was averaged over all myocytes. Scale bar is 10 μm for all panels. (B) Intensity profiles from the averaged images as a function of distance along the black lines illustrated in (A). The lines are offset in the y-axis for clarity.

Sarcomere length estimated from intensity profiles obtained from the averaged sarcomeric α-actinin images shown in FIG. 10, for 1:1 (n = 14), 2:1 (n = 21), 3:1 (n = 10), 5:1 (n = 17), and 7:1 (n = 19). Values calculated by finding the dominant frequency present in the FFT of the intensity profiles. Values are given as mean ± SEM. No statistically significant differences were found for $p < 0.01$.

| | Aspect ratio | | | | |
|---|---|---|---|---|---|
| | 1:1 | 2:1 | 3:1 | 5:1 | 7:1 |
| Sarcomere length (µm) | 2.27 ± 0.08 | 2.25 ± 0.11 | 1.98 ± 0.03 | 2.09 ± 0.05 | 1.95 ± 0.03 |

The influence of physical cues provided by the extracellular matrix (ECM) upon cardiac myocytes has important implications for understanding the transition of myocardium from a normal to a pathological state, as well as the applicability of tissue engineering as a therapeutic response. For example, functional heart grafts require substrates that sufficiently recapitulate the extracellular microenvironment to ensure proper contractility and electrical function (A. Furuta et al. (2006) *Circ Res* 98:705-12). Similarly, the ECM provides structural integrity and support for the heart at the cellular and organ levels, and alterations in fibrillar collagen distribution and geometry (e.g., stiffness induced by fibrosis) have been linked to diastolic dysfunction and heart failure (G. L. Brower et al. (2006) *Eur J Cardiothorac Surg* 30:604-10). In addition, disruption of integrin linkages to the surrounding fibronectin may lead cardiac myocytes to detach from their adhesion sites (anoikis) and has been proposed to contribute to apoptosis (B. Ding et al. (2000) *Circulation* 101:2854-62).

Myocytes cultured on circular islands of ECM protein were spatially confined by a well defined boundary, yet the resultant myofibrillar organization exhibited no consistent pattern. The radii of the ECM islands were sufficiently small to prevent spreading into pleomorphic shapes and allowed formation of focal contacts guided by the ECM boundary (FIG. 7B). The thin, ring-like FAC patterning of the circular myocytes is consistent with those reported for other cell types (C. O. O'Neill et al. (1990) *J Cell Sci* 95:577-86; C. S. Chen et al. (2003) *Biochem Biophys Res Commun* 307:355-61). However, as shown in FIGS. 7C and D, the absence of a repeatable cytoskeletal architecture for the circular myocytes demonstrates that the mere presence of a shape-restricting microenvironment is insufficient to govern sarcomerogenesis into the uniaxial contractile structure seen in vivo. The large variety in cytoskeletal organization observed for these circular myocytes, despite consistent boundary conditions, is similar to prior studies where endothelial cells and fibroblasts cultured on circular ECM substrates produced motility or lamellipodia formation in random directions (K. K. Parker et al., (2002) *Faseb J* 16:1195; X. Jiang et al. (2005) *Proc Natl Acad Sci USA* 102:975-8). Clearly, the specific morphology of the geometric ECM cue presented to the myocyte to stimulate sarcomere assembly for uniaxial contraction is of primary importance, not simply the presence or absence of the cue itself.

The presence of specific geometric cues, such as corners, in myocytes cultured on ECM substrates gave rise to persistent myofibrillar organizational patterns, regardless of whether or not the membrane boundaries were artificially defined by μCP. Large, vinculin-rich focal contacts in the corners radiating towards the myocyte center were a signature of the ECM-myocyte adhesion sites for myocytes with a lower AR (panels ii of FIG. 8A,B). The FAC morphology for 1:1 cardiac myocytes resembled those observed in 1:1 non-muscle cells (K. K. Parker et al., (2002) *Faseb J* 16:1195; C. S. Chen et al. (2003) *Biochem Biophys Res Commun* 307:355-61). Indeed, this same FAC structure was noticeable in pleomorphic myocytes possessing elongated and pointed extensions; the narrow angle formed by the extension led to the formation of larger FACs than in myocytes with curved edges (FIG. 6D). It has been suggested that FAC formation at boundary corners precedes myofibril formation in embryonic cardiac myocytes (K. T. Tokuyasu (1989) *J Cell Biol* 108:43-53). However, since the myocytes prior to substrate adhesion are round in shape (B. M. Rothen-Rutishauser et al. (1998) *J Mol Cell Cardiol* 30:19-31), the subsequent development of corners in the myocyte boundary even in the absence of geometric cues suggests that such features may be an emergent aspect of myofibrillogenesis.

The reconfiguring of focal contacts as the myocyte AR was altered was intimately related to the alignment of the attached myofibrils, as shown by the averaged actin distribution maps. The myofibrillar arrangement of myocytes cultured on μCP circular ECM substrates was also observed with the actin stress fiber network in similarly patterned fibroblasts (C. O. O'Neill et al. (1990) *J Cell Sci* 95:577-86). Likewise, fibroblasts on thin, linear ECM substrates produced tightly parallel bundles of stress fibers (C. O. O'Neill et al. (1990) *J Cell Sci* 95:577-86) in similar fashion to the myofibril orientation in rectangular myocytes with high AR. Hence, it is convenient to consider these two sets of boundary conditions as limiting examples of myofibrillar organization. Between these extremes, the myofibrils underwent a transition in directional anisotropy: from alignment along multiple axes in the 1:1 myocytes (parallel to the four membrane edges and the two diagonals) towards alignment along a single axis in the 7:1 myocytes as the AR of the rectangular myocytes was increased (FIG. 9). Adult cardiac myocytes isolated from normal hearts have an AR of ~7.5, while myocytes from hearts with concentric hypertrophy and eccentric cardiomyopathy decrease and increase their ARs, respectively (S. H. Smith & S. P. Bishop (1985) 17:1005-11; A. M. Gerdes et al. (1992) *Circulation* 86:426-30). Furthermore, the remodeling of myocyte shape likely commences in the early stages of heart failure (T. Onodera et al. (1998) *Hypertension* 32:753-7). Therefore, culturing myocytes into a range of AR using μCP offers an in vitro experimental model of structural pathophysiology to examine and predict alterations in myofibril development concomitantly with cellular shape.

Mechanical stresses are transmitted between the cytoskeleton and the ECM via transmembrane integrin proteins which act to stabilize the FACs (R. M. Ezzell et al. (1997) *Exp Cell Res* 231:14-26). Studies quantifying forces imposed by 1:1 non-muscle cells upon an underlying flexible substratum show that significant tensile forces were exerted at the cell corners, whereas circular non-muscle cells generate weaker forces around the cell periphery (K. K. Parker et al., (2002) *Faseb J* 16:1195; N. Wang et al. (2002) *Cell Motil Cytoskeleton* 52:97). The results show that the FACs in rectangular myocytes promoted directed myofibril assembly and localized preferentially at the corners and ends of the myocyte indicating that the maximal contractile forces for the rectangular cardiac myocytes are confined to regions of high mechanical stress, i.e., the corners of low AR myocytes and the ends of high AR myocytes. Such a result is confirmed by quantification of forces induced by contracting pleomorphic myocytes (N. Q. Balaban et al. (2001) *Nat Cell Biol* 3:466) and results obtained with myocytes patterned onto rectangular μCP ECM islands (see Example 2, below).

Prior to the present invention, the mechanisms regulating the ordered assembly of myofibrils from the constituent sarcomeric protein subunits were unknown. The data described herein elucidate the mechanism and importance of boundary conditions to direct and control alignment of cells and in the development of functional tissues. The arrangement of individual sarcomeres of mature myofibrils indicates a high level of spatial integration; sarcomere bundles are characterized by close apposition and lateral registry, and this arrangement is maintained by intermediate filaments connecting the Z-discs (K. T. Tokuyasu et al. (1985) *Ann NY Acad Sci* 455:200-12). Conversely, deterioration of lateral sarcomeric registry has been shown to be associated with contractile arrest (D. G. Simpson et al. (1996) *Am J Physiol Cell Physiol* 270:C1075-

C1087) and exposure to stretch along the short axis (B. T. Atherton et al. (1986) *J Cell Sci* 86:233-48).

Averaged α-actinin distribution maps were used to examine and quantify the degree of spatial alignment of the individual Z-discs and hence the sarcomeres. As seen in FIG. 10, the distribution maps for a given AR indicate that sarcomere registration occurs not only in parallel but also along the myocyte length as well. This indicates that sarcomerogenesis proceeds based on the extracellular boundary configuration and longitudinal assembly of the developing sarcomere is limited accordingly. The myofibril termini in our patterned myocytes were usually devoid of striations, typical for cardiac myocyte-ECM interfaces (M. H. Lu et al. (1992) *J Cell Biol* 117:1007-22). However, this is not the case for myocyte-myocyte connections at the intercalated discs, where Z-discs are associated with the adherens junction (M. H. Lu et al. (1992) *J Cell Biol* 117:1007-22). Therefore, sarcomere alignment by length-sensitive regulation of myofibrillogenesis may not be restricted to the single myocyte level but may also promote tissue-wide registration of the contractile machinery via the interconnectivity of the cardiac syncytium. A microstructure of cardiac tissue constructs has been described (P. Camelliti et al. (2005) *Microsc Microanal* 11:249-59).

The reorganization of the cardiac myocyte myofibrillar structure in response to geometric stimuli created by micro-patterned ECM islands leads to repeatable and distinctive cytoskeletal architectures. These ECM cues serve to both create spatial anisotropy during myofibrillogenesis and contribute to sarcomere registration within the myocyte and possibly at the tissue level. Therefore, modification of cardiac myocyte morphogenesis to recapitulate in vivo myocyte shape provides an effective means to direct and control sarcomerogenesis under normal and pathological conditions.

Example 2

Ordered Processes in the Self-Organization of a Muscle Cell

Cellular form and function are the result of self-assembly and -organization of its molecular constituents into coupled networks. A specific example of this phenomenon is myofibrillogenesis, the formation and organization of myofibrils in striated muscle. Although several hypotheses have been proposed to describe maturation of myofibrils, the physical principles governing their development into a mature, functional structure were not well understood prior to the present invention Described herein is a mechanism of cytoskeletal and myofibril organization of cardiac myocytes. Computer simulations and in vitro assays to control myocyte shape demonstrated that distinct cytoskeletal architectures arise from two temporally-ordered, organizational processes: the interaction between stress fibers, premyofibrils and focal adhesions, as well as cooperative alignment and parallel bundling of myofibrils. The results identify a hierarchy of mechanisms that regulate the self-organization of the contractile cytoskeleton.

The topology of gene regulatory networks is not sufficient to explain how form and function emerge during development. Morphogenesis is generally believed to require a robustly organized synchrony between transcriptional and posttranscriptional processes, but how much of development is attributable to post-translational self-assembly and self-organization has heretofore been unclear. One example is myofibrillogenesis in striated muscle, where expression of sarcomeric proteins is necessary, but not sufficient to explain the structure-function relationships of the myocyte. The data described herein indicate that boundary conditions play a pivotal role in myofibrillogenesis and the development of functional muscle tissue.

Myofibrillogenesis is the serial alignment and parallel bundling of sarcomeres, the contractile motors of a muscle cell, and is required for spatially ordered contraction (E. Ehler et al. (1999) *J Cell Sci* 112 (Pt 10):1529). Stress-fiber like structures containing sarcomeric proteins assemble marking the transition of the stress fiber to the intermediate premyofibril, a more contractile stage, and subsequently mature to the myofibril as the final protein ensemble (G. A. Dabiri et al. (1997) *Proc Natl Acad Sci USA* 94:9493; D. Rhee et al. (1994) *Cell Motil Cytoskeleton* 28:1). Precursors of the Z-band, known as Z-bodies, bind periodically along nascent myofibrils, facilitating parallel alignment (G. A. Dabiri et al. (1997) *Proc Natl Acad Sci USA* 94:9493; D. Rhee et al. (1994) *Cell Motil Cytoskeleton* 28:1; J. M. Sanger et al. (1986) *J Cell Biol* 102:2053). In a mature myocyte, the myofibrils are arranged into tightly organized bundles spanning the length, rather than the width, of the cell (G. A. Dabiri et al. (1997) *Proc Natl Acad Sci USA* 94:9493). Whereas sarcomere assembly has been well studied (G. A. Dabiri et al. (1997) *Proc Natl Acad Sci USA* 94:9493; D. Rhee et al. (1994) *Cell Motil Cytoskeleton* 28:1; J. M. Sanger et al. (1986) *J Cell Biol* 102:2053; A. A. Dlugosz et al. (1984) *J Cell Biol* 99:2268; A. Du et al. (2003) *Dev Biol* 257:382; H. Holtzer et al. (1997) *Cell Struct Funct* 22:83), the mechanisms of myofibrillar patterning and its functional consequences have not.

Experiments were carried to evaluate whether 2 temporally ordered processes regulate the spatial arrangement of stress fibers and myofibrils. The first mechanism, referred to as the extrinsic process, governs stress fiber assembly and formation of their anchoring focal adhesion complexes (FACs) and occurs on the scale of seconds to minutes (N. Q. Balaban et al. (2001) *Nat Cell Biol* 3:466; Y. L. Wang (1984) *J Cell Biol* 99:1478). Recent work suggests that FAC assembly and the lengthening/bundling of its attached stress fibers are coupled by a positive feedback loop (N. Q. Balaban et al. (2001) *Nat Cell Biol* 3:466; A. D. Bershadsky et al. (2003) *Annu Rev Cell Dev Biol* 19:677; M. Chrzanowska-Wodnicka & K. Burridge (1996) *J Cell Biol* 133:1403; C. G. Galbraith et al. (2002) *J Cell Biol* 159:695; I. L. Novak et al. (2004) *Phys Rev Lett* 93, 268109) that results in continued lengthening of stress fibers relative to cellular boundary conditions (N. Q. Balaban et al. (2001) *Nat Cell Biol* 3:466; K. K. Parker et al., (2002) *Faseb J* 16:1195; M. Thery et al. (2006) *Cell Motil Cytoskeleton* 63:341). The cellular boundary conditions are thus often referred to as extrinsic cues (S. E. Siegrist & C. Q. Doe (2006) *Development* 133:529), with their role in mitotic spindle orientation having been investigated by experimental and theoretical approach recently (M. Thery et al. (2007) *Nature* 447: 493). The second mechanism is a slower intrinsic process, where adjacent premyofibrils preferentially align in parallel over a time scale of hours (G. A. Dabiri et al. (1997) *Proc Natl Acad Sci USA* 94:9493; N. M. McKenna et al. (1986) *J Cell Biol* 103:2163). The temporal differences between the extrinsic and intrinsic mechanisms were found to establish a hierarchy amongst these processes that govern the organization of the contractile cytoskeleton for cells to respond to different environments.

Computational Model of Sarcomere Assembly

Figure 11:
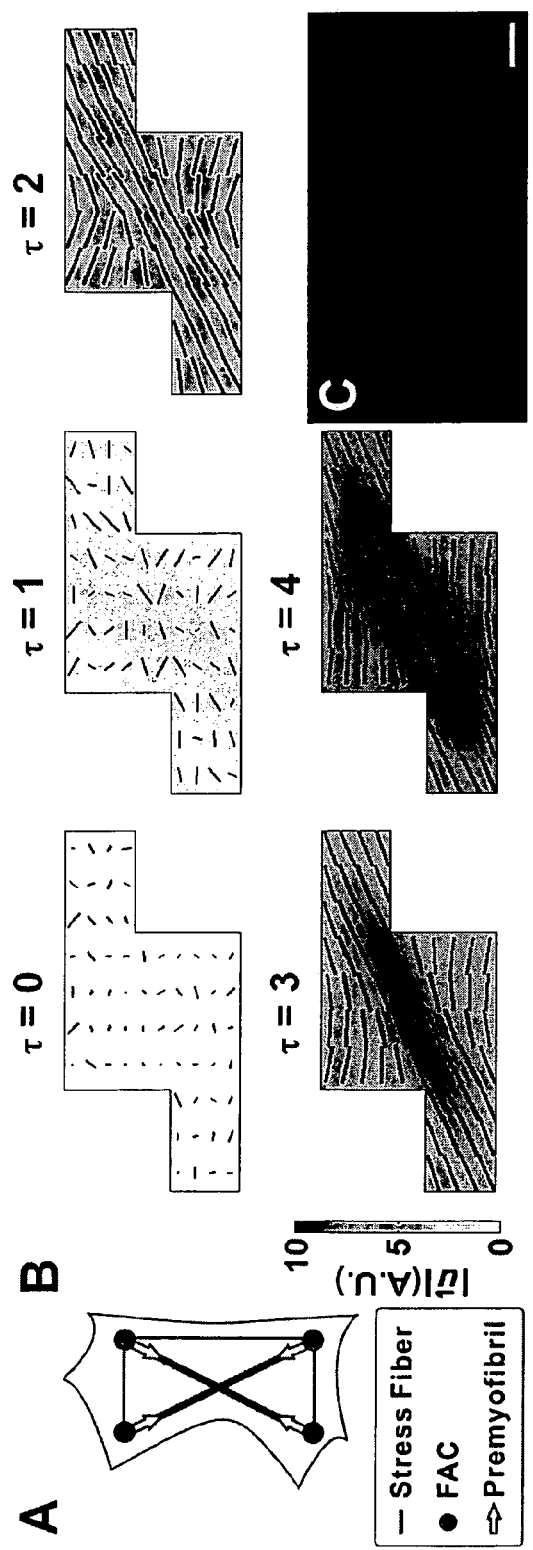
FIG. 11 is a schematic representation and simulated dynamics of premyofibril organization model. (A) Top view of a 2D myocyte with pleomorphic geometry. FACs (focal adhesion complexes) are distributed according to the tension field generated by stress fibers. The architecture of the stress fiber network serves as a structural template for assembly of premyofibrils. The local orientation of premyofibrils is governed by the orientations of local stress fibers and neighboring premyofibrils. (B) Simulated results for the dynamic profile of premyofibril organization in a stair-step-shaped myocyte. The grayscale and lines represent the premyofibril bundling, $|\vec{u}|$, and the orientation of $\vec{u}$, respectively; grey color values are in arbitrary units. Premyofibril bundling and orientation were initially random ($\tau=0$). As time elapsed, they reorganized and oriented themselves along the longest cellular diagonal. (C) Immunostaining of the actin network from a myocyte with similar shape agrees with the numerical prediction; scale bar: 10 μm.
Figure 14:
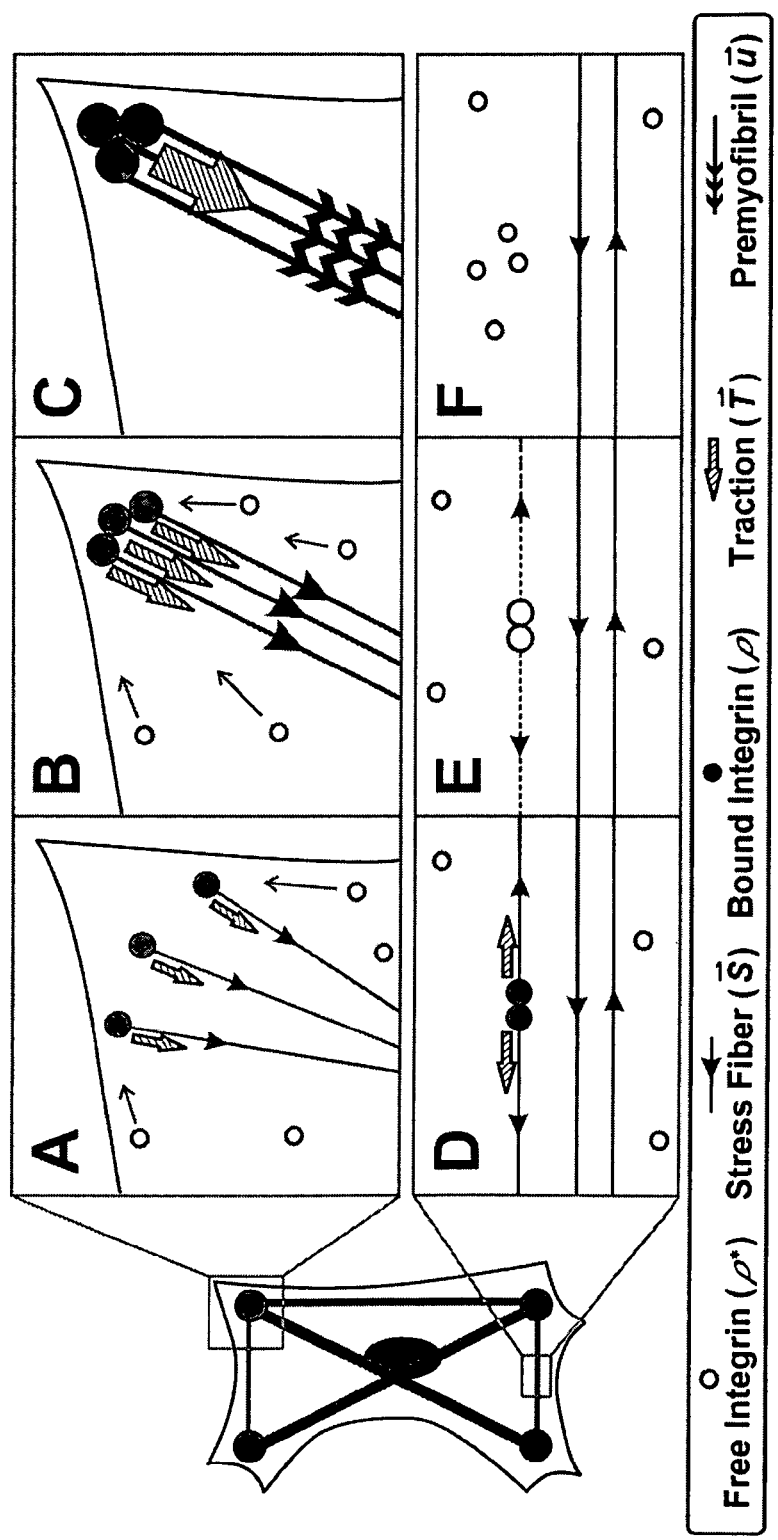
FIG. 14 shows a schematic representation of myofibril reorganization in a 2D myocyte (left; lines: actin; oval: nucleus; circles: FACs). (A) Traction ($\vec{T}$) exerted on bound integrins, as determined by the sum of all anchoring stress fiber vectors ($\vec{S}$) recruits free integrins and promotes growth of FACs. (B) Continued recruitment of free integrins to the growing FAC at the cellular corners promotes bundling of the stress fibers and subsequently increases traction. (C) Using the bundled stress fibers as a structural template, premyofibrils $\vec{u}$ align in parallel and develop into a fully organized bundle, further amplifying local traction to result in FAC maturation. (D) Bound integrins with zero net traction cannot recruit free integrin and is dissociated from the membrane, leading to disassembly of its associated stress fiber (E). Consequently, stress fibers on shorter axes (F) are less bundled than that following the longest diagonal of the cell.

A computational model was developed that supplements the efforts of Sanger and colleagues (D. Rhee et al. (1994) *Cell Motil Cytoskeleton* 28:1; A. Du et al. (2003) *Dev Biol* 257:382) by broadening the spatial scale to the whole cell and temporally focusing on the steps preceding Sanger's model of sarcomere assembly. The model is schematically illustrated in FIG. 14. The model recapitulates FAC assembly and the cytoplasmic arrangement and bundling of premyofibrils in 2D myocytes (FIG. 11A). Five field variables are defined at every position $\vec{r}$, in a defined geometry $\Omega$ at time t: (1 and 2) $\rho$ and $\rho^*$, the density of bound and unbound integrin, respectively; (3) $\vec{T}$, the local traction exerted on FACs; (4) $\vec{S}$, the density and dominant orientation of stress fibers resulting from the extrinsic process; and (5) a, in which the direction specifies the local orientation, and the magnitude $|\vec{u}|$ represents parallel bundling, of premyofibrils. The following assumptions were made: 1) bundling of stress fibers is proportional to the density of the anchoring FAC (M. Thery et al. (2006) *Cell Motil Cytoskeleton* 63:341); 2) each contractile cytoskeleton connecting two FACs is approximated as a force vector with strength determined by two temporally ordered components, a fast component constituted by stress fibers and a slow component modulated by premyofibrils; 3) stress fibers serve as structural templates for premyofibril assembly (A. A. Dlugosz et al. (1984) *J Cell Biol* 99:2268); 4) the local orientation of the premyofibril is regulated by the orientation of local stress fiber and neighboring premyofibrils (G. A. Dabiri et al. (1997) *Proc Natl Acad Sci USA* 94:9493; D. Rhee et al. (1994) *Cell Motil Cytoskeleton* 28:1; A. A. Dlugosz et al. (1984) *J Cell Biol* 99:2268; N. M. McKenna et al. (1986) *J Cell Biol* 103:2163); and 5) the strength of $\vec{T}$ regulates the redistribution of $\rho$(N. Q. Balaban et al. (2001) *Nat Cell Biol* 3:466; C. G. Galbraith et al. (2002) *J Cell Biol* 159:695; L. B. Smilenov et al. (1999) *Science* 286:1172; E. Zamir et al. (2000) *Nat Cell Biol* 2:191).

Time-scales are normalized with respect to that of premyofibril bundling ($\tau$~10-20 hours)(G. A. Dabiri et al. (1997) *Proc Natl Acad Sci USA* 94:9493; N. M. McKenna et al. (1986) *J Cell Biol* 103:2163) with the assembly and disassembly of stress fibers assumed to take place instantaneously (Y. L. Wang (1984) *J Cell Biol* 99:1478; I. L. Novak et al. (2004) *Phys Rev Lett* 93, 268109). The temporal change of traction, $\vec{T}$, at $\vec{r}$, was determined by integrating the tension contributed from all connected contractile cytoskeletons:

$$\frac{\partial \vec{T}}{\partial \tau} = \alpha_1 \left\{ T_0 H(\vec{r}) G(\vec{r}) \int_\Omega H(\vec{r}') G(\vec{r}') [\vec{r}' - \vec{r}] d^2 r' - \vec{T} \right\}. \quad (1)$$

Here, $\alpha_1$ is a time scale normalizing factor; $T_0$ is a scaling factor; the strength of the stress fibers spanning from $\vec{r}$ to $\vec{r}'$, $G(\vec{r})G(\vec{r}')[\vec{r}'\sim\vec{r}]$, is assumed to be proportional to both fiber length $[\vec{r}'\sim\vec{r}]$, and local FAC density specified by the function $G(\vec{r})$ (N. Q. Balaban et al. (2001) *Nat Cell Biol* 3:466; M. Thery et al. (2006) *Cell Motil Cytoskeleton* 63:341); and the modulation of contractile strength by premyofibrils is represented by $H(\vec{r})$. The temporal change of FAC density is computed as the difference between the generation and decay of bound integrin:

$$\frac{\partial \rho}{\partial \tau} = \alpha_2 \{\rho^* [\alpha_0 + Q(|\vec{T}|)] - \beta \rho\}, \quad (2)$$

Here, $\alpha_2$ is another time scale normalizing factor; $\alpha_0$ and $\beta$ are the spontaneous rate of FAC assembly and disassembly, respectively; and function $Q(|\vec{T}|)$ represents the positive feedback between FAC formation and stress fiber assembly. The network of stress fibers, designated as $\vec{S}$, was then updated according to $\rho$. To determine the density and local orientation of the network, all stress fibers traversing a given position $\vec{r}$ were grouped with respect to their orientation. The orientation of $\vec{S}$ at $\vec{r}$ is thus designated by the group possessing the greatest quantities of stress fibers and the density is determined by the total quantity of all fibers intersecting $\vec{r}$, $$|\vec{S}| = \int_\Omega d^2 r' \left( \int_\Omega d^2 r'' G(\vec{r}') G(\vec{r}'') \{ dr^2 \cdot \delta[(\vec{r}' - \vec{r})|\vec{r}'' - \vec{r}| + (\vec{r}'' - \vec{r})|\vec{r}' - \vec{r}|] \} \right). \quad (3)$$

The premyofibrils were also assumed to impose torques upon neighboring premyofibrils and influence their orientations. This was implemented by minimizing the intersection angle between pairwise adjacent $\vec{u}$, assuming that the strength of the torque is a function of $|\vec{u}|$. Together, we have $$\frac{\partial |\vec{u}|}{\partial \tau} = S_0 |\vec{S}| - |\vec{u}|, \quad (4)$$

and $$\frac{\partial \hat{u}}{\partial \tau} = u_0 \int_{\Omega'} \{|u'|(\hat{u}' \cdot \hat{u})[\hat{u}' - (\hat{u}' \cdot \hat{u})\hat{u}]\} d^2 r' + \hat{S} - \hat{u}. \quad (5)$$

Here, $S_0$ and $u_0$ are scaling factors; $\hat{S}$ and $\hat{u}$ are the unit vectors of $\vec{S}$ and $\vec{u}$, respectively; and $\Omega$ stands for the near neighboring of a given position. In the simulations, the same parameter values were applied across the different shapes to ensure that the observed values resulted from geometric considerations alone. The model differs from previous reports that do not consider focal adhesion kinetics, mutual alignment of neighboring fibers (V. S. Deshpande et al. (2006) *Proc Natl Acad Sci USA* 103:14015), or that the tension of a fiber is not proportional to the length between its anchoring FACs (I. L. Novak et al. (2004) *Phys Rev Lett* 93, 268109).

To verify our computational results, culture substrates containing micrometer-sized extracellular matrix (ECM) islands fabricated by microcontact printing to analyze the effects of ECM-dependent changes in cell shape on myofibrillar patterning were used. When freshly harvested neonatal rat ventricular myocytes are cultured on individual islands surrounded by nonadhesive regions, the myocytes remodel to take on the shape of the islands. An example of the simulated dynamics visualized for premyofibril bundling and realignment is illustrated in FIG. 11B for a stair-step shaped cell. The simulation data show that alignment of premyofibrils first occurred in the earliest time point in the center of the cell, followed the longest diagonal, and recruited additional adjacent fibers to form a bundled, parallel arrangement. Immunofluorescent microscopy of myocytes cultured on similarly shaped islands and stained against actin reveals similar cytoskeletal architecture after three days in culture (FIG. 11C). These data indicate that the model accurately predicts the pattern of myofibrils with respect to complex cues in the ECM.

To further test the hypothesis, myocyte sensitivity to various cellular boundary conditions was examined. Studies were carried out to determine whether myocytes patterned on islands of heterogeneous curvature have both extrinsic and intrinsic processes that potentiate the organization of the cytoskeletal network, but when cultured on islands of homogeneous curvature have no external cues to break the symmetry of the isotropic cytoskeleton and are thus dependant on slower, intrinsic events to polarize the myofibrillar array. Some publications suggested that myofibrillogenesis begins in the perinuclear region in myocytes (D. Rhee et al. (1994) *Cell Motil Cytoskeleton* 28:1) and that myofibrils are most often observed to align with the longitudinal axis of the cell (G. A. Dabiri et al. (1997) *Proc Natl Acad Sci USA* 94:9493). Generally, the cell nucleus localizes to the centroid of the cell. Two cases of the cell were examined with heterogeneous curvature at the periphery: the square, where the nucleus is generally positioned on the diagonal and the equilateral triangle, where the long axes are along the cell periphery.

Figure 12:
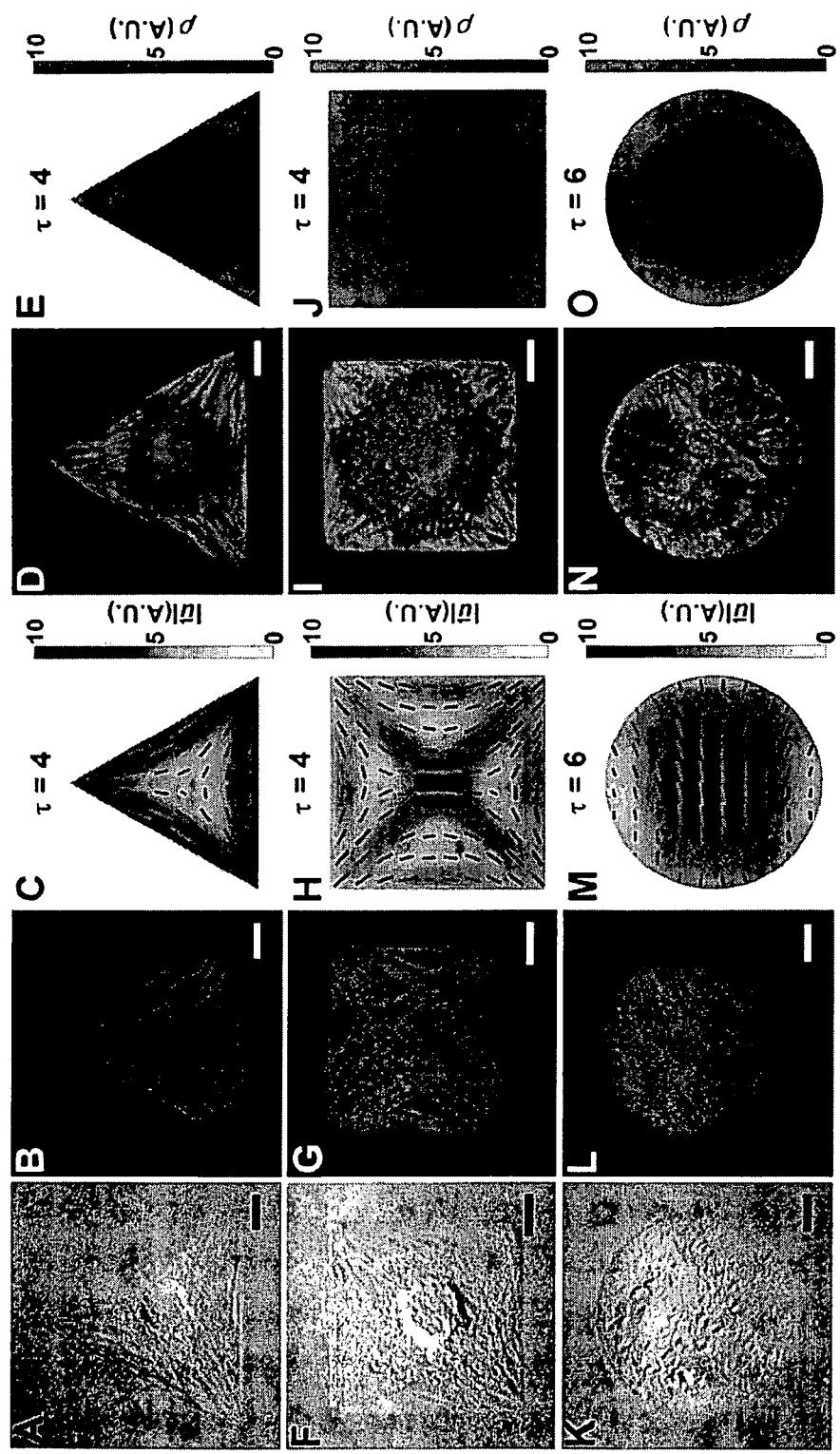
FIG. 12 shows experimental images and model depictions of organization of actin and FACs. First column: DIC images of micropatterned triangular (A), square (F), and circular (K) myocytes. Second column: Immunostained actin in triangular (B) and square (G) myocytes followed the longest cellular dimension, while actin fibers in the circular myocyte (L) primarily oriented on the 2 to 8 o'clock axis. Third column: Predicted premyofibrillar pattern (u) of triangular (C), square (H), and circular (M) myocytes agrees with experimental results. The steady state of the circular cell occurred slower ($\tau=6$) than that of the triangular and square cells ($\tau=4$). The grayscale and lines represent premyofibril bundling and local orientation, respectively. Fourth column: Immunostained vinculin of triangular (D) and square (I) myocytes was concentrated at cellular corners, while two opposing plaques of vinculin localized on the 2 to 8 o'clock axis in the circular (N) myocyte. Fifth column: Simulated FAC density (ρ) at steady state in triangular (E), square (J), and circular (O) cells was consistent with experimental results. The FAC distribution in a circular myocyte (O) was expected to break the symmetry. Grey color values in simulations are in arbitrary units; scale bars: 10 μm.

Fluorescent staining of actin in myocytes cultured on square and triangular ECM islands revealed that polymerized actin fibers were densely arranged along the longest axes (FIG. 12). The fibers are regularly punctuated along their length, highlighting sarcomere presence (FIG. 12B, G). The cells differed in that the myofibrillar array exists under the nucleus in the square myocyte and often around the nucleus in the triangular myocyte. At steady state, modeled triangular and square cells displayed the same cytoskeletal arrangement as the in vitro results, with enhanced parallel bundling occurring along the longest axis of these cells (FIG. 12C, H). Immunostaining of vinculin in the same myocytes revealed elongated FACs in the corners of the square and triangular cells that were oriented with their attached myofibrils (FIG. 12D, I). The positive feedback loop in the computational model predicted the same accumulation of FACs, as indicated by the bound integrin density located in the corners (FIG. 12E, J). As indicated in the figure and observed in the simulation shown in FIG. 11B, these architectures appeared after four epochs of the simulation, with the predominant orientation of the premyofibrils occurring quickly and parallel bundling increasing with time to further stabilize the myofibrillar architecture with respect to the geometric cues in the ECM. This indicates that FACs localize and mature at the corners because stress fibers and premyofibrils that align along the longest axes of the cell are strongest by virtue of their greater propensity for parallel bundling and binding myosin motors.

In contrast, myocytes cultured on circular ECM islands for the same period of time as the square and triangular myocytes (FIG. 12K) and stained for actin have no distinctive cytoskeletal polarity (FIG. 12L). Without an external cue to establish the hierarchy of organizational processes, computer simulations indicated that myofibrillar polarity emerge after six epochs. Transient multi-pole patterns develop prior to equilibrium where the cytoskeleton is anisotropic, with parallel bundles of polymerized actin extending across the cell diameter (FIG. 12M). In vitro, vinculin stains irregularly around the myocyte perimeter (FIG. 12N). In silico, after a similarly prolonged simulation, FACs appear as opposing bands along the cell periphery (FIG. 12O). This patterning is due to a random, intercellular, symmetry-breaking event and while the model will always converge on a polarized cell with an anisotropic cytoskeletal architecture, circular cells in vitro often display irrepeateable cytoskeletal structures after 2-3 days in culture. Together, the simulation and experimental results shown in FIG. 12 suggest that the faster extrinsic process of stress fiber alignment is regulated by extracellular cues that promote stabilization of stress fibers and FACs long enough for parallel bundling of premyofibrils and myofibrillogenesis.

Figure 13:
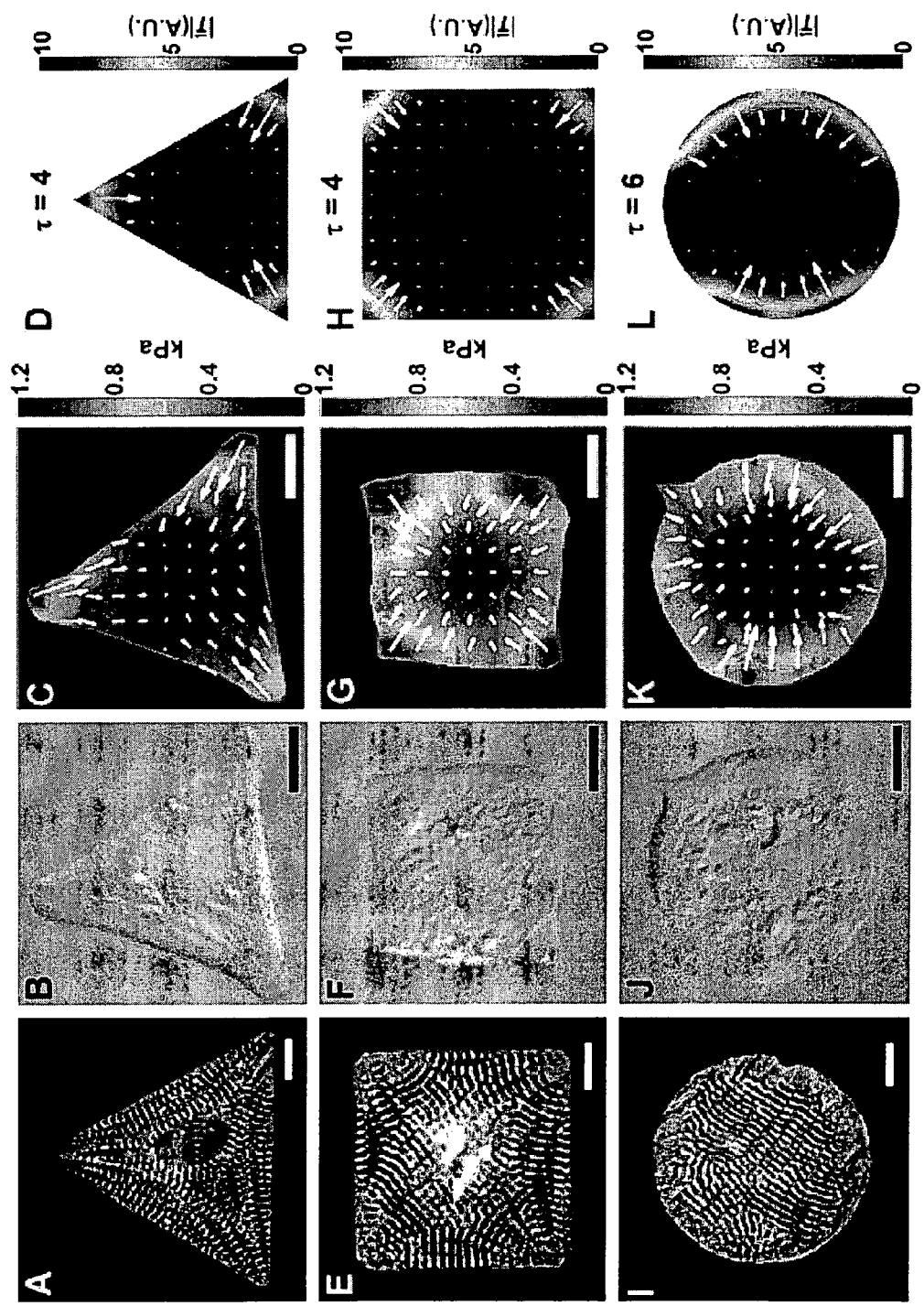
FIG. 13 shows sarcomeric structure, traction force at peak systole, and model predictions. First column: Sarcomeric α-actinin immunofluorescence delineates the Z-lines in triangular (A), square (E) and circular (I) myocytes. Z-line orientation indicated that the axis of contraction was parallel to the longest axis of the cell. In the circular myocyte, most of the Z-lines aligned on the 1 to 7 o'clock axis with the dominant axis of contraction expected to follow the 4 to 10 o'clock direction. Second column: DIC images of micropatterned triangular (B), square (F), and circular (J) myocytes. Third column: The contractile traction maps of the triangular (C) and square (G) myocytes displayed high tractions at the cellular corners. The contraction map of the circular myocyte (K) indicated that the cell broke radial symmetry, with the principal axis of contraction along the 3 to 9 o'clock axis. Fourth column: Numerical results of predicted traction map ($\vec{T}$) of triangular (D), square (H), and circular (L) myocytes replicated experimental results. In the third and fourth columns, the grayscale and arrows represent the magnitude and direction of traction, respectively. Grey color values in simulations are in arbitrary units; scale bars: 10 µm.

Proper myocyte functioning requires correct myofibrillar patterning for coordinated contraction (B. Russell et al. (2000) *J Appl Physiol* 88, 1127). Fluorescent micrographs of myocytes immunostained against sarcomeric α-actinin revealed distinct myofibrillar patterning on ECM islands of heterogeneous curvature (FIG. 13A, E). The sarcomeric Z-lines register in the internal angles of the corners of both the square and triangle and are perpendicular to the orientation of the actin fibers. To test the functional implications of myofibrillar patterning, a new technique was developed for micropatterning adhesive islands on flexible substrates for traction force microscopy (TFM). Spatiotemporal maps of the tractional forces exerted on the substrate during contraction were measured by detecting the displacement of fluorescent beads embedded in the flexible substrate from frame to frame using high speed fluorescent video microscopy and calculating the stresses from the known mechanical properties of the substrate. When freshly harvested myocytes were cultured on ECM islands patterned on flexible substrates, they remodel to assume the shape of the island in the same manner as they do on rigid substrates (FIG. 13B, F). Unlike myocytes cultured on rigid substrates, myocytes on flexible substrates do not contract isometrically and were observed to shorten as in traditional assays of single myocyte contractility. During systole, the fluorescent beads in the flexible substrate were being pulled towards the center of the cell by the shortening FAC-anchored myofibrils, and during diastole they reversed direction, as the elastic recoil of the myocyte pushes them back to the rest position. During systole, myocytes generated a unique contractile footprint that mimics the position of the FACs depicted in FIG. 12, with the highest stresses exerted on the substrate at the myocyte corners at peak systole (FIG. 13C, G). This pattern matches computational results of the model (FIG. 13D, H). These data show that at the architectural steady state, the peak systolic tractions appear at the high-curvature boundaries of triangular and square myocytes, consistent with the spatial distribution of FACs shown in FIG. 12.

In myocytes of homogeneous curvature, sarcomere patterns are not reproducible (FIG. 13I). Myocytes cultured on circular ECM islands remodel to a rounded shape and appear to reduce their diameter uniformly during systole (FIG. 13J). At peak systole, a polarization is apparent but not as distinctive as those of the square and triangular cells (FIG. 13K), consistent with findings with nonmuscle cells (N. Wang et al. (2002) *Cell Motil Cytoskeleton* 52:97). The model predicts a similar contractile signature, with the peak stresses coincident with the location of the widest FAC bands observed in FIG. 12O. These data demonstrate that the largest contractile forces are exerted on the substrate by the strongest myofibrils that anchor to the largest focal adhesions.

Thus, for a cardiac muscle cell to properly align its sarcomeres most efficiently, a local symmetry break is required to potentiate the assembly and organization of the actin network to serve as a template for myofibrillogenesis. The break can be due to a static, external cue, such as a geometric feature in the boundary conditions imposed on the cell, or it can be a dynamic internal cue. The sequential order of these temporally-variable events suggests a hierarchy of post-translational, self-assembly and organizational processes that are required for coupling cellular form and function.

GLOSSARY OF PARAMETERS AND FUNCTIONS

A Total area of a defined geometry
$D_\rho$ Membrane diffusion coefficient of unbound integrin d Decay constant for the amplification of traction by premyofibrils
$d_0$ Scaling constant for amplification of traction by premyofibrils
G Function describes relationship of stress fiber bundling to FAC density
H Function specifies modulation of contractile strength by premyofibrils
$H_0$ Maximum amplification of traction by premyofibrils
Ω Function specifies dependence of FAC assembly on local traction
$\vec{r}$ Position vector
$\vec{S}$ Local density and orientation of stress fibers network
$S_0$ Scaling constant of premyofibril bundling
$\vec{T}$ Traction exerted on the bound integrin
$T_0$ Scaling factor of the pulling force generated by stress fibers on a FAC
$\vec{u}$ Local orientation and parallel bundling of premyofibrils
$u_0$ Scaling constant for reorientation of premyofibrils by neighboring premyofibrils
W Function determines whether two connected stress fibers align in parallel
Ω Geometry of the cell
$\alpha_0$ Spontaneous assembly rate of FAC
$\alpha_1$ Time-scale normalizing constant for stress fiber assembly
$\alpha_2$ Time-scale normalizing constant for FAC assembly
β Disassembly rate of FAC
θ Intersection angle between two adjacent premyofibrils
ρ Density of bound integrin, i.e., FAC density
$\rho_{sat}$ Saturation FAC density for stress fiber bundling
ρ* Density of unbound integrin
τ Time scale of premyofibril bundling
δ Kronecker delta function
π Ratio of a diameter of a circle to the circumference; ~3.14159 . . . .

Example 3

Modeling Dynamic Alignment of Premyofibrils

A 2D myocyte that fully spreads to a defined geometry Ω was evaluated by focusing on variables measured experimentally. A full description of the time-dependent organization of premyofibrils requires at least five field variables defined as a function of position $\vec{r}$ and time t: (1, 2) the density of bound and unbound integrin, ρ and ρ*, respectively; (3) the local traction exerted on the bound integrin, $\vec{T}$; (4) the local density and orientation of the stress fiber network, $\vec{S}$'; and (5) the premyofibril, $\vec{u}$, in which the directional component of $\vec{u}$ denotes the dominant orientation of premyofibrils, and the magnitude of $\vec{u}$ represents the co-localization of premyofibrils into a bundle. Prior studies suggest that FAC formation takes place on a fast time scale (on the order of seconds), followed by the assembly/disassembly rate of the stress fiber (minutes) and bundling of the premyofibril (~10-20 hours). Thus, all time-scales t are normalized with respect to that of the premyofibril bundling τ, with all other variables in non-dimensional units. The following assumptions were made.
1. The bundling of stress fibers between two FACs increases in proportion to the density of FACs, which is saturated at a predefined density.
2. Contractile cytoskeletons between two FACs are approximated as a bidirectional force vector with strength determined by two temporally ordered components, a fast component constituted by stress fibers and a slow component modulated by premyofibrils.
3. The strength of stress fibers is proportional to both fiber length and bundling.
4. The modulation of contractile strength by local premyofibrils is proportional to the alignment between the premyofibrils and local traction vector.
5. The density of a FAC is dependent on the local traction and hence is redistributed according to the traction field.
6. The architecture of the stress fiber network serves as a structural template for assembly of premyofibrils.
7. The local orientation of premyofibrils is governed by that of the stress fiber at the same position and neighboring premyofibrils.

Thus as illustrated in FIG. 14, FACs and stress fibers in our model have two fates. When the net traction exerted on a FAC is zero, the bound integrins are dissociated from the membrane, with disassembly of anchoring stress fibers. When net traction is not zero, both FACs and their associated stress fibers are structurally reinforced due to the positive feedback loop as discussed above.

The model begins with the equation that governs the temporal change of local traction. The FAC field and associated stress fiber network can be considered to be quasi-static with respect to the time scale of premyofibril bundling. Thus temporal development of $\vec{T}(\vec{r},\tau)$ is determined by the sum of the contractile forces generated by all contractile cytoskeletons originating from $\vec{r}$, minus the force lost by the disassembly of these fibers. This yields Eq. 1 of Example 2 and is repeated here for clarity:

$$\frac{\partial \vec{T}}{\partial \tau} = \alpha_1 \left\{ T_0 H(\vec{r}) G(\vec{r}) \int_\Omega H(\vec{r}') G(\vec{r}') [\vec{r}' - \vec{r}] d^2 r' - \vec{T} \right\}. \quad (S1)$$

Here, $\alpha_1$ is a time-scale normalizing factor for stress fiber assembly/disassembly and is on the order of ~10-10³ and $T_0$ is a scaling factor. The function $G(\vec{r})$ specifies the relationship of stress fiber bundling to FAC density, limited by the saturation value $\rho_{sat}$, while $G(\vec{r})G(\vec{r}')(\vec{r}'-\vec{r})$ represents the force vector generated by stress fibers spanning from $\vec{r}$ to $\vec{r}'$, and $H(\vec{r})$ is a function of the inner product of $\vec{T}$ and $\vec{u}$ and denotes the modulation of contractile strength by local premyofibril orientation. The functions $G(\vec{r})$ and $H(\vec{r})$ are formulated as follows:

$$G(\vec{r}) = \frac{\rho}{\rho_{sat} + \rho} \quad (S2)$$

$$H(\vec{r}) = \frac{H_0 e^{d_0 |\vec{u}| |\hat{T} \cdot \hat{u}|^d}}{H_0 - 1 + e^{d_0 |\vec{u}| |\hat{T} \cdot \hat{u}|^d}},$$

where $H_0$ is the maximum amplification contributed by the alignment between the premyofibril $\vec{u}$ and traction $\vec{T}$ at $\vec{r}$; $\hat{T}$ and $\hat{u}$ are the unit vectors of $\vec{T}$ and $\vec{u}$, respectively, with $|\hat{T} \cdot \hat{u}|$ denoting the angular effect of alignment; and $d_0$ is a scaling factor and d specifies how fast the amplification decays if $\vec{T}$ is not aligned with $\vec{u}$. Because the tension of a premyofibril is bidirectional, we ignore the sign of the inner product between vectors $\vec{T}$ and $\vec{u}$. In addition, since each stress fiber is approximated as a bidirectional vector with equal and opposite forces, the sum of all tractional forces exerted by the cell on the substrate must be zero, as required by modeling a stationary cell.

The temporal change of FAC density is computed as the difference between the generation and decay of bound integrin:

$$\frac{\partial \rho}{\partial \tau} = \alpha_2 \{\rho^*[\alpha_0 + Q(|\vec{T}|)] - \beta\rho\}. \tag{S3}$$

Note that Eq. S3 matches Eq. 2 of Example 2, where $\alpha_2$ is a time-scale normalizing factor and is on the order of $\sim 10^2$-$10^5$; $\alpha_0$ and $\beta$ are the spontaneous rate of FAC assembly and disassembly, respectively; and $Q(|\vec{T}|)$ specifies the dependence of FAC assembly on local traction, and is assumed to be $|\vec{T}|$ based on previous work. The functions $Q(|\vec{T}|)$ and $G(\vec{r})$ represent the positive feedback between FAC formation and stress fiber assembly.

The temporal evolution of unbound integrin $\rho^*$ can be expressed in the form of a reaction-diffusion equation:

$$\frac{\partial \rho^*}{\partial \tau} = \alpha_2\{-[\alpha_0 + Q(|\vec{T}|)]\rho^* + \beta\rho\} + D_\rho \nabla^2 \rho^*. \tag{S4}$$

Here $D_\rho$ is the membrane diffusion coefficient of unbound integrin. We normalize $\rho$ and $\rho^*$ such that $\rho + \rho^* = 1$ to produce the following mass conservation relationship:

$$\int_\Omega (\rho + \rho^*) d^2 r = \int_\Omega d^2 r = A. \tag{S5}$$

To represent the stress fiber network, $\vec{S}$, we group all stress fibers traversing a given position $\vec{r}$ with respect to their direction. The orientation of $\vec{S}$ is determined by the group possessing the greatest quantity of stress fibers. The orientation is found by identifying the angle of intersection between the vectors $\vec{r}' - \vec{r}$ and $\vec{r}'' - \vec{r}$, where $\vec{r}'$ and $\vec{r}''$ are arbitrary locations; a stress fiber traversing $\vec{r}$ will connect $\vec{r}'$ and $\vec{r}''$ if the angle between them is $\pi$. The density of $\vec{S}$ is thus defined as the total quantity of stress fibers intersecting $\vec{r}$ and is expressed as:

$$|\vec{S}| = \int_\Omega d^2 r' \int_\Omega G(\vec{r}') G(\vec{r}'') W(\vec{r}, \vec{r}', \vec{r}'') d^2 r'' \tag{S6}$$

$$\text{where } W(\vec{r}, \vec{r}', \vec{r}'') = \begin{cases} 1, & \text{if } \frac{(\vec{r}' - \vec{r}) \cdot (\vec{r}'' - \vec{r})}{|\vec{r}' - \vec{r}||\vec{r}'' - \vec{r}|} = -1 \\ 0, & \text{otherwise.} \end{cases}$$

Here, $W(\vec{r}, \vec{r}', \vec{r}'')$ stands for the function that determines whether two connected stress fibers align in parallel. Without loss of generality, $W(\vec{r}, \vec{r}', \vec{r}'')$ can be re-written as $$W(\vec{r}, \vec{r}', \vec{r}'') = dA \cdot \delta[(\vec{r}' - \vec{r})|\vec{r}'' - \vec{r}| + (\vec{r}'' - \vec{r})|\vec{r}' - \vec{r}|], \tag{S7}$$

where $dA = dxdy$ is the size of the unit area associated with $\vec{r}''$ and $\delta$ is the Kronecker delta. Substituting Eq. S7 into Eq. S6 yields Eq. 3 of Example 2.

The modeling of the premyofibril bundling and reorientation during the maturation process are addressed separately. The temporal change of premyofibril bundling, $|u|$, is expressed as $$\frac{\partial |\vec{u}|}{\partial \tau} = S_0 |\vec{S}| - |\vec{u}|, \tag{S8}$$

where $S_0$ is a scaling factor such that $0 < S_0 |\vec{S}| < 1$, and $S_0 |\vec{S}|$ as well as $-|u|$ represent the parallel bundling and unraveling of premyofibrils, respectively. Note that Eq. S8 matches Eq. 4 of Example 2.

The orientation of individual premyofibrils is regulated by the local stress fiber bundles as well as the rotational forces imposed by neighboring premyofibrils. Consider the unit vectors representing two adjacent premyofibrils, $|\hat{u}|$ and $\hat{u}'$. The intersection of these two vectors gives two angles $\theta$ and $\pi - \theta$, in which $\cos(\theta) = \hat{u} \cdot \hat{u}'$ and $\cos(\pi - \theta) = \hat{u} \cdot (-\hat{u}')$. Since the premyofibrils are bi-directional, minimizing the smaller of $\theta$ and $\pi - \theta$ will align $\vec{u}$ and $\vec{u}'$ in parallel. This is achieved by assuming that $\hat{u}'$ creates a torque, $$\hat{u} \times (\hat{u}' \times \hat{u}) \cos^2 \frac{\theta}{2}$$

on $\hat{u}$, and $-\hat{u}'$ creates an opposing torque, $$\hat{u} \times (-\hat{u}' \times \hat{u}) \cos^2 \frac{\pi - \theta}{2};$$

here, a half-angle is applied to ensure that smaller angles generate larger torque. The total torque from premyofibril $\vec{u}'$ on $\vec{u}$ is the sum of the individual torques. We further assume that the torque exerted on $\vec{u}$ is proportional to $|\vec{u}'|$. Together, we have Eq. 5 of Example 2:

$$\frac{\partial \hat{u}}{\partial \tau} = u_0 \int_{\Omega'} \{|u'|(\hat{u}' \cdot \hat{u})[\hat{u}' - (\hat{u}' \cdot \hat{u})\hat{u}]\} d^2 r' + \hat{S} - \hat{u}. \tag{S9}$$

Here, the first term accounts for the constraints imposed by neighboring premyofibrils, the second term is from the stress fiber network, and the last term is the decay. The parameter $u_0$ is a scaling factor, $\hat{S}$ is the unit vector of $\vec{S}$, and $\Omega'$ stands for the spatial domain containing the premyofibrils in the neighborhood of $\vec{u}$. Note that the first term is only considered when $|\vec{u}|$ is not zero.

In our numerical analysis, the longest dimension of the cells was chosen to be 50 μm to ensure consistency with experimental conditions and was normalized to 1, with the unit length of the premyofibrils set to 2 μm, the sarcomere length (0.04 after normalization). For consistency, we applied the same parameter values across the different shapes, namely, $\alpha_0 = 10^{-3}$, $\beta_0 = 10^{-3}$, $\rho_{sat} = 25$, $T_0 = 100$, $d_0 = 5$, $u_0 = 20$, $d = 1.5$, and $H_0 = 2$, based on similar values for relevant parameters in the literature (I. L. Novak et al. (2004) *Phys Rev Lett*

93, 268109). Each simulation began with a random premyofibril bundling and orientation, and random spatial distribution of ρ, $\vec{S}$, and $\vec{u}$.

Cardiac Myocyte Culture.

Trypsinized ventricular tissue isolated from 2-day old neonatal Sprague Dawley rats (Charles River Laboratories) was serially dissociated into single cells by treating the ventricular tissue 4 times with a 0.1% solution of collagenase type II (Worthington Biochemical) for 2 minutes at 37° C. The myocyte fraction was purified by passing the dissociated cells through a nylon filter with 40 μm pores (BD Bioscience) and pre-plating the cells twice for 45 minutes each time. Purified myocytes were plated onto micropatterned substrates prepared as described below at a density of 100,000 cells per coverslip and kept in culture at 37° C. with a 5% $CO_2$ atmosphere. The culture medium was M199 base supplemented with 10% heat-inactivated Fetal Bovine Serum, 10 mM HEPES, 20 mM glucose, 2 mM L-glutamine, 1.5 μM vitamin B-12, and 50 U/ml penicillin. The media was changed 24 hours after plating to remove unattached and dead cells and every 48 hours afterwards. After 72 hours in culture, most cardiac myocytes beat spontaneously and were used either for immunostaining or traction force measurements.

Micropatterning Substrates.

Figure 15:
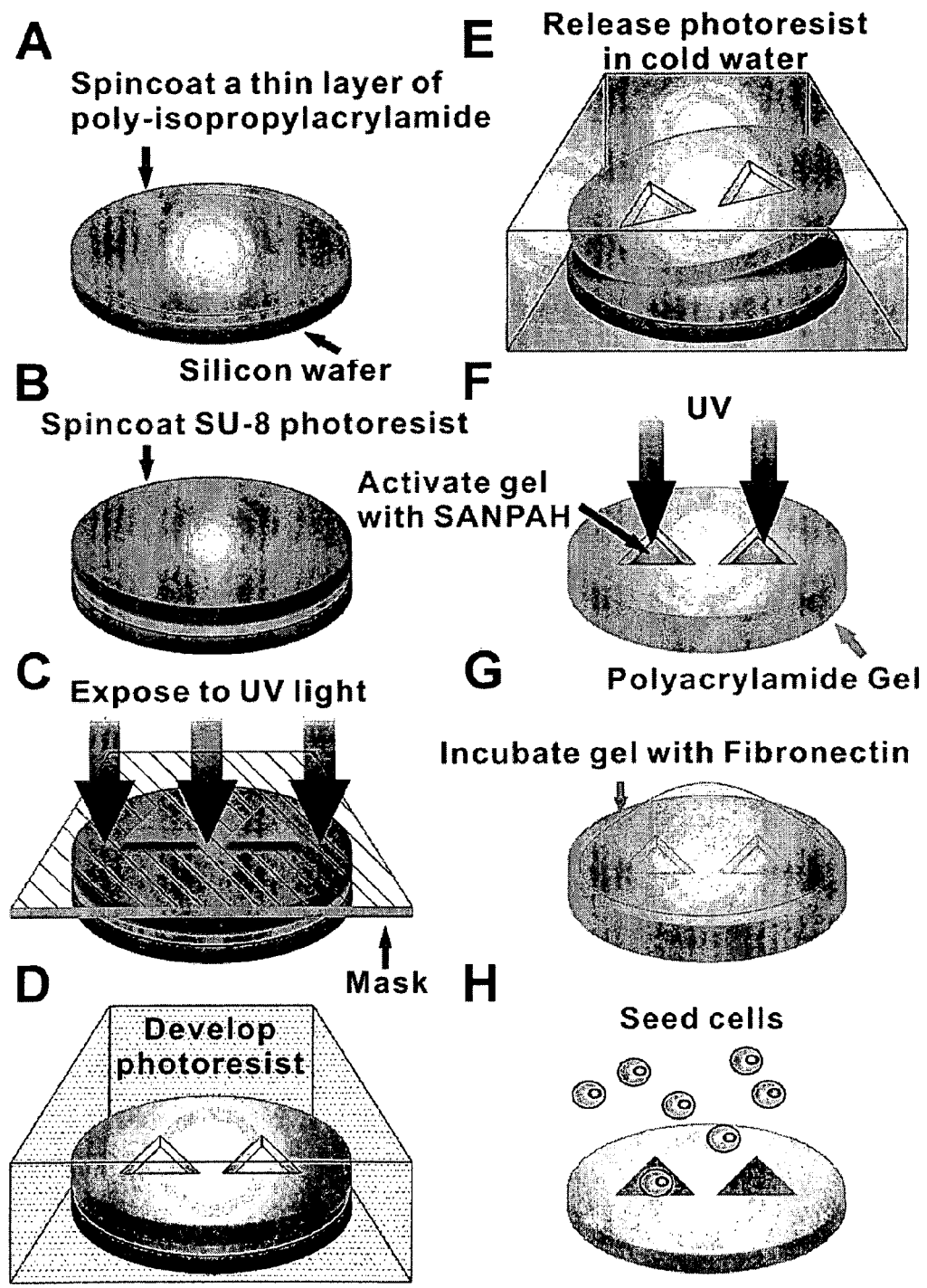
FIG. 15 shows a schematic representation of micropatterning FN (fibronectin) on polyacrylamide gel. After a thin layer of PIPAAm (poly-N-iso-propylacrylamide) was spin-coated on a silicon wafer (A), SU-8 photoresist was spin-coated on top of the PIPAAm (B), treated with UV light through a photolithographic mask (C), and developed to obtain a complementary master (D). The master was immersed in ice water to release the photoresist membrane (E). The photoresist membrane was placed on the surface of polyacrylamide gels and sulfo-SANPAH (sulfosuccinimidyl-6-4-azido-2-nitrophenylamino-hexanoate) was added to the gel surface, photoactivated by UV light (F). FN solution was then added to react with the photoactivated gel (G). After removal of the photoresist membrane, the gel was immediately used for cell plating (H).

Micropatterned substrates containing square, triangular, or circular adhesive islands were prepared for immunostaining and traction force microscopy, as follows. For immunostaining, the substrates were micropatterned using a microcontact printing procedure similar to that described by Tan et al. (2004) *Tissue Eng* 10:865. Micropatterned substrates for traction force experiments were created by adapting published techniques (C8-10) (M. Dembo & Y. L. Wang (1999) *Biophys J* 76:2307; R. J. Pelham, Jr. & Y. Wang (1997) *Proc Natl Acad Sci USA* 94:13661; N. Wang et al. (2002) *Cell Motil Cytoskeleton* 52:97). Briefly, a thin layer of 10% by weight poly-N-iso-propylacrylamide (PIPAAm) prepared in 1-butanol was spin coated on a silicon wafer (FIG. 15A). A 50~75 μm layer of SU-8 photoresist was spin-coated on top of the PIPAAm (FIG. 15B), UV light treated through a photolithographic mask (FIG. 15C), and developed to obtain a complementary master that contained holes with the same size and shape as the desired adhesive islands (FIG. 15D). The master was immersed in ice water to dissolve the PIPAAm and the photoresist membrane was released from the wafer (FIG. 15E). Polyacrylamide gels (0.1% bis and 5% acrylamide; ~0.90 μm thick) containing 1:500 volume of carboxylate-modified fluorescence latex beads (0.2 μm Fluospheres, Molecular Probes, Eugene, Oreg.) were fabricated on 25 mm coverslips. The Young's modulus of the gel was estimated to be ~3 KPa using atomic force microscopy as described previously (A. Engler et al. (2004) *Biophys J* 86:617). The photoresist membrane was placed on the surface of the gel and 1 mM sulfo-SANPAH (sulfosuccinimidyl-6-4-azido-2-nitrophenylamino-hexanoate; Pierce, Rockford, Ill.) in 50 mM HEPES was added through the holes in the photoresist membrane. The whole system was then placed under vacuum for 3 minutes to ensure that the sulfo-SANPAH reached the gel surface. The gel surface that contacted the sulfo-SANPAH was photoactivated by UV light exposure (FIG. 15F). After excess sulfo-SANPAH was removed, fibronectin (FN) 100 μg/mL was added to the membrane and the gel was placed under vacuum for another 3 minutes to remove bubbles from the holes (FIG. 15G). FN was allowed to react with the photoactivated gel for at least 4 hours at 37° C. to create FN-coated adhesive islands. Excess FN was washed away with PBS. After removal of the photoresist membrane, the gel was immediately used for cell plating (FIG. 15H).

Traction Force Microscopy Data Analysis.

Fluorescence images of gels containing fluorescent beads immediately beneath the contracting myocytes were taken at 28.1 Hz. The duration of image acquisition was long enough to include at least two complete cycles of contraction-relaxation of individual myocytes. Consecutive images were paired and the prior image was used as a reference to measure the change of the position of the fluorescence beads using the algorithm described by Butler et al. (2002) *Am J Physiol Cell Physiol* 282:C595. This yielded the discretized displacement field between two consecutive frames. The calculated displacements were summed for a whole systolic cycle to determine the overall 2D displacement field. The contractile traction field was calculated from the displacement field by adapting the algorithm developed by Schwarz et al. (2002) *Biophys J* 83:1380. This algorithm solved the inverse of the Boussinesq solution from the displacement field on the surface of an elastic halfspace to obtain the traction field when the mechanical properties of the gel are known. The Poisson ratio of the gel was assumed to be close to 0.5 (N. Wang et al. (2002) *Cell Motil Cytoskeleton* 52:97). The interior of the cell was subdivided into 4×4 μm$^2$ squares to approximate the discretized localization of contractile forces. The ability of a particular solved traction field to explain the observed displacements was estimated with $\chi^2$ statistics. In addition to a zero-order Tikhonov regularization, a constraint that the forces should not become exceedingly large was used to minimize and stabilize the solution. The L-curve criterion, as previously described, was used to determine the optimal balance between the data agreement and the regularization (U.S. Schwarz et al. (2002) *Biophys J* 83:1380).

Immunofluorescent Staining and Imaging.

Cardiac myocytes stained for actin (Alexa 488 Phalloidin, Molecular Probes, Eugene, Oreg.), vinculin (clone hVIN-1, Sigma, St. Louis, Mo.), and sarcomeric α-actinin (clone EA-53, Sigma) were fixed in 4% PFA with 0.01% Triton X-100 in PBS buffer at 37° C. for 15 minutes and equilibrated to room temperature during incubation. Secondary staining was performed using tetramethylrhodamine-conjugated goat anti-mouse IgG (Alexa Fluor 594, Molecular Probes), and nuclei were visualized by staining with 4',6'-diamidino-2-phenylindole hydrochloride (DAPI, Molecular Probes). All fluorescence and traction force microscopy was conducted with a Leica DMI 6000B microscope, using a 63× planapochromat objective. For traction force experiments, images were collected with a Cascade 512b enhanced CCD camera, while immunofluorescence images were collected with a CoolSnap HQ CCD camera (both from Roper Scientific, Tucson, Ariz.) controlled by IPLab Spectrum (BD Biosciences/Scanalytics, Rockville, Md.).

Example 4

Application of Boundary Conditions to Direct Multiscale Functional Coupling of Tissue Structures Containing Aligned Subcellular Organelles into Engineered Tissue with Wild-Type Equivalent Contractility Engineered Myocardium Myocardial regeneration promises to one day repair myocardial infarction, the leading cause of heart failure and death in the industrialized world. To this end, there is still much to be learned and leveraged in our understanding of heart function as we manipulate cells and direct them to grow into new muscle. There is a structure-function hierarchy in myocardium that spans from the actin-myosin molecular motor at the nanometer scale to the ventricle at the macroscale. Electromechanical coupling across these dimensions coordinates function in space and time, but this homeostasis breaks down in disease when force and/or electrical synchronization are impaired. Thus, one critical issue in cardiac tissue engineering is how to put cardiomyocytes together from single-cells into tissues. As a result, there is a need to understand and direct how cell-cell coupling at the microscale translates to macroscale electromechanical function.

Described herein are the design and fabrication methodologies to implement a system to build 2- and 3-dimensional tissue and study structure-function relationships in such tissues. For example, engineered myocardial tissue is used to as a model to evaluate healthy heart and myopathies, combining ultrastructural analysis with functional readouts of contractility and action potential propagation. This system serves as a model for understanding muscle physiology and pathophysiology. Two-dimensional (2D) muscle tissue monolayers that recapitulate in vivo tissue microstructure were made. Such monolayers are combined to make functional muscle masses. These tissue engineering capabilities have been leveraged to build muscle that mimics the structure of myopathic disease states and healthy heart. Relevant muscle tissue microstructure has been quantified; specifically the density, aspect ratio and orientation of the cell body, nucleus, and contractile elements (sarcomeres for cardiomyocytes and dense bodies for smooth muscle cells). Muscle tissue contractile force, specifically the shear force relevant to muscle sheets, was measured.

A myocardial tissue structures are useful as a model for the whole heart. In the heart, myofibers are interconnected by an ECM of predominantly collagen that provides the basic structural integrity (J. B. Caulfield & T. K. Borg (1979) *Lab Invest* 40:364-372). These myofibers are structurally arranged in laminar sheets that have been found to be 4±2 myocytes thick in dogs (I. J. Legrice et al. (1995) *Am J Physiol-Heart Circul Physiol* 38:H571-H582). Myocytes within the sheets are well aligned but the orientation of the sheets themselves varies from −41° to +42° moving from the epicardium to endocardium in sheep (and over similar ranges for other species)(K. B. Harrington, et al. (2005) *Am J Physiol-Heart Circul Physiol* 288:H1324-H1330). As the myocardium contracts the sheets also change vertical inclination adopting a more radial orientation (J. J. Chen et al., (2005) *Am J. Physiol-Heart Circul Physiol* 289:H1898-H1907).

Two-dimensional muscle monolayers are combined into 3-D tissue while maintaining sheet architecture, i.e., sarcomere and concomitant cell alignment based on organelle alignment, interconnections between the sheets and multi-axial deformation during contraction. A 3-D tissue mass, e.g., a muscle or muscle patch, is generated or built by laying, extruding, or otherwise combining a plurality (e.g., $1 \times 10^3$, $1 \times 10^4$, $1 \times 10^5$, $1 \times 10^6$, $1 \times 10^7$, $1 \times 10^8$, $1 \times 10^9$, or more) muscular thin film units, either sequentially or simultaneously. Thus, in addition elucidating the physiological responses to stresses or test compounds, the methods described herein provide tissues for therapeutic use. The 3-D engineered tissue are also used to customize or optimize food, e.g., meat, for human or animal consumption.

In general, systems are useful for studying a variety of cell types and understand biochemical pathways, response to drugs or toxins, e.g., screening assays, and gene expression. An advantage of the systems described herein for 2D and 3D tissues is the ability to control tissue structure (e.g., texture), to quantify structural properties of the muscle cells using established microscopic techniques, to record electrical signals and to measure contractile force with high precision. The following capabilities are demonstrated. First, engineering the growth of 2D myocardium and 2D vascular media on cover slips to create tissue with tailored anisotropy. Second, anisotropic 2D tissues of cardiomyocytes are imaged using standard microscopic methods to visualize subcellular structures. Third, anisotropic 2D tissues are released from rigid cover slips as a free-standing monolayer of muscle coupled to a flexible polymer film (A. W. Feinberg et al. (2007) *Science* 317:1366-1370). Fourth, contraction of the muscle layer can be used to quantify contractility.

Building 2-Dimensional Myocardial Sheets with Hierarchical Structure

Two-dimensional (2D) myocardium was engineered using boundary conditions to enable multi-scale, hierarchical function that approximates natural cardiac muscle using the ability to control micrometer and nanometer cell-cell coupling and to direct this over multiple spatial dimensions up to the macroscale (centimeters to meters). This is illustrated in FIG. 1 in the context of aligning the actin-myosin motor complexes, nanometer scale molecular motors that generate the force of macroscale contraction.

Figure 16:
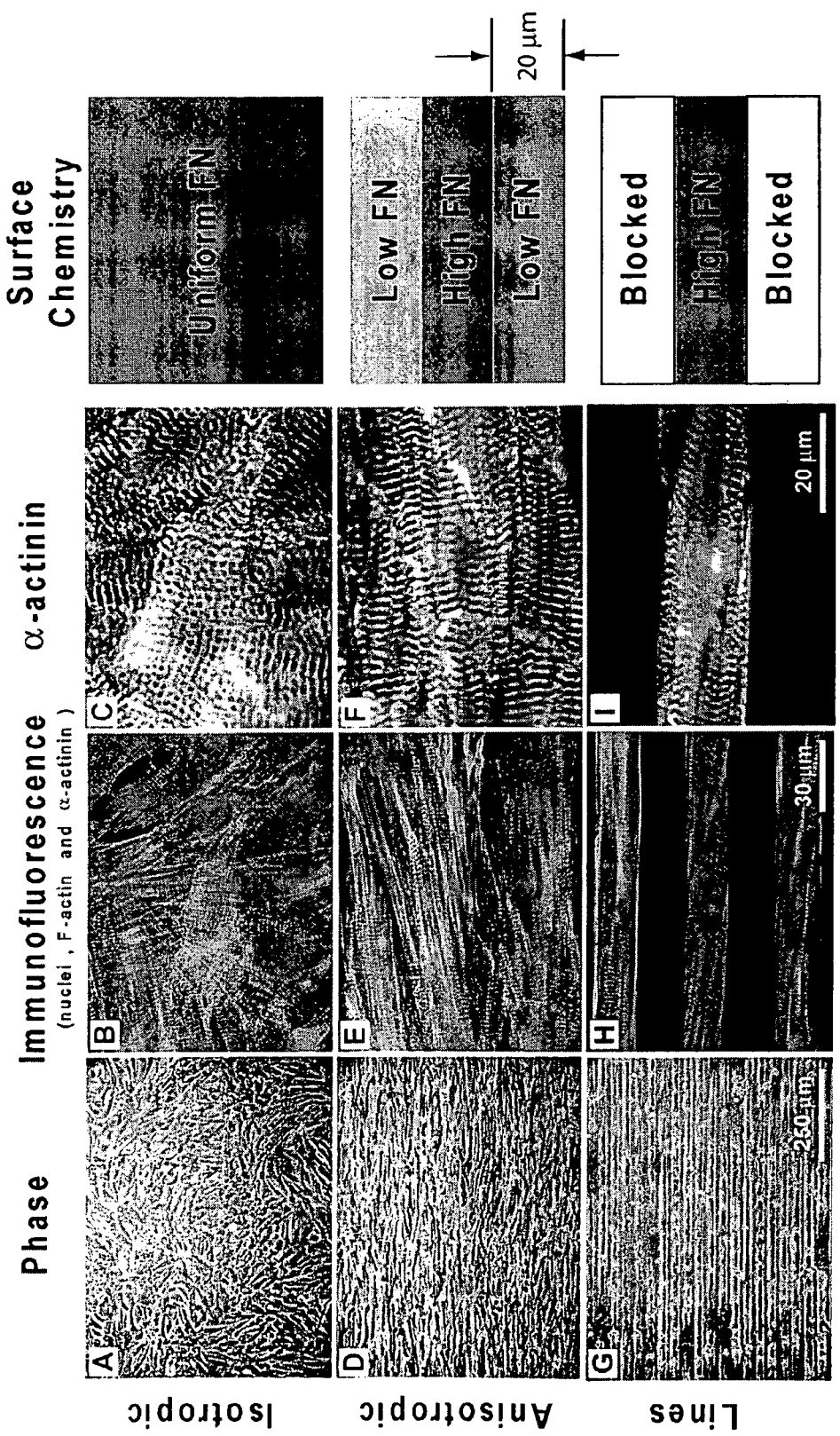
FIG. 16 shows the microstructure of 2D myocardium engineered to be isotropic or anisotropic in order to control contractility. Uniform FN coatings produced isotropic 2D myocardium (A, B, and C) with no long-range order. (C) Staining for sarcomeric α-actinin revealed no preferential alignment of sarcomeres along any axis. Micropatterns of alternating high and low density 20 µm wide FN lines (D, E and F) produced continuous anisotropic 2D myocardium. (F) Staining for sarcomeric α-actinin revealed uniaxial alignment of sarcomeres along a single axis. Micropatterns of alternating 20 µm wide lines of high density FN and Pluronics (G, H and I) produced an array of discrete muscle fibers. (I) Staining for sarcomeric α-actinin revealed uniaxial alignment of sarcomeres along a single axis. Images are phase contrast (A, D and G); immunofluorescence of nuclei (blue), F-actin (green) and sarcomeric α-actinin (red) (B, E and H); and the signal from sarcomeric α-actinin alone (C, F and I) to indicate and emphasize the direction of sarcomere alignment. The right most column shows the fibronectin boundary conditions that were used to direct 2D myogenesis. These were uniform FN for isotropic; alternating high and low density FN lines for the anisotropic; and alternating high density FN lines with Pluronics F127 to block additional protein adsorption.

The boundary conditions used to create the multiscale hierarchical muscle structure are geometrically micropatterned regions of the extracellular matrix protein fibronectin (FN). FN was patterned onto thin elastic membranes of polydimethylsiloxane (PDMS) rubber using microcontact printing. The FN was patterned as 20 micrometer wide, 20 micrometer spaced lines that were 1 centimeter in length. The space in between the lines was either adsorbed with a lower density of FN or were coated with a hydrophilic surfactant (Pluronics F127) designed to stop additional protein adsorption. Thus, three types of boundary conditions were compared as shown in FIG. 16. These are ISOTROPIC, which has a uniform FN surface density and thus no boundary conditions are present. ANISOTROPIC has the alternating high and low density FN lines. LINES have the high density FN lines with Pluronics in between that block additional protein adsorption. The end result is the ability to create three different microscale coupling environments that influence macroscale contractility. Isotropic surfaces have no direction of cell alignment. Anisotropic surfaces have uniaxial cell alignment where the sarcomeres are oriented in the same direction. The lines surfaces have few cells, but they are better aligned with improved sarcomere uniaxial alignment.

These three boundary conditions were used to generate muscular thin films (MTFs) where 2D myocardium is integrated into a free standing PDMS film. A contractility assay allows the deformation of the MTF (FIG. 17) to be observed and converted into the force generated by the muscle tissue. Results show that the use of boundary conditions that direct microscale cell-cell coupling and hierarchical organization into a macroscale muscle tissue can control contractile force at the macroscale. Further, the frequency at which the muscle contracts can be altered to simulate a number of heart rates (FIG. 18).

Figure 17:
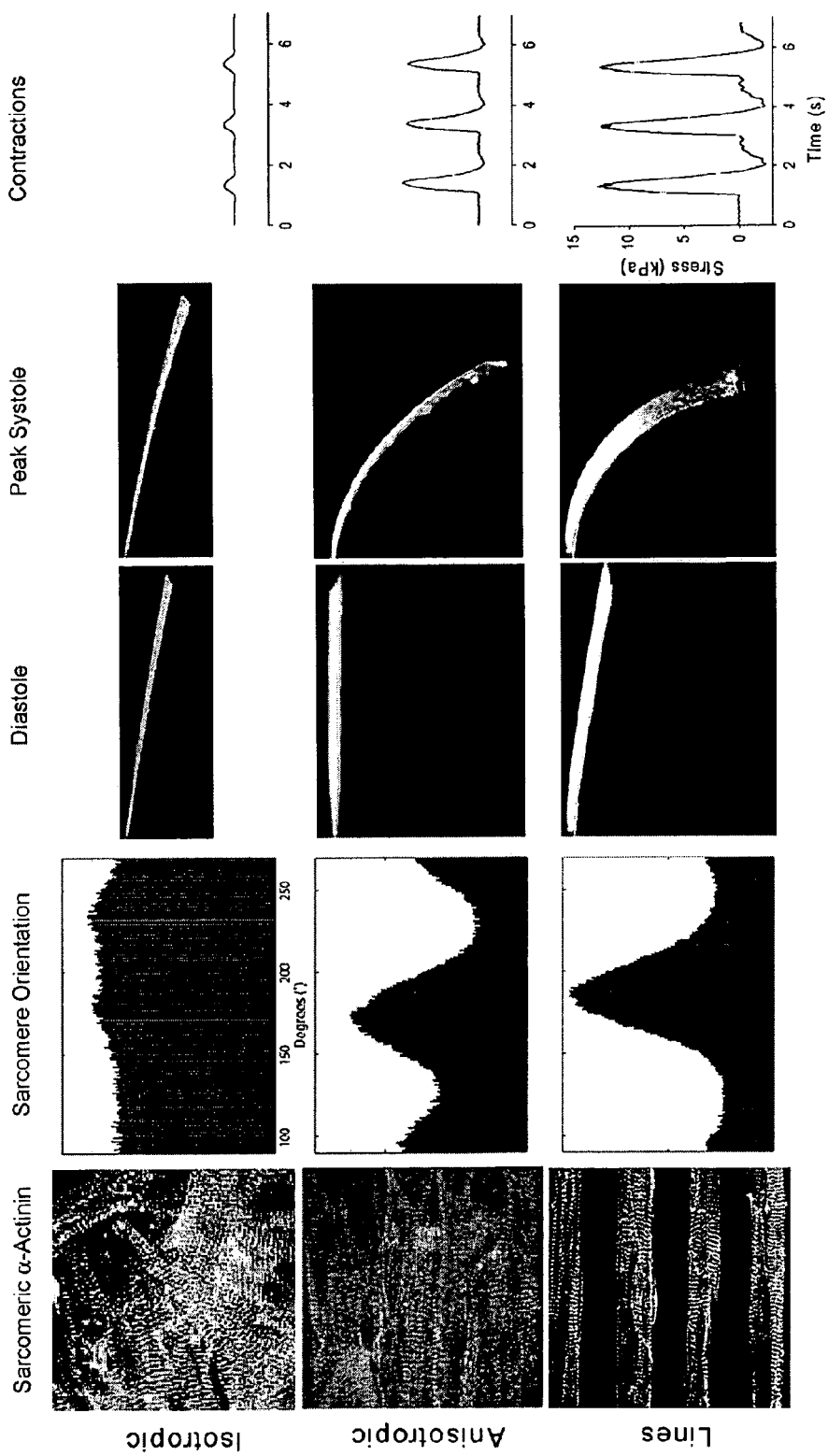
FIG. 17 shows examples of sarcomere alignment, muscular thin films and resulting contractile force generated from the three engineered boundary conditions described in FIG. 16. The first column shows the microscale cell-cell coupling created by the boundary conditions and the orientation of the sarcomeres as stained for the sarcomeric alpha-actinin in the Z-disks. The second column shows the uniaxial sarcomere orientation as quantified using image analysis software for typical examples of 2D myocardium for each boundary condition. The third column show muscular thin films in diastole (relaxed state) for each boundary condition. The fourth column shows muscular thin films in peak systole (maximum contraction) for each boundary condition. The fifth column shoes the actual force generated by each muscular thin film at 0.5 Hz pacing for each boundary condition. The use of engineered boundary conditions increases both uniaxial sarcomere alignment and contractile force.
Figure 18:
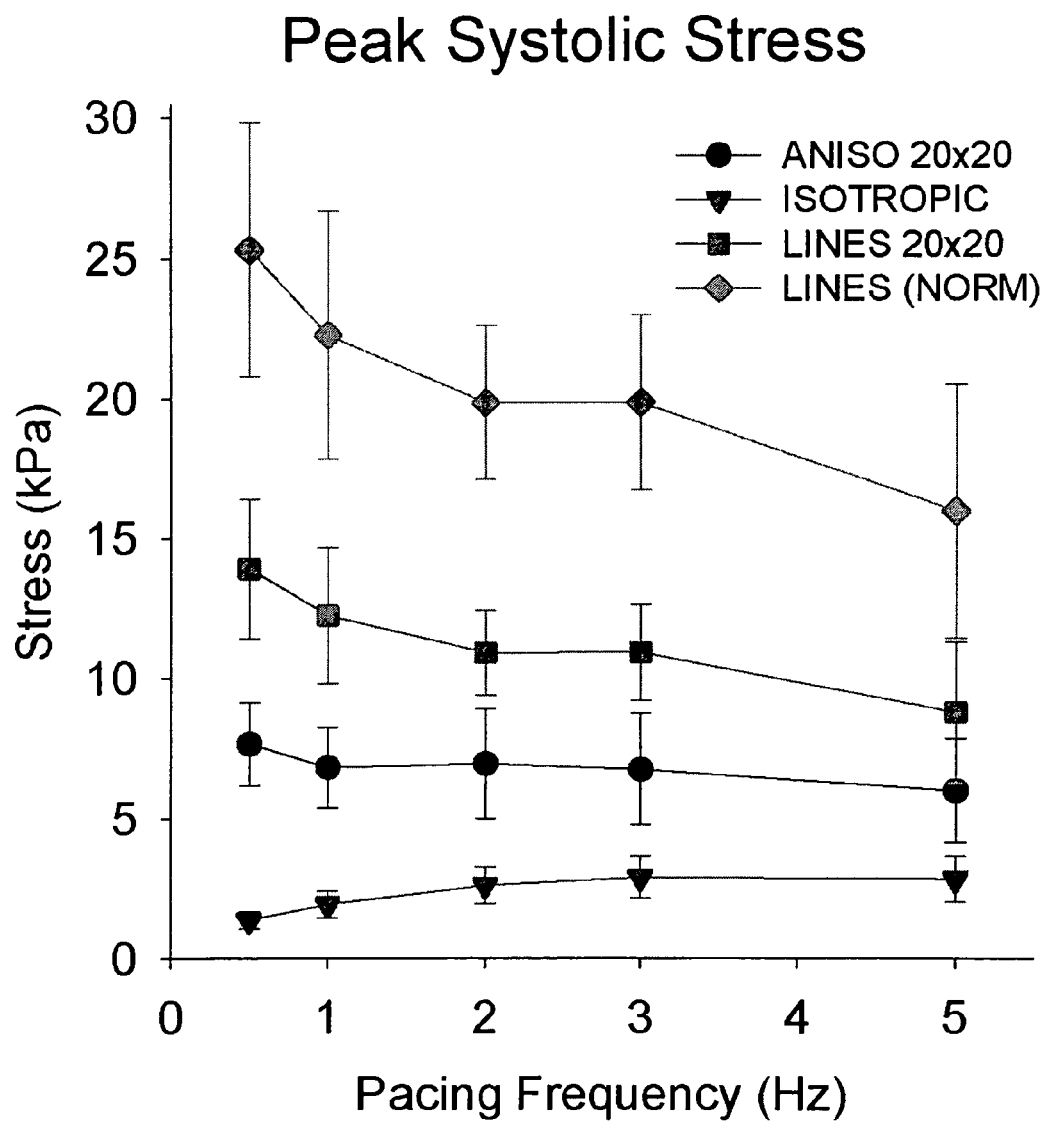
FIG. 18. shows data from multiple muscular thin films paced at 0.5, 1, 2, 3 and 5 Hz where the muscular thin films were created using isotropic, anisotropic and line boundary conditions. In all pacing conditions the use of boundary conditions that direct multiscale, hierarchical myogenesis enhanced contractile force, generating contractility equivalent to natural muscle.

As shown in FIG. 17, the sarcomere orientation within the muscle cells (at the nanometer scale) as a function of the boundary conditions used to direct myogenesis was quantified. The uniaxial sarcomere alignment increased with the discreteness of the FN boundary where LINES>ANISOTROPIC>ISOTROPIC. The force generated by the MTFs for each type of boundary condition shows a direct relationship between the sarcomere alignment at the nanometer scale and the force of contraction at the macroscale.

Finally, the use of boundary conditions allows engineered myocardium to be created with contractile force that matches wild-type (natural) muscle in the case of the anisotropic condition or exceeds wild-type (natural) muscle in the case of the lines condition.

Muscular Thin Film Fabrication.

Muscular thin films (MTFs) were fabricated via a multi-step spin coating process as previously described (A. W. Feinberg et al. (2007) *Science* 317:1366-1370). Briefly, poly (N-isopropylacrylamide) (PIPAAm, Polysciences, Inc.) was dissolved at 10 wt % in 99.4% 1-butanol (w/v) and spin coated onto 25 mm diameter glass cover slips. Sylgard 184 (Dow Corning) polydimethylsiloxane (PDMS) elastomer was mixed at a 10:1 base to curing agent ratio and spin coated on top of the PIPAAm coated glass cover slips to a thickness of ~30 µm The PDMS/PIPAAm coated cover slips were cured at 65° C. for 4 hours. The cured PDMS/PIPAAm coated cover slips were functionalized with the extracellular matrix protein fibronectin (FN) according to one of three conditions; (i) isotropic, (ii) anisotropic or (iii) lines. The PDMS/PIPAAm coated cover slips were first UV ozone treated (Model No. 342, Jetlight Company, Inc.) to sterilize the surface and increase hydrophilicity, important to enhance the adhesion of FN to the PDMS. Isotropic FN was deposited by placing a 1 mL lens of 25 µg/mL FN in sterile deionized (DI) water on the PDMS and incubating for 15 minutes. Anisotropic patterned FN was generated using microcontact printing (µCP) with PDMS stamps to pattern FN on the PDMS as previously described (A. W. Feinberg et al. (2007) *Science* 317:1366-1370). Briefly, PDMS stamps with 20 µm wide, 20 µm spaced ridges were used to transfer FN to the PDMS/PIPAAm coated cover slip creating 20 µm wide, 20 µm spaced FN lines. Either 1% Pluronics F127 (BASF Group) or 2.5 µg/mL FN in DI water was incubated on the cover slip surface for 15 minutes, in order to direct formation of 2D anisotropic strands (lines) or 2D anisotropic tissue respectively.

Cardiomyocyte Harvest, Seeding and Culture.

Neonatal rat ventricular myocytes were isolated from 2-day old neonatal Sprague-Dawley rats. Ventricles were extracted and homogenized by washing in Hanks balanced salt solution followed by digestion with trypsin and collagenase with agitation overnight at 4° C. Subsequently, cells were re-suspended in M199 culture medium supplemented with 10% (v/v) heat-inactivated fetal bovine serum (FBS), 10 mM HEPES, 3.5 g/L glucose, 2 mM L-glutamine, 2 mg/L vitamin B-12, and 50 U/ml penicillin and seeded at a density of 1 million cells per coverslip. Samples were incubated under standard conditions at 37° C. and 5% $CO_2$. Streptomycin was not added to the media in order to prevent interference with stretch activated ion channels. Media was exchanged with maintenance media (2% FBS) every 48 hours until use, typically 3 to 5 days, but never longer than 6 days post seeding. All procedures were approved by Harvard animal care and use committee.

Muscular Thin Film Contractility Assay.

Muscular thin films (MTFs) were cultured for 4 days until the cardiomyocytes had conformed to the FN patterning and subsequently used in contractility assays. The MTFs adhered to cover slips were removed from the incubator and placed into a Petri dish filled with 37° C. normal Tyrode's solution (1.192 g of HEPES, 0.901 g of glucose, 0.265 g of $CaCl_2$, 0.203 g of $MgCl_2$, 0.403 g of KCl, 7.889 g of NaCl and 0.040 g of $NaH_2PO_4$ per liter of deionized water). The Petri dish was placed on a stereomicroscope (Leica model MZ6 with darkfield base) and rectangles ~3 mm wide and 10 mm long were cut out using a straight-blade razor ensuring that the alignment of the anisotropic 2D muscle tissue was parallel to the long axis of the rectangle. As the Tyrode's solution and MTF cooled below 35° C., the PIPAAm dissolved releasing the MTF from the cover slip and into solution. Contractility assays were conducted using a custom-built organ bath system where a Petri dish was mounted in an aluminum stage plate with integrated resistive heaters that maintained the Tyrode's solution at physiologic temperatures (37° C.) for the duration of the experiment. Mounted inside the Petri dish was a small PDMS clamp (~5×5×10 mm) held in place by minutia pins epoxied to the Petri dish bottom. The MTF was positioned in the PDMS clamp such that the stereomicroscope looking down on the organ bath viewed the MTF edge on. Digital video of MTF contractions were recorded at 130 frames-per-second using a Basler A601f camera and custom LabView software while paced using parallel platinum wire electrodes spaced ~1 cm apart and lowered directly into the Petri dish. An external field stimulator (Myopacer, IonOptix Corp.) was used to apply a 10 V, 10 msec duration square wave pulse between the electrodes at pacing rates from 0.1 to 10 Hz for durations of 10 sec up to 30 minutes. The digital video was converted to a binary skeleton representation using ImageJ and then loaded into MATLAB (Mathworks, Inc.) where the curvature was used to determine the stress generated according to a modified Stoney's equation. The standard form of Stoney's equation requires that the coating be less than 1% the thickness of the substrate. The 2D myocardium thickness (~5 µm based on laser scanning confocal images) was 10% to 30% the thickness of the PDMS film requiring a correction factor to be applied to account for this deviation. The error was reduced to less than 1% using the modified Stoney's equation introduced by Atkinson (A. Atkinson (1995) *British Ceramic Proceedings* 54:1-14; C. A. Klein (2000) *Journal of Applied Physics* 88:5487); where $\sigma$ is cardiomyocyte contractile stress, E is elastic modulus of the PDMS, t is PDMS thickness, R is MTF radius of curvature, h is 2D myocardium thickness and $\upsilon$ is Poisson's ratio of the PDMS. For this system, PDMS elastic modulus is E~1.5 MPa (10), $\upsilon$=0.49 (11), h~5 µm (based on confocal and AFM data), t is typically 30 µm (measured using a stylus profilometer) and R is determined by the MATLAB code for each video clip frame.

Staining, Imaging and Quantification of Cytoskeletal Architecture.

PDMS coated cover slips with 2D muscle tissue were fixed and stained at time points concurrent with MTF experiments in order to compare cell structure with contractile function. Cardiomyocytes were fixed with 4% paraformaldehyde and 0.25% Triton X-100 and then fluorescently stained. Sarcomeres were visualized by staining the Z-disks with monoclonal mouse anti-(sarcomeric α-actinin) primary antibody (Sigma) followed by staining with fluorescently labeled secondary antibodies. Samples were stained with DAPI (Sigma) and phalloidin conjugated to Alexa-Fluor 488 (Invitrogen). Samples were imaged on a Leica DMI 6000B inverted light microscope in epifluorescense using a CoolSNAP HQ digital camera (Roper Scientific). Nuclei were analyzed from the DAPI stained images using MATLAB to fit an ellipse to each nucleus and, based on this ellipse, to calculate nuclear area, major and minor axes lengths, eccentricity and alignment angle to the horizontal image axis. To analyze sarcomeres, MATLAB was used to extract information on the number, location and orientation of the sarcomeres from the raw images. The detection algorithm was based on fingerprint enhancement and detection methods that improve contrast of 'lines' in images. Briefly, grayscale images were normalized, converted to binary and then skeletonized creating a single pixel width line for each sarcomere. A vector normal to the sarcomere (i.e., in the direction of contraction) was determined for each point of the skeleton giving alignment vectors normal to the Z-lines. A histogram of orientation angles was used to determine cytoskeletal isotropy/anisotropy with a distinct peak at specific angle indicative of cell polarization.

What is claimed is:

1. An in vitro method of forming a mature muscle tissue, comprising:
   (a) providing a medium or substrate;
   (b) providing a boundary condition associated with the medium or substrate, wherein said boundary condition directs the alignment and development of dissociated muscle cells to form a mature muscle tissue;
   (c) providing the dissociated muscle cells to the medium or substrate, wherein the muscle cells arrange based upon the boundary condition; and
   (d) culturing the muscle cells to form a mature muscle tissue,
   wherein the boundary condition directs the movement and growth of the muscle cells upon interaction with the boundary condition as compared to interaction with the medium or substrate alone such that substantially all of the muscle cells and sarcomeres within the muscle cells are spatially anisotropic in at least one direction and substantially all of the muscle cells coordinately contract, thereby forming a mature muscle tissue.

2. An in vitro method of forming a mature muscle tissue, comprising:
   (a) providing a medium or substrate;
   (b) providing a boundary condition associated with the medium or substrate, wherein said boundary condition directs the alignment and development of dissociated muscle cells to form a mature muscle tissue;
   (c) providing the muscle cells to the medium or substrate, wherein the muscle cells arrange based upon the boundary condition; and
   (d) culturing the dissociated muscle cells to form a mature muscle tissue,
   wherein the boundary condition is a change in local environment as compared to the environment of the medium or substrate alone and directs the movement and growth of the muscle cells such that substantially all of the muscle cells and sarcomeres within the muscle cells are spatially anisotropic in at least one direction and substantially all of the muscle cells coordinately contract, thereby forming a mature muscle tissue.

3. The method of claim 1 or 2, wherein the boundary condition is a naturally-provided boundary condition.

4. The method of claim 1 or 2, wherein the substrate is comprised of a polymeric material.

5. The method of claim 1 or 2, wherein the boundary condition is selected from the group consisting of a physical, a mechanical, a chemical, and an electromagnetic boundary condition.

6. The method of claim 1 or 2, wherein the boundary condition is a biochemical boundary.

7. The method of claim 6, wherein the biochemical boundary comprises fibronectin.

8. The method of claim 1 or 2, wherein the boundary condition is a physical boundary.

9. The method of claim 8, wherein the physical boundary provides elasticity, surface roughness, or surface topography.

10. The method of claim 8, wherein the physical boundary comprises micro- or nano-fabricated structures, said structures selected from the group consisting of ridges, pillars, and grooves.

* * * * *